(12) United States Patent
Couto et al.

(10) Patent No.: US 7,959,921 B2
(45) Date of Patent: Jun. 14, 2011

(54) TNFα-NEUTRALIZING ANTIBODIES

(75) Inventors: Fernando Jose Rebelo Do Couto, Pleasanton, CA (US); Kristin Beth Hendricks, San Carlos, CA (US); Stacey Ellen Wallace, Sunnyvale, CA (US)

(73) Assignee: Epitomics, Inc., Burlingame, CA (US)

( * ) Notice: Subject to any disclaimer, the term of this patent is extended or adjusted under 35 U.S.C. 154(b) by 373 days.

(21) Appl. No.: 12/196,200

(22) Filed: Aug. 21, 2008

(65) Prior Publication Data

US 2009/0202558 A1    Aug. 13, 2009

Related U.S. Application Data

(63) Continuation of application No. 11/090,105, filed on Mar. 24, 2005, now Pat. No. 7,431,927.

(51) Int. Cl.
*A61K 39/395* (2006.01)

(52) U.S. Cl. .................................... 424/145.1

(58) Field of Classification Search ........................ None
See application file for complete search history.

(56) References Cited

U.S. PATENT DOCUMENTS

| | | | |
|---|---|---|---|
| 5,530,101 A | 6/1996 | Queen et al. | |
| 2003/0147891 A1 | 8/2003 | Le et al. | |
| 2003/0187231 A1 | 10/2003 | Le et al. | |
| 2003/0199679 A1 | 10/2003 | Adair et al. | |
| 2004/0002589 A1 | 1/2004 | Rathjen et al. | |
| 2004/0138427 A1 | 7/2004 | Le et al. | |
| 2004/0151722 A1 | 8/2004 | Banerjee et al. | |
| 2004/0185047 A1 | 9/2004 | Giles-Komar et al. | |
| 2005/0037008 A1 | 2/2005 | Le et al. | |

OTHER PUBLICATIONS

Balazovich et al. Tumor necrosis factor -α—and FLMLP receptors are functionally linked during FMLP-stimulated activation of adherent human neutrophils. Blood. 1996, vol. 88, pp. 690-696.
Haranaka, et al. Purification and partial amino acid sequence of rabbit tumor necrosis factor. Int J Cancer. 1985, vol. 36, No. 3, pp. 395-400.
Janeway, et al. Immunobiology: The immune system in health and disease, Third Ed., New York: Garland Pub, 1997.
Spieker-Polet, et al. Rabbit monoclonal antibodies: generating a fusion partner to produce rabbit-rabbit hybridomas. PNAS. 1995, vol. 92, No. 20, pp. 9348-9352.

*Primary Examiner* — Daniel E Kolker
*Assistant Examiner* — Gregory S Emch
(74) *Attorney, Agent, or Firm* — James S. Keddie; Bozicevic, Field & Francis, LLP

(57) ABSTRACT

The invention provides monoclonal antibodies that neutralize TNFα activity. The monoclonal antibodies may be rabbit monoclonal antibodies or monoclonal antibodies having CDR regions derived from those rabbit monoclonal antibodies. In certain embodiments, the monoclonal antibodies may be humanized. Methods of using the subject antibodies to inhibit TNFα activity, methods of treatment using those antibodies and kits containing the same are also provided. The invention finds use in a variety of research and medical applications.

14 Claims, 17 Drawing Sheets

|   |         | 1              2         =CDR1==   4 |
|---|---------|---------------------------------------|
| A | 246VH_: | _QSVEESGGRLVTPGTPLTLICTVSGIDLSS__NSMGWFRQAF |
|   | 325VH_: | _QSLEESGGGLVKPEGSLTLTCTASGFSFSSS_YYMCWVRQAF |
|   | 818VH_: | _QSVKESEGGLFKPDETLTLTCTVSEIDLSG__NQISWVRQAF |
|   | 830VH_: | _QSVKESEGGLFKPAETLALTCTVSGIDLSR__NSISWVRQAF |
|   | 876VH_: | _QSVKESEGGLFKPTDTLTLTCTVSGFSLII__DGVSWVRQAF |
| B | 703VH_: | _QSLEESGGGLVKPGGTLTLTCTVSGIDLSN__DAISWVRQAF |
|   | 710VH_: | _QSLEESGGGLVKPGGTLTLTCTVSGIDLSN__DAISWVRQAF |
|   | 715VH_: | _QSLEESGGGLVTPGGTLTLTCTVSGIDLRN__DAISWVRQAF |
|   | 825VH_: | _QSLEESGGGLVKPGGTLTLTCTVSGIDLSN__DAISWVRQAF |
|   | 867VH_: | _QSLEESGGGLVKPGGTLTLTCTVSGIDLSN__DAISWVRQAF |
| C | 52VH__: | QEQLKESGGGLVTPGGTLTLTCTASGFTISS__YVMTWVRQAF |
|   | 63VH__: | _QSVEESGGRLVTPGGSLTLTCTVSGFSLSS__FVMSWVRQAF |
|   | 115VH_: | _QSVEESGGRLVTPGGSLTLTCTVSGFSLSS__FVMSWVRQAF |
|   | 473VH_: | _QSLEESGGDLVKPGASLTLACTASGFTISRS_YWICWVRRAF |
|   | 92VH__: | _QSVKESEGGLFKPTDTLTLTCTVSGFSLRD__DAISWVRQAF |
|   | 406VH_: | __QLVESGGGLVQPEGSLTLTCTASGFSFSRY_YYICWVRQAQ |
|   | 502VH_: | QEQLEESGGDLVKPGASLTLTCTASGFSFSVG_YWICWVRQAF |
|   | 857VH_: | _QSVEESGGRLVTPGTPLTLTCTASGFSLSS__YYMGWFRQAF |
|   | 37VH__: | _QSLEESGGRLVTPGTPLTLTCTVSGFSLSR__YYMSWVRQAF |
|   | 12VH__: | _QSLEESGGDLVKPGGTLTLTCKSSGFDFST__DAMCWVRQAF |
|   | 89VH__: | QEQLEESGGDLVKPEGSLTLTCTASGFSFSSN_YWMCWVRQAF |
|   | 438VH_: | ESLEESGGDLVKPGASLTLTCKASGVDFSYY_YYMCWVRQAF |
|   | 456VH_: | __QLEESGGGLVKPGGTLTLTCKASGIDFSSG_YYMCWVRQAF |
| D | 1VH___: | _QSVKESEGGLFKPTDTLTLTCTVSGISLSS__NEISWVRQAF |
|   | 204VH_: | _QSVKESEGGLFKPTDTLTLTCTVSGFSLNS__NEISWVRQAF |
| E | 427VH_: | _QSLEESGGDLVKPGASLTLTCTASGFTLSS__YYMCWVRQAF |
|   | 45VH__: | _QSLEESGGDLVKPGASLTLTCTASGLSFSS__YYMCWVRQAF |
|   | 431VH_: | _QSLEESGGDLVKPGASLTLTCTASGFSFSSS_IYMCWVRQAF |
| F | 101VH_: | _QSVKESEGGLFKPTDTLTLTCTVSGFSLSR__YGVSWVRQAF |
|   | 810_81: | _QSVKESEGGLFKPADTLTLTCTVSGFSLSR__YGVSWVRQAF |
|   | 858VH_: | _QSVKESEGGLFKPTDTLTLTCTVSGFSLSR__YGINWVRQAF |
|   | 877VH_: | _QSVKESEGGLFKPTDTLTLTCTVSGFSLSR__YGVTWVRQAF |
|   | 518VH_: | _QSLEESGGRLVTPGTPLTLTCTVSGIDLSS__YHMCWVRQAF |
|   | 878VH_: | _QSVEESGGRLVTPGTPLTLTCTVSGFSLST__YNMIWVRQAF |
|   | 442VH_: | __QLVESGGGLVQAGESLKLSCKASGIDFSN__YGITWVRQAF |
|   | 816VH_: | _QSVEESGGRLVAPGTPLTLTCTVSGFSLSS__GAMSWVRQAF |
|   | 2VH___: | _QSLVESGGGLVKPGASLTLTCKASGFSFSSG_DDMCWVRQAF |
|   | 410VH_: | VQLEESGGDLVKPGASQTLTCTASGIDFSAG_HYMCWVRQAF |
| G | 311VH_: | VQLEESGGDLVKPGASLTLTCTASGIDLSRY_YYICWVRQAF |
|   | 317VH_: | __QLEESGGDLVKPGASLTLTCTASGIDLSRY_YYMCWVRQAF |
|   | 402VH_: | _____ESGGGLVKPGASLTLTCKASGIDLSR__YYWICWVRQA |
|   | 14VH__: | QEQLKETGGGLVQPGGSLTLTCKASGFDFSR__YWMSWVRQAF |
|   | 48_433: | _QSLEESGGDLVKPGASLTLTCTASEIDFSRY_YWICWVRQAF |
|   | 25VH__: | _QSVEESGGRLVTPGTPLTLTCTASGFSLSH__YYIGWVRQTF |

FIG. 1A-1

KEY: | FIG. 1A-1 | FIG. 1A-2 | FIG. 1A-3 |

| | ========CDR2======= | 7 | 8 |
|---|---|---|---|
| GKGLEWIGLIS | SSGSINYASWAKGRFTISKT | SSTTVDLKMTSLTTE | |
| GKGLELIGCISS | SDGRTWSTTWARGRFTISKT | STTVDLKVTSLTAA | |
| GKGLEWIGFID | VYNHAYYASWARSRSTITRNTNLNTVTLKMTSLSAA | | |
| GKELEWIGFID | LYGSAYYATWAKGRSTITRNTNLNTVTLQMTSLTAA | | |
| GKGLEWIGSIG | NSGRSYYMTWAKSRATITRNTNLNTVTLRMTSLTAA | | |
| GKGLEYISYIS | DYGVRYYASWVKGRFTISKT | STTVDLKMTSLTTE | |
| GKGLEYIAYIS | DYAVKYYASWAKGRFTISKT | STTVDLKITSLTTE | |
| GKGLEYISYIS | DWGIKYYASWVKGRFTISKT | | |

FIG. 1A-2

|  9    =======CDR3========    11 |
|---|
| DTAAYFCARGWYEFN           VWGPGTLVTVSS |
| DTATYFCARYIDISH           SNLWGPGTLVTVSS |
| DTATYFCARDGGSAG           FNIWGPGTLVTVSS |
| DTATYFCATDGGSSG           FNIWGPGTLVTVSS |
| DTATYFCARWAISDD           AFNIWGPGTLVTVSS |
| DTATYFCARGAPGAG           DNDIWGRGTLVTVSS |
| DTATYFCARGAPGAG           DNDIWGRGTLVTVSS |
| DTATYFCARGAPGAG           DNGIWGRGTLVTVSS |
| DTATYFCARGAPGAG           DNGIWGRGTLVTVSS |
| DTATYFCARGAPGAG           DNGIWGRGTLVTVSS |
| DTATYFCARGGVYNI           GLNIWGPGTLVTVSS |
| DTATYFCARGGLYNS           GLNIWGPGTLVTVSS |
| DTATYFCARGGVYNS           GLNIWGPGTLVTVSS |
| DTATYFCARLGYADY           AYDLWGPGTLVTVSS |
| DTATYFCARGSPGNG           DNDIWGPGTLVTVSS |
| DTATYFCARIRAGASM          YFSLWGPGTLVTVSS |
| DTATYFCARGVSSNGY          YFKLWGPGTLVTVSS |
| DTATYFCARAFGADIG          LYNIWGPGTLVTVSS |
| DTATYFCARDRAGDSL          DFDPWGPGTLVTVSS |
| DTATYFCARGTGYGDY          GFVFWGPGTLVTVSS |
| DTATYFCARDPYGFVY          DFTLWGPGTLVTVSS |
| DTATYFCTRSIYIYGY          AGYLWGPGTLVTVSS |
| DTATYFCASAGTYYNI          DFRLWGPGTLVTVSS |
| DTGTYFCASSVAYTGIY         YFNIWGPGTLVTVSS |
| DTATYFCASSVEYTDLY         YLNIWGPGTLVTVSS |
| DTATYFCARFYAGVSYT         TLDLWGQGTLVTVSS |
| DTATYFCARFAAGYSYT         TLDLWGQGTLVTVSS |
| DTATYFCARDADGDGGW         VFNLWGPGTLVTVSS |
| DTATYFCARGEEFNNGWG        AFNIWGPGTLVTVSS |
| DTATYFCARGEVFNNGWG        AFNIWGPGTLVTVSS |
| DTATYFCARGELFNNGWG        AFNIWGPGTLVTVSS |
| DTATYFCARGELFNNGWG        AFNIWGPGTLVTVSS |
| DTATYFCARDNYDEYDNN        VFDLWSPGTLVTVSS |
| DTATYFCVREAGGQTAYY        GLAPWGPGTLVTVSS |
| DTATYFCASDPVYSSSSG        YLNLWGPGTLVTVSS |
| DTAIYFCARGGPDDSNSMG       TFDPWGPGTLVTVSS |
| DTATYFCATADGGGSDYYW       GFNLWGPGTLVTVSS |
| DTATYFCARAGYDIRSSAY       VPKLWGPGTLVTVSS |
| DTATYFCARGVGSGSAIYMGA     YFDLWGPGTLVTVSS |
| DAATYFCARGYGSASAIYMGA     YFDSWGPGTLVTVSS |
| DTATYFCARGYGSGSNIYMGA     YFDLWGPGTLVTVSS |
| DTATYFCARGYAGYGGYGRPV     NFNLWGPGTLVTVSS |
| DTATYFCARGFGSSSNYYIGI     YFNLWGPGTLVTVSS |
| DTATYFCARYGYDTYGDTYSFS    RLDLWGQGTLVTVSS |

FIG. 1A-3

|   |           | 1                  2     ===CDR1========== |       |
|---|-----------|---------------------------------------------|-------|
|   | 246VK_ :  | _QVLTQTPSPVSAAVGGTVTINCQSSQSVDSD            | VCLA  |
|   | 325VK_ :  | _LVMTQTPASVEAAVGGTVTIKCQASQNIY              | YKLA  |
| A | 818VK_ :  | EVVMTQTPASVSAAVGDTVTIKCQASQSIY              | NYLS  |
|   | 830VK_ :  | EVVMTQTPASVEAAVGGTVTIKCQASQSIY              | SYLS  |
|   | 876VK_ :  | VVLTQTASPMSEPVGGTVTIKCQASQSIG               | SNLA  |
|   | 703VK_ :  | DPVMTQTPSSTSASVGGTVTINCQSTESVYKN            | NYLA  |
|   | 710VK_ :  | DPVMTQTPSSTSAAVGGTVTINCQSTESVYKN            | NYLA  |
| B | 715VK  :  | DPVMTQTPSSTSAAVGGTVTINCQSTESVYKN            | NYLA  |
|   | 825VK_ :  | DPVMTQTPSSTSAAVGGTVTINCQSTESVYKN            | NYLA  |
|   | 867VK_ :  | DPVMTQTPSSTSASVGGTVTINCQSTESVYKN            | NYLA  |
|   | 52VK__ :  | DIVMTQTPASASEPVGGTVTINCQASQNIY              | NTLA  |
| C | 63VK_  :  | DIVMTQTPASASEPVGGTVTINCQASQNIY              | NTLA  |
|   | 115VK_ :  | DIVMTQTPASASEPVGGTVTINCQASQNIY              | STLA  |
|   | 473VK_ :  | _QVLTQTPSPVSATLGGTVTINCQSSQSVYGN            | I     |

FIG. 1B-1

```
           4         ==CDR2=    6            7
WYQQKPGQPPKLLIYRASKLASGVSARFSGSGSGTQFTLTISDV
WYQQKPGQPPKLLIYDASDLASGVPSRFKGSGSGTEFTLTISGV
WYQQKPGQPPKLLMYISSNLASGVPSRFKGSGSGTEYTLTISDL
WYQQKPGQPPKLLFYKTSTLASGVPSRFKGSGSGTEYTLTISDL
WYQQKPGQPPKLLIYKASTLASGVPSRFSGSRSGTEFTLTISDL
WYQQKPGQPPKQLIYDASTLASGVPSRFKGSGSGTQFTLTISGM
WYQQKAGQPPKQLIYDASSLASGVPSRFKGSGSGTQFTLTISGV
WYQQKPGQPPKQLIYDASTLASGVPSRFKGSGSGTNFTLTISGV
WYQQKPGQPPKLLIYDASTLASGVPSRFKASGSGTQFTLTISGV
WYQQKPGQPPKQLIYDASTLNSGVPSRFKGSGSGTQFTLTISGV
WYQQKPGQPPKLLMSLASTLESGVPSRFKGSGSGTEFTLTISDL
WYQQKPGQPPKLLIYVASTLESGVPSRFKGSGSGTQFSLTISDL
WYQQKPGQPPKLLIYLASTLESGVPSRFKGSGSGTEFTLTISDL
WYQQKSGQAPKLLIYQASKLASGVPSRFSGSGSGTQFSLTISGV
WYQQKPGQPPKQLIYSISTLASGVPPRFSGSGSGTEFTLTISDV
WYQQKPGQPPKLLIYEASKLASGVPPRFKGSGAGTQFTLTISGV
WYQQKPGQPPKLLIVAASKLASGVSSRFKGSGSGTEFTLTISGV
WYQQKSGQPPKPLIYEASTLASGVPSRFKGSGYGTEFTLTISDL
WYQQKPGQRPKLLIYGASTLASGVSSRFKGSGSGTEFTLTISGV
WYQQKPGQPPKLLIYRASTLASGVPSRFKGSGSGTEFTLTISDL
WFQQKLGQPPKLLIYRASTLASGVPSRFKGSGSGTQFTLTISGV
WYQQKPGQPPKLLIYLASTLASGVPPRFKGSGSGTEFTLTISDL
WYQQKPGQPPKLLIYDASTLESGVPSRFSGSGSGTEFTLTIRGV
WYQQKPGQPPKLLIYDASNLETGVPSRFKGSGSGTQFTLTISGV
WYQQKPGQPPKQLIYDASTLQSGVPSRFKGSGSGTQFTLTISGV
WYQQKPGQPPKLLIYETSTLASGVSSRFRGSGSGTQFTLTISGV
WYQQKPGQPPKLLIYETSTLASGVSSRFKGSGSGTQFTLTISGV
WYQQKSGQPPKLLMYLASTLASGVPSRFKGSGSGTEFTLTISGV
WYQQKPGQPPKLLIYSASTLASGVPSRFKGSGSGTEFTLTISDL
WYQQKPGQPPKLLIYQASTLASGVSSRFKGSGSGTDFTLAISDL
WYQQKPGQPPKLLIYSASTLASGVSSRFKGSGSGTEFTLTISDL
WYQQKPGQPPKLLIYSASTLASGVSSRFKGSGSGTEFTLTISGV
WYQQKPGQRPKLLIYGASNLESGVPSRFKGSGSGTEYTLTISGV
WYQQKPGQPPKRLIYGASNLASGVPSRFKGSGSGTQFTLTISDL
WYQQKPGQPPKLLIYRASTLASGVPSRFKGSGSGTQFTLTISDL
WYQQKPGQRPKLLIYGASRLASGFPSRFSGSGSGTQFTLTISGV
WYQQKPGQRPKLLIYEASILASGVPSRFKGSGSGTQFTLTISDL
WYQQKPGQPPKLLIYDASTLPSGVPSRFKGSGSGTQFTLTISDL
WYQQKPGQPPKLLIYRASTLASGVSSRFKGSGSGTDYTLTISDL
WYQQKPGQPPKLLIYRASTLTSGVSSRFKGSGSGTEFTLTISDL
WYQQKPGQPPKLLIYRASTLASGVSSRFKGSGSGTQFTLTISDL
WYQQKPGQPPTLLIYAASYLASGVPSRFKGSGSGTEYTLTISGV
WYQQKPGQPPKLLIYSASKLASGVPSRFSGSRSGTEFTLTINDL
WYQQKPGQPPKLLIYEASTLASGVSSRFKGSGSGTQFTLTISGV
```

FIG. 1B-2

```
  8        =====CDR3===== 10
QCDDAATYYCQGIYTGSTWYR_NAFGGGTEVVVK
QCDDAATYYCQQGFSTNEID__NTFGGGTEVVVK
ECDDAATYYCQTNYFISATSPGRAFGGGTEVVVK
ECADAATYYCQTNYFRTSSDPGRAFGGGTEVVVK
ECADAATYYCQGYYYSDSTDS_FVFGGGTEVVVK
QCDDAATYYCAGYWRSGYGTANGSFGGGTEVVVE
QCADAATYYCAGYFRSGSGTANGSFGGGTEVVVK
QCDDAATYYCAGYYRSGFGTANGSFGEGTEVVVK
QCDDAATYYCAGYYRSGSGTANGSFGGGTEVVVK
QCDDAATYYCAGYWYSGSGTANGSFGGGTEVVVK
ECADAATYYCQSNHGSNSDSYGNTFGGGTEVVVK
ECADAATYYCQSNHGSNSNSYGNTFGGGTEVVVK
ECADAATYYCQSNHGSNSNSYGNTFGGGTEVVVK
QCDDAATYYCQGNFNTGDR___YAFGGGTEVVVK
VCDDAATYYCAGYTRGKGDN__SAFGGGTEVVVK
QCDDAATYYCQGEFSCSSADC_IGFGGGTEVVVK
ECADAATYYCQQGWSHTNVD__NTFGGGTEVVVK
ECADAATYYCQQGFSSSNVD__NFFGGGTEVVVK
ECADAATYYCQQSHSTSNID__NAFGGGTEVVVK
ECAAAATYYCQAYYYSSSSNYGNVFGGGTEVVVN
ECDDAATYFCAGYKNWLSDD__HGFGGGTEVVVR
ECDDAATYYCQKNYDSGSGNFFNAFGGGTEVVVK
QCADAATYYCQSYHDGSGTT__FSFGGGTEVVVE
QCADAATYYCLGVYAYSSDDG_AAFGGGTEVVVK
QCDDAATYYCLGVYGYSSDDG_AAFGGGTEVVVK
QCDDAATYYCQGEFSCSSGDC_SAFGGGTEVVVK
QCDDAATYYCQGEFSCSSGDC_SAFGGGTEVVVK
QCADAATYYCQYTDPGSGDD__SPFGGGTEVVVK
ECADAASYYCQQGFATSNVE__NPFGGGTEVVVK
ECADAATYYCQQGFGTSNVE__NPFGGGSEVVVK
ECADAATYYCQQGFGTSNVE__NPFGGGTEVVVK
QCEDAATYYCQQGFGTNNVE__NPFGGGTEVVVK
QCDDAATYYCQQGHSISDVD__NLFGGGTEVVVK
ECDDAATYYCQGYVKEHQ____YPFGGGTEVVVK
ECADAATYYCQSFYYSGSNSYGYAFGGGTEVVVK
ECADAATYYCQQGWSDSYVD__NLFGGGTEVVVK
ECDDAATYYCQNNVAILG____TAFGGGTEVVVN
ECADAATYYCQSYYSSHSTTYWAFGGGTEVVVK
ECADAATYYCQSYYYDLTING_NPFGGGTEVVVI
ECADAATYYCQSYYYDGTTNG_NPFGGGTEVVVK
ECADAATYYCQSYYYDTTTPG_NAFGGGTEVVVS
QCADAATYYCQSAYYASSGDT_WAFGGGTEVVVR
ECADAATYYCQNYYYDSNGGD_NAFGGGTEVVVQ
QCDDAATYYCQGEFSDSSGDC_NAFGGGTEVVVK
```

FIG. 1B-3

| pos | | FREQ. | | | | | | | | | | | | | | | | | | | | | | | KabFrq |
|---|---|---|---|---|---|---|---|---|---|---|---|---|---|---|---|---|---|---|---|---|---|---|---|---|---|
| 1 | | D | 12 | E | 3 | A | | | | | | | | | | | | | | | | | | | DA |
| 2 | | V | 9 | Y | 8 | I | Q | 7 | P | 5 | F | 4 | L | 4 | | | | | | | | | | | IV |
| 3 | | V | 30 | D | 9 | E | | | | | | | | | | | | | | | | | | | V |
| 4 | | M | 30 | L | 14 | | | | | | | | | | | | | | | | | | | | ML |
| 5 | | T | 44 | | | | | | | | | | | | | | | | | | | | | | T |
| 6 | | Q | 44 | | | | | | | | | | | | | | | | | | | | | | Q |
| 7 | | T | 44 | | | | | | | | | | | | | | | | | | | | | | T |
| 8 | | P | 41 | A | 2 | V | | | | | | | | | | | | | | | | | | | P |
| 9 | | S | 25 | A | 18 | F | | | | | | | | | | | | | | | | | | | SA |
| 10 | | S | 33 | P | 11 | | | | | | | | | | | | | | | | | | | | SP |
| 11 | | V | 32 | T | 7 | A | K | 1 | M | 1 | | | | | | | | | | | | | | | V |
| 12 | | S | 33 | E | 11 | | | | | | | | | | | | | | | | | | | | SE |
| 13 | | A | 25 | E | 11 | V | G | 4 | | | | | | | | | | | | | | | | | A |
| 14 | | A | 29 | P | 11 | S | V | 1 | T | 1 | | | | | | | | | | | | | | | AP |
| 15 | | V | 42 | A | 1 | L | | | | | | | | | | | | | | | | | | | V |
| 16 | | G | 44 | | | | | | | | | | | | | | | | | | | | | | | G |
| 17 | | G | 41 | D | 3 | | | | | | | | | | | | | | | | | | | | G |
| 18 | | T | 44 | | | | | | | | | | | | | | | | | | | | | | | T |
| 19 | | V | 44 | | | | | | | | | | | | | | | | | | | | | | | V |
| 20 | | T | 43 | A | 1 | | | | | | | | | | | | | | | | | | | | T |
| 21 | | I | 44 | | | | | | | | | | | | | | | | | | | | | | | I |
| 22 | | K | 22 | N | 20 | H | S | 1 | | | | | | | | | | | | | | | | | KN |
| 23 | | C | 44 | | | | | | | | | | | | | | | | | | | | | | | C |
| 24 | L1 | Q | 44 | | | | | | | | | | | | | | | | | | | | | | | Q |
| 25 | L1 | A | 35 | S | 8 | C | | | | | | | | | | | | | | | | | | | | A |
| 26 | L1 | S | 38 | T | 6 | | | | | | | | | | | | | | | | | | | | | S |
| 27 | L1 | Q | 27 | E | 15 | D | | | | | | | | | | | | | | | | | | | | QE |
| 28 | L1 | S | 27 | N | 14 | R | K | 1 | T | 1 | | | | | | | | | | | | | | | | S |
| 29 | L1 | I | 29 | V | 14 | L | | | | | | | | | | | | | | | | | | | | IV |
| 30 | L1 | Y | 30 | S | 4 | G | V | 2 | F | 1 | D | 1 | N | 1 | A | 1 | | | | | | | | | | YG |
| a | L1 | K | 5 | N | 4 | S | G | 1 | | | | | | | | | | | | | | | | | | |
| b | L1 | N | 12 | K | 1 | D | | | | | | | | | | | | | | | | | | | | N |
| c | L1 | | | | | | | | | | | | | | | | | | | | | | | | | |
| d | L1 | | | | | | | | | | | | | | | | | | | | | | | | | |
| e | L1 | | | | | | | | | | | | | | | | | | | | | | | | | |
| f | L1 | | | | | | | | | | | | | | | | | | | | | | | | | |
| 31 | L1 | S | 18 | N | 16 | K | T | 2 | D | 2 | R | 1 | Y | 1 | I | 1 | V | 1 | | | | | | | | NS |
| 32 | L1 | Y | 8 | N | 7 | L | S | 4 | R | 3 | D | 3 | T | 3 | E | 3 | G | 3 | W | 2 | H | 1 | C | 1 | K | 1 | A | 1 | Y |
| 33 | L1 | L | 43 | M | 1 | | | | | | | | | | | | | | | | | | | | | L |

FIG. 2A page 1 of 3

| Pos | Tag | AA | # | AA | # | AA | # | AA | # | AA | # | AA | # | AA | # | AA | # | AA | # | AA | # | AA | # | Cons |
|---|---|---|---|---|---|---|---|---|---|---|---|---|---|---|---|---|---|---|---|---|---|---|---|---|
| 34 | L1 | A | 38 | S | 6 | | | | | | | | | | | | | | | | | | | AS |
| 35 | | W | 44 | | | | | | | | | | | | | | | | | | | | | W |
| 36 | | Y | 43 | F | 1 | | | | | | | | | | | | | | | | | | | Y |
| 37 | | Q | 44 | | | | | | | | | | | | | | | | | | | | | Q |
| 38 | | Q | 44 | | | | | | | | | | | | | | | | | | | | | Q |
| 39 | | K | 44 | | | | | | | | | | | | | | | | | | | | | K |
| 40 | | P | 39 | S | 3 | A | 1 | L | 1 | | | | | | | | | | | | | | | P |
| 41 | | G | 44 | | | | | | | | | | | | | | | | | | | | | G |
| 42 | | Q | 44 | | | | | | | | | | | | | | | | | | | | | Q |
| 43 | | P | 39 | R | 4 | A | 1 | | | | | | | | | | | | | | | | | P |
| 44 | | P | 44 | | | | | | | | | | | | | | | | | | | | | P |
| 45 | | K | 43 | T | 1 | | | | | | | | | | | | | | | | | | | K |
| 46 | | L | 36 | Q | 6 | P | 1 | R | 1 | | | | | | | | | | | | | | | L |
| 47 | | L | 44 | | | | | | | | | | | | | | | | | | | | | L |
| 48 | | I | 40 | M | 3 | F | 1 | | | | | | | | | | | | | | | | | I |
| 49 | | Y | 42 | V | 1 | S | 1 | | | | | | | | | | | | | | | | | Y |
| 50 | L2 | D | 10 | R | 7 | E | 6 | S | 5 | G | 4 | L | 4 | A | 2 | Q | 2 | K | 2 | I | 1 | V | 1 | KR |
| 51 | L2 | A | 39 | T | 3 | I | 1 | S | 1 | | | | | | | | | | | | | | | A |
| 52 | L2 | S | 44 | | | | | | | | | | | | | | | | | | | | | S |
| 53 | L2 | T | 30 | K | 5 | N | 4 | S | 1 | D | 1 | I | 1 | Y | 1 | R | 1 | | | | | | | T |
| 54 | L2 | L | 44 | | | | | | | | | | | | | | | | | | | | | L |
| 55 | L2 | A | 34 | E | 6 | Q | 1 | P | 1 | T | 1 | N | 1 | | | | | | | | | | | A |
| 56 | L2 | S | 43 | T | 1 | | | | | | | | | | | | | | | | | | | S |
| 57 | | G | 44 | | | | | | | | | | | | | | | | | | | | | G |
| 58 | | V | 43 | F | 1 | | | | | | | | | | | | | | | | | | | V |
| 59 | | P | 32 | S | 12 | | | | | | | | | | | | | | | | | | | PS |
| 60 | | S | 40 | P | 3 | A | 1 | | | | | | | | | | | | | | | | | S |
| 61 | | R | 44 | | | | | | | | | | | | | | | | | | | | | R |
| 62 | | F | 44 | | | | | | | | | | | | | | | | | | | | | F |
| 63 | | K | 36 | S | 7 | R | 1 | | | | | | | | | | | | | | | | | K |
| 64 | | G | 43 | A | 1 | | | | | | | | | | | | | | | | | | | G |
| 65 | | S | 44 | | | | | | | | | | | | | | | | | | | | | S |
| 66 | | G | 42 | R | 2 | | | | | | | | | | | | | | | | | | | G |
| 67 | | S | 42 | Y | 1 | A | 1 | | | | | | | | | | | | | | | | | S |
| 68 | | G | 44 | | | | | | | | | | | | | | | | | | | | | G |
| 69 | | T | 44 | | | | | | | | | | | | | | | | | | | | | T |
| 70 | | E | 21 | Q | 20 | D | 2 | N | 1 | | | | | | | | | | | | | | | EQ |
| 71 | | F | 39 | Y | 5 | | | | | | | | | | | | | | | | | | | F |
| 72 | | T | 42 | S | 2 | | | | | | | | | | | | | | | | | | | T |

FIG. 2A page 2 of 3

```
73    L  44
74    T  43 A  1
75    I  44
76    S  42 N  1 R  1
77    G  22 D 22
78    V  23 L 20 M  1
79    E  24 Q 19 V  1
80    C  44
81    A  24 D 19 E  1
82    D  43 A  1
83    A  44
84    A  44
85    T  43 S  1
86    Y  44
87    Y  43 F  1
88    C  44
```

| Pos | | | | | | | | | | | | | | | | | Consensus |
|---|---|---|---|---|---|---|---|---|---|---|---|---|---|---|---|---|---|
| 89 | L3 | Q 35 | A 7 | L 2 | | | | | | | | | | | | | QL |
| 90 | L3 | G 17 | Q 10 | S 10 | N 2 | T 2 | A 1 | Y 1 | K 1 | | | | | | | | G |
| 91 | L3 | Y 16 | G 9 | N 8 | E 4 | V 2 | A 2 | F 1 | T 1 | I 1 | S 1 | | | | | | G |
| 92 | L3 | Y 17 | F 12 | H 6 | W 4 | V 2 | K 1 | D 1 | T 1 | | | | | | | | Y |
| 93 | L3 | S 10 | Y 10 | G 7 | R 5 | A 3 | D 2 | F 2 | N 2 | P 1 | T 1 | K 1 | | | | | YS |
| 94 | L3 | S 14 | T 7 | D 6 | G 4 | C 3 | I 3 | Y 2 | E 1 | W 1 | H 1 | A 1 | R 1 | | | | S |
| 95 | L3 | S 21 | G 9 | N 5 | L 3 | T 3 | D 1 | H 1 | K 1 | | | | | | | | SG |
| a | L3 | S 19 | N 8 | T 4 | G 4 | Y 2 | D 2 | Q 1 | F 1 | A 1 | H 1 | E 1 | | | | | S |
| b | L3 | G 11 | V 8 | D 6 | T 5 | N 3 | S 3 | I 3 | W 1 | A 1 | R 1 | | | | | | |
| c | L3 | D 17 | T 7 | N 5 | S 5 | E 4 | P 1 | G 1 | Y 1 | | | | | | | | |
| d | L3 | G 5 | A 5 | Y 5 | C 4 | P 2 | T 2 | R 1 | F 1 | S 1 | D 1 | | | | | | |
| e | L3 | G 7 | N 5 | F 1 | Y 1 | | | | | | | | | | | | |
| 96 | L3 | N 21 | G 5 | S 4 | Y 3 | W 2 | F 2 | A 2 | R 2 | H 1 | T 1 | I 1 | | | | | AV |
| 97 | L3 | A 18 | P 8 | S 6 | T 5 | V 2 | G 2 | L 2 | F 1 | | | | | | | | |

```
98    F  44
99    G  44
100   G  43 E  1
101   G  44
102   T  43 S  1
103   E  44
104   V  44
105   V  44
106   V  44
107   K  35 N  2 R  2 E  2 S  1 I  1 Q  1
```

Right column (positions 98–107): F, G, G, G, T, E, V, V, V, K

FIG. 2A page 3 of 3

```
pos FREQ.                                           KabFrq
1       D  12 E   3 A  1                            DA
2       V   9 Y   8 I   7 Q  7 P  5 F  4 L  4       IV
3       V  30 D   9 E   5                           V
4       M  30 L  14                                 ML
5       T  44                                       T
6       Q  44                                       Q
7       T  44                                       T
8       P  41 A   2 V   1                           P
9       S  25 A  18 F   1                           SA
10      S  33 P  11                                 SP
11      V  32 T   7 A   3 K  1 M  1                 V
12      S  33 E  11                                 SE
13      A  25 E  11 V   4 G  4                      A
14      A  29 P  11 S   2 V  1 T  1                 AP
15      V  42 A   1 L   1                           V
16      G  44                                       G
17      G  41 D   3                                 G
18      T  44                                       T
19      V  44                                       V
20      T  43 A   1                                 T
21      I  44                                       I
22      K  22 N  20 H   1 S  1                      KN
23      C  44                                       C
```

| 24 | L1 | Q | 44 |   |   |   |   |   |   |   |   |   |   |   |   |   |   |   |   |   |   |   |   | Q  |
|----|----|---|----|---|---|---|---|---|---|---|---|---|---|---|---|---|---|---|---|---|---|---|---|----|
| 25 | L1 | A | 35 | S | 8 | C | 1 |   |   |   |   |   |   |   |   |   |   |   |   |   |   |   |   | A  |
| 26 | L1 | S | 38 | T | 6 |   |   |   |   |   |   |   |   |   |   |   |   |   |   |   |   |   |   | S  |
| 27 | L1 | Q | 27 | E | 15| D | 2 |   |   |   |   |   |   |   |   |   |   |   |   |   |   |   |   | QE |
| 28 | L1 | S | 27 | N | 14| R | 1 | K | 1 | T | 1 |   |   |   |   |   |   |   |   |   |   |   |   | S  |
| 29 | L1 | I | 29 | V | 14| L | 1 |   |   |   |   |   |   |   |   |   |   |   |   |   |   |   |   | IV |
| 30 | L1 | Y | 30 | S | 4 | G | 4 | V | 2 | F | 1 | D | 1 | N | 1 | A | 1 |   |   |   |   |   |   | YG |
| a  | L1 | K | 5  | N | 4 | S | 4 | G | 1 |   |   |   |   |   |   |   |   |   |   |   |   |   |   |    |
| b  | L1 | N | 12 | K | 1 | D | 1 |   |   |   |   |   |   |   |   |   |   |   |   |   |   |   |   | N  |
| c  | L1 |   |    |   |   |   |   |   |   |   |   |   |   |   |   |   |   |   |   |   |   |   |   |    |
| d  | L1 |   |    |   |   |   |   |   |   |   |   |   |   |   |   |   |   |   |   |   |   |   |   |    |
| e  | L1 |   |    |   |   |   |   |   |   |   |   |   |   |   |   |   |   |   |   |   |   |   |   |    |
| f  | L1 |   |    |   |   |   |   |   |   |   |   |   |   |   |   |   |   |   |   |   |   |   |   |    |
| 31 | L1 | S | 18 | N | 16| K | 2 | T | 2 | D | 2 | R | 1 | Y | 1 | I | 1 | V | 1 |   |   |   |   | NS |
| 32 | L1 | Y | 8  | N | 7 | L | 4 | S | 4 | R | 3 | D | 3 | T | 3 | E | 3 | G | 3 | W | 2 | H | 1 | C | 1 | K | 1 | A | 1 | Y  |
| 33 | L1 | L | 43 | M | 1 |   |   |   |   |   |   |   |   |   |   |   |   |   |   |   |   |   |   | L  |

FIG. 2B page 1 of 3

| 34 | L1 | A | 38 | S | 6 | | | | | | | | | | | | | | | | | | AS |
|---|---|---|---|---|---|---|---|---|---|---|---|---|---|---|---|---|---|---|---|---|---|---|---|
| 35 | | W | 44 | | | | | | | | | | | | | | | | | | | | W |
| 36 | | Y | 43 | F | 1 | | | | | | | | | | | | | | | | | | Y |
| 37 | | Q | 44 | | | | | | | | | | | | | | | | | | | | Q |
| 38 | | Q | 44 | | | | | | | | | | | | | | | | | | | | Q |
| 39 | | K | 44 | | | | | | | | | | | | | | | | | | | | K |
| 40 | | P | 39 | S | 3 | A | 1 | L | 1 | | | | | | | | | | | | | | P |
| 41 | | G | 44 | | | | | | | | | | | | | | | | | | | | G |
| 42 | | Q | 44 | | | | | | | | | | | | | | | | | | | | Q |
| 43 | | P | 39 | R | 4 | A | 1 | | | | | | | | | | | | | | | | P |
| 44 | | P | 44 | | | | | | | | | | | | | | | | | | | | P |
| 45 | | K | 43 | T | 1 | | | | | | | | | | | | | | | | | | K |
| 46 | | L | 36 | Q | 6 | P | 1 | R | 1 | | | | | | | | | | | | | | L |
| 47 | | L | 44 | | | | | | | | | | | | | | | | | | | | L |
| 48 | | I | 40 | M | 3 | F | 1 | | | | | | | | | | | | | | | | I |
| 49 | | Y | 42 | V | 1 | S | 1 | | | | | | | | | | | | | | | | Y |
| 50 | L2 | D | 10 | R | 7 | E | 6 | S | 5 | G | 4 | L | 4 | A | 2 | Q | 2 | K | 2 | I | 1 | V | 1 | KR |
| 51 | L2 | A | 39 | T | 3 | I | 1 | S | 1 | | | | | | | | | | | | | | A |
| 52 | L2 | S | 44 | | | | | | | | | | | | | | | | | | | | S |
| 53 | L2 | T | 30 | K | 5 | N | 4 | S | 1 | D | 1 | I | 1 | Y | 1 | R | 1 | | | | | | T |
| 54 | L2 | L | 44 | | | | | | | | | | | | | | | | | | | | L |
| 55 | L2 | A | 34 | E | 6 | Q | 1 | P | 1 | T | 1 | N | 1 | | | | | | | | | | A |
| 56 | L2 | S | 43 | T | 1 | | | | | | | | | | | | | | | | | | S |
| 57 | | G | 44 | | | | | | | | | | | | | | | | | | | | G |
| 58 | | V | 43 | F | 1 | | | | | | | | | | | | | | | | | | V |
| 59 | | P | 32 | S | 12 | | | | | | | | | | | | | | | | | | PS |
| 60 | | S | 40 | P | 3 | A | 1 | | | | | | | | | | | | | | | | S |
| 61 | | R | 44 | | | | | | | | | | | | | | | | | | | | R |
| 62 | | F | 44 | | | | | | | | | | | | | | | | | | | | F |
| 63 | | K | 36 | S | 7 | R | 1 | | | | | | | | | | | | | | | | K |
| 64 | | G | 43 | A | 1 | | | | | | | | | | | | | | | | | | G |
| 65 | | S | 44 | | | | | | | | | | | | | | | | | | | | S |
| 66 | | G | 42 | R | 2 | | | | | | | | | | | | | | | | | | G |
| 67 | | S | 42 | Y | 1 | A | 1 | | | | | | | | | | | | | | | | S |
| 68 | | G | 44 | | | | | | | | | | | | | | | | | | | | G |
| 69 | | T | 44 | | | | | | | | | | | | | | | | | | | | T |
| 70 | | E | 21 | Q | 20 | D | 2 | N | 1 | | | | | | | | | | | | | | EQ |
| 71 | | F | 39 | Y | 5 | | | | | | | | | | | | | | | | | | F |
| 72 | | T | 42 | S | 2 | | | | | | | | | | | | | | | | | | T |

FIG. 2B page 2 of 3

| | | | | | | | | | | | | | | | | | | | | | | |
|---|---|---|---|---|---|---|---|---|---|---|---|---|---|---|---|---|---|---|---|---|---|---|
| 73 | | L | 44 | | | | | | | | | | | | | | | | | | | L |
| 74 | | T | 43 | A | 1 | | | | | | | | | | | | | | | | | T |
| 75 | | I | 44 | | | | | | | | | | | | | | | | | | | I |
| 76 | | S | 42 | N | 1 | R | 1 | | | | | | | | | | | | | | | S |
| 77 | | G | 22 | D | 22 | | | | | | | | | | | | | | | | | GD |
| 78 | | V | 23 | L | 20 | M | 1 | | | | | | | | | | | | | | | VL |
| 79 | | E | 24 | Q | 19 | V | 1 | | | | | | | | | | | | | | | QE |
| 80 | | C | 44 | | | | | | | | | | | | | | | | | | | C |
| 81 | | A | 24 | D | 19 | E | 1 | | | | | | | | | | | | | | | AD |
| 82 | | D | 43 | A | 1 | | | | | | | | | | | | | | | | | D |
| 83 | | A | 44 | | | | | | | | | | | | | | | | | | | A |
| 84 | | A | 44 | | | | | | | | | | | | | | | | | | | A |
| 85 | | T | 43 | S | 1 | | | | | | | | | | | | | | | | | T |
| 86 | | Y | 44 | | | | | | | | | | | | | | | | | | | Y |
| 87 | | Y | 43 | F | 1 | | | | | | | | | | | | | | | | | Y |
| 88 | | C | 44 | | | | | | | | | | | | | | | | | | | C |
| 89 | L3 | Q | 35 | A | 7 | L | 2 | | | | | | | | | | | | | | | QL |
| 90 | L3 | G | 17 | Q | 10 | S | 10 | N | 2 | T | 2 | A | 1 | Y | 1 | K | 1 | | | | | G |
| 91 | L3 | Y | 16 | G | 9 | N | 8 | E | 4 | V | 2 | A | 1 | F | 1 | T | 1 | I | 1 | S | 1 | G |
| 92 | L3 | Y | 17 | F | 12 | H | 6 | W | 4 | V | 2 | K | 1 | D | 1 | T | 1 | | | | | Y |
| 93 | L3 | S | 10 | Y | 10 | G | 7 | R | 5 | A | 3 | D | 2 | F | 2 | N | 2 | P | 1 | T | 1 | K | 1 | YS |
| 94 | L3 | S | 14 | T | 7 | D | 6 | G | 4 | C | 3 | I | 3 | Y | 2 | E | 1 | W | 1 | H | 1 | A | 1 | R | 1 | S |
| 95 | L3 | S | 21 | G | 9 | N | 5 | L | 3 | T | 3 | D | 1 | H | 1 | K | 1 | | | | | SG |
| a | L3 | S | 19 | N | 8 | T | 4 | G | 4 | Y | 2 | D | 2 | Q | 1 | F | 1 | A | 1 | H | 1 | E | 1 | S |
| b | L3 | G | 11 | V | 8 | D | 6 | T | 5 | N | 3 | S | 3 | I | 3 | W | 1 | A | 1 | R | 1 | | |
| c | L3 | D | 17 | T | 7 | N | 5 | S | 5 | E | 4 | P | 1 | G | 1 | Y | 1 | | | | | | |
| d | L3 | G | 5 | A | 5 | Y | 5 | C | 4 | P | 2 | T | 2 | R | 1 | F | 1 | S | 1 | D | 1 | | |
| e | L3 | G | 7 | N | 5 | F | 1 | Y | 1 | | | | | | | | | | | | | | |
| 96 | L3 | N | 21 | G | 5 | S | 4 | Y | 3 | W | 2 | F | 2 | A | 2 | R | 2 | H | 1 | T | 1 | I | 1 | |
| 97 | L3 | A | 18 | P | 8 | S | 6 | T | 5 | V | 2 | G | 2 | L | 2 | F | 1 | | | | | AV |
| 98 | | F | 44 | | | | | | | | | | | | | | | | | | | F |
| 99 | | G | 44 | | | | | | | | | | | | | | | | | | | G |
| 100 | | G | 43 | E | 1 | | | | | | | | | | | | | | | | | G |
| 101 | | G | 44 | | | | | | | | | | | | | | | | | | | G |
| 102 | | T | 43 | S | 1 | | | | | | | | | | | | | | | | | T |
| 103 | | E | 44 | | | | | | | | | | | | | | | | | | | E |
| 104 | | V | 44 | | | | | | | | | | | | | | | | | | | V |
| 105 | | V | 44 | | | | | | | | | | | | | | | | | | | V |
| 106 | | V | 44 | | | | | | | | | | | | | | | | | | | V |
| 107 | | K | 35 | N | 2 | R | 2 | E | 2 | S | 1 | I | 1 | Q | 1 | | | | | | | K |

FIG. 2B page 3 of 3

VH: GROUPS A-G

```
                  1         2        =CDR1==      4
GROUP A
818VH__:_QSVKESEGGLFKPDETLTLTCTVSEIDLSG__NQISWVRQAP
830--_:_-------------A---A------G----R__-S--------
              *       *      *    *   *

GROUP B
703VH_:_QSLEESGGGLVKPGGTLTLTCTVSGIDLSN__DAISWVRQAP
710--_:_------------------------------__---------
715--_:_-----------T------------------R-__---------
825--_:_------------------------------__---------
867--_:_------------------------------__---------
              *                *

GROUP C
52VH__:QEQLKESGGGLVTPGGTLTLTCTASGFTISS__YVMTWVRQAP
63--___:_QSVE----R------S------V---SL--__F--S------
115VH_:_QSVE----R------S------V---SL--__F--S------
       ****     *      *      *   **   * *

GROUP D
1VH __:_QSVKESEGGLFKPTDTLTLTCTVSGISLSS__NEISWVRQAP
204VH :_-----------------------------F--N-__---------
                                   * *

GROUP E
427VH__:_QSLEESGGDLVKPGASLTLTCTASGFTLSS__YYMCWVRQAP
45VH__:_-----------------------------LSF--__---------
                                    ***

GROUP F
101VH_:_QSVKESEGGLFKPTDTLTLTCTVSGFSLSR__YGVSWVRQAP
810_81:_-------------A-------------------__---------
858--_:_------------------------------__--IN------
877--_:_------------------------------__---T------
                  *                      * *

GROUP G
311VH_:_VQLEESGGDLVKPGASLTLTCTASGIDLSRY__YYICWVRQAP
317--_:_------------------------------__--M-------
402--_:_____----G-----------K--------__--WICWVRQA
              *             *              *
```

FIG. 3A-1

KEY: | FIG. 3A-1 | FIG. 3A-2 | FIG. 3A-3 |

```
            ========CDR2========       7            8

GKGLEWIGFID     VYNHAYYASWARSRSTITRNTNLNTVTLKMT
--E--------    ---L-GS----T--KG---------------Q--
  *               *  **    *   **                *

GKGLEYISYIS     DYGVRYYASWVKGRFTISKT  STTVDLKMT
----------A---     ---A-K-----A---------  -------I-
----------        -W-IK---------------  -------I-
----------A---     -WSI----N-AQ--------  -------I-
----------A---     ----------A---------  ---M----I-
       *           * ***   * **             *    *

GKGLEGIGYI     KSGNIWYASWAKGRFTISRT  STTVDLKII
-----A----     --------N-----------  -------MT
-----A----     --------------------  -------MT
     *                  *                    **

GNGLEWIGYVG     NGGMTHYASWAKSRSTITRNTSLKTVTLKMT
---------I-     ------------G------D-N-N-------
         *                   *        * * *

GKGLEWIACIYAA  VNGGTNYASWAKGRFTISKT SSTTVTLQMT
--------G-----    _T--N-E-------------- _----------
       *          *  * *

GSGLQWIGAIG     ETGRAYYANWAKSRSTITRNTVNTVTLKMT
-N--E---T--     -A----------R-------T--L-----T-
-----------     ------F-S--------------L-----R--
-N------T--     ----S---S-------V-----E--------
 * *    *       * *  * *   *       *  *     *

GKGLEWIGCIN    TGVGNGYYASWAKGRIITSKT SSTTVTLQMT
-----------L-  S-S-DTFS-R-----FVIF-- -----D-K--
PGKGLEWIGCINS  -S-YT---N-----F-I---  ----------
                *    ****            * *
```

FIG. 3A-2

```
              9         =======CDR3========         11

SLSAADTATYFCARDGGSAG_____FNIWGPGTLVTVSS
--T----------T----S-_____--------------
  *           *    *

SLTTEDTATYFCARGAPGAG_____DNDIWGRGTLVTVSS
--------------------_____--------------
---I----------------_____--G-----------
--------------------_____--G-----------
--------------------_____--G-----------
  *                                *

SPTIEDTATYFCARGGVYNI_____GLNIWGPGTLVTVSS
-L-T-----------L--S_____--------------
-L-T--------------S_____--------------
 * *           * *

SLTAADTGTYFCASSVAYTGIY_____YFNIWGPGTLVTVSS
-------A--------E--DL-_____-L-------------
       *        *  **           *

SLTAADTATYFCARFYAGVSYT_____TLDLWGQGTLVTVSS
G-------------A--Y---_____--------------
*              *  *

SLTAADTATYFCARGEEFNNGWG_____AFNIWGPGTLVTVSS
--------------V-------_____--------------
--------------L-------_____--------------
--------------L-------_____--------------
              *

SLTAADTATYFCARGVGSGSAIYMGA_____YFDLWGPGTLVTVSS
-------A--------Y--A------_____---S----------
----------------Y----N----_____--------------
       *        *    *
```

FIG. 3A-3

```
VK: GROUPS A-G 1         2    ===CDR1==========    4
GROUP A
818VK_ :EVVMTQTPASVSAAVGDTVTIKCQASQSIY_____NYLSWYQQKPGQPPKLLMY
830--_ :----------E----G-------------     S--------------F-
              *    *                       *              *

GROUP B
703VK_ :DPVMTQTPSSTSASVGGTVTINCQSTESVYKN____NYLAWYQQKPGQPPKQLIY
710--_ :------------A-------------------   ---------A---------
715--_ :------------A-------------------   -------------------
825--_ :------------A-------------------   ----------------L---
867--_ :--------------------------------   -------------------
                    *                               *    *

GROUP C
52VK__ :DIVMTQTPASASASEPVGGTVTINCQASQNIY____NTLAWYQQKPGQPPKLLMS
63--_  :--------------------------------   -----------------IY
115VK_ :--------------------------------   S----------------IY
                                                       *    **

GROUP D
1VK___ :_LVMTQTPSSTSEPVGGTVTINCQASDNIY_____SGLAWYQQKPGQPPKLLIY
204VK_ :_-----------------------------     R--------------Q---
                                                *            *

GROUP E
427VK_ :_QVLTQTPSPVSAAVGGTVTINCQASQSVYNN____KNLAWYQQKPGQPPKLLIY
45VK__ :_-------------V------A----S-------  NL-----------------
                      *      *    *

GROUP F
101VK_ :_YDMTQTPASVSEPVGGTVTIKCQASENIY_____TSLAWYQQKPGQPPKLLIY
810_81:_-------------------------S--       SG-----------------
858_85:_-----------------------------      S------------------
877--_:_-----------------------------      S------------------
                                 *              **

GROUP G
311VK_ :_FELTQTPSPVSGAVGGTVTINCQASQSIS_____NELAWYQQKPGQPPKLLIY
317--_ :_---------------------K-----N-Y    SD-----------------
402--_ :_--------S-EA---------K-------V    SD-----------------
                  *  **          *     * *  **
```

KEY: | FIG. 3B-1 | FIG. 3B-2 |

FIG. 3B-1

```
==CDR2=    6            7           8           =====CDR3=====  10

ISSNLASGVPSRFKGSGSGTEYTLTISDLECDDAATYYCQTNYFISATSPGRAFGGGTEVVVK
KT-T---------------------A------------RTSSD--------------
 ** *                              *           ****

DASTLASGVPSRFKGSGSGTQFTLTISGMQCDDAATYYCAGYWRSGYGTANGSFGGGTEVVVE
---S---------------------V--A---------F---S--------------K
----------------------N------V-----------Y---F--------E-----K
---------A-------------------V-----------Y---S--------------K
-----N-----------------------V-----------Y--S---------------K
 * *      *          *       * *         ** *         *     *

LASTLESGVPSRFKGSGSGTEFTLTISDLECADAATYYCQSNHGSNSDSYGNTFGGGTEVVVK
V-------------------Q-S-----------------------N--------------
------------------------------------------------N--------------
 *                    * *                     *

DASNLETGVPSRFKGSGSGTQFTLTISGVQCADAATYYCLGVYAYSSDDG_AAFGGGTEVVVK
---T-QS------------------------D----------G------_------------
   * **                        *          *

ETSTLASGVSSRFRGSGSGTQFTLTISGVQCDDAATYYCQGEFSCSSGDC_SAFGGGTEVVVK
-----------K----------------------------------------_------------
           *

SASTLASGVPSRFKGSGSGTEFTLTISDLECADAASYYCQQGFATSNVE__NPFGGGTEVVVK
Q--------S----------D---A-----------T------G-----__------S-----
---------S------------------------T------G-----__-------------
---------S--------------GVQ-E-----T------G-N---__-------------
*        *          *   *** *    *        * *             *

RASTLASGVSSRFKGSGSGTDYTLTISDLECADAATYYCQSYYYDLTING_NPFGGGTEVVVI
-----T--------------EF--------------------G-T--_----------K
---------------------QF-------------------T-TP-_-A---------S
     *              **                    * ** *            *
```

FIG. 3B-2 ically high production and release from cells of TNF-α contributes to
TNFα-NEUTRALIZING ANTIBODIES

INTRODUCTION

Field of the Invention

The field of this invention is antibodies, particularly monoclonal antibodies that neutralize tumor necrosis factor-α (TNFα) activity.

Background of the Invention

The pathology of a variety of disorders is attributed to excessive amounts of TNF-α, either locally or systemically. For example, there is strong evidence that abnormally high production and release from cells of TNF-α contributes to disease initiation and progression in rheumatoid arthritis, systemic inflammatory syndromes, diabetes, and multiple sclerosis. In every one of these conditions, the initiating and sustaining pathophysiologic action is directly a result of an immediate local release and synthesis of massive amounts of TNF-α from several types of cells at or adjacent to the site of tissue damage. The locally released TNF-α is followed by additional synthesis and release of TNF-α by invading macrophages drawn to the site of tissue damage by a cascade of chemotactic cytokines released locally from cells in response to the greatly elevated TNF-α concentrations.

There is a need in the art for methods of treating TNF-α-mediated disorders. The present invention addresses this need.

Literature

Literature of interest includes: published U.S. patent applications 20040151722, 20050037008, 20040185047, 20040138427, 20030187231, 20040002589 and 20030199679 and Balazovich (Blood 1996 88: 690-696).

SUMMARY OF THE INVENTION

The invention provides monoclonal antibodies that neutralize TNFα activity. The monoclonal antibodies may be rabbit monoclonal antibodies or monoclonal antibodies having CDR regions derived from those rabbit monoclonal antibodies. In certain embodiments, the monoclonal antibodies may be humanized. Methods of using the subject antibodies to inhibit TNFα activity, methods of treatment using those antibodies and kits containing the same are also provided. The invention finds use in a variety of research and medical applications.

These and other advantages and features of the invention will become apparent to those persons skilled in the art upon reading the details of the invention as more fully described below.

BRIEF DESCRIPTION OF THE DRAWINGS

FIG. 1A. shows a sequence alignment of the heavy chain amino acid sequences of 44 exemplary rabbit TNFα neutralizing antibodies. Various antibody domains are indicated.

FIG. 1B. shows a sequence alignment of the light chain amino acid sequences of 44 exemplary rabbit TNFα neutralizing antibodies. The light chains set forth in this figure are partnered with corresponding heavy chains in FIG. 1A to provide antibodies that neutralizes TNFα. Various antibody domains are indicated.

FIG. 2A shows the number of times an amino acid is present at each position of the heavy chains set forth in FIG. 1A. The amino acid positions are numbered using standard Kabat numbering, supra. Various antibody domains are indicated.

FIG. 2B shows the number of times an amino acid is present at each position of the light chains set forth in FIG. 1B. The amino acid positions are numbered using standard Kabat numbering. Various antibody domains are indicated.

FIG. 3A shows sequence alignments for heavy chains of each of 7 groups of related antibodies (i.e., antibodies produced by cells having a common naïve B cell ancestor).

FIG. 3B shows sequence alignments for heavy chains of each of 7 groups of related antibodies (i.e., antibodies produced by cells having a common naïve B cell ancestor).

DEFINITIONS

Before the present subject invention is described further, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are now described. All publications mentioned herein are incorporated herein by reference to disclose and describe the methods and/or materials in connection with which the publications are cited.

It must be noted that as used herein and in the appended claims, the singular forms "a", "and", and "the" include plural referents unless the context clearly dictates otherwise. Thus, for example, reference to "an antibody" includes a plurality of such antibodies and reference to "a framework region" includes reference to one or more framework regions and equivalents thereof known to those skilled in the art, and so forth.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

The terms "antibody" and "immunoglobulin" are used interchangeably herein. These terms are well understood by those in the field, and refer to a protein consisting of one or more polypeptides that specifically binds an antigen. One form of antibody constitutes the basic structural unit of an antibody. This form is a tetramer and consists of two identical pairs of antibody chains, each pair having one light and one heavy chain. In each pair, the light and heavy chain variable regions are together responsible for binding to an antigen, and the constant regions are responsible for the antibody effector functions.

The recognized immunoglobulin polypeptides include the kappa and lambda light chains and the alpha, gamma ($IgG_1$, $IgG_2$, $IgG_3$, $IgG_4$), delta, epsilon and mu heavy chains or equivalents in other species. Full-length immunoglobulin "light chains" (of about 25 kDa or about 214 amino acids) comprise a variable region of about 110 amino acids at the NH$_2$-terminus and a kappa or lambda constant region at the COOH-terminus. Full-length immunoglobulin "heavy chains" (of about 50 kDa or about 446 amino acids), similarly comprise a variable region (of about 116 amino acids) and one of the aforementioned heavy chain constant regions, e.g., gamma (of about 330 amino acids).

The terms "antibodies" and "immunoglobulin" include antibodies or immunoglobulins of any isotype, fragments of antibodies which retain specific binding to antigen, including, but not limited to, Fab, Fv, scFv, and Fd fragments, chimeric antibodies, humanized antibodies, single-chain antibodies, and fusion proteins comprising an antigen-binding portion of an antibody and a non-antibody protein. The antibodies may be detectably labeled, e.g., with a radioisotope, an enzyme which generates a detectable product, a fluorescent protein, and the like. The antibodies may be further conjugated to other moieties, such as members of specific binding pairs, e.g., biotin (member of biotin-avidin specific binding pair), and the like. The antibodies may also be bound to a solid support, including, but not limited to, polystyrene plates or beads, and the like. Also encompassed by the term are Fab', Fv, F(ab')$_2$, and or other antibody fragments that retain specific binding to antigen, and monoclonal antibodies.

Antibodies may exist in a variety of other forms including, for example, Fv, Fab, and (Fab')$_2$, as well as bi-functional (i.e. bi-specific) hybrid antibodies (e.g., Lanzavecchia et al., Eur. J. Immunol. 17, 105 (1987)) and in single chains (e.g., Huston et al., Proc. Natl. Acad. Sci. U.S.A., 85, 5879-5883 (1988) and Bird et al., Science, 242, 423-426 (1988), which are incorporated herein by reference). (See, generally, Hood et al., "Immunology", Benjamin, N.Y., 2nd ed. (1984), and Hunkapiller and Hood, Nature, 323, 15-16 (1986).

An immunoglobulin light or heavy chain variable region consists of a "framework" region (FR) interrupted by three hypervariable regions, also called "complementarity determining regions" or "CDRs". The extent of the framework region and CDRs have been precisely defined (see, "Sequences of Proteins of Immunological Interest," E. Kabat et al., U.S. Department of Health and Human Services, (1991)). The numbering of all antibody amino acid sequences discussed herein conforms to the Kabat system. The sequences of the framework regions of different light or heavy chains are relatively conserved within a species. The framework region of an antibody, that is the combined framework regions of the constituent light and heavy chains, serves to position and align the CDRs. The CDRs are primarily responsible for binding to an epitope of an antigen.

Chimeric antibodies are antibodies whose light and heavy chain genes have been constructed, typically by genetic engineering, from antibody variable and constant region genes belonging to different species. For example, the variable segments of the genes from a rabbit monoclonal antibody may be joined to human constant segments, such as gamma 1 and gamma 3. An example of a therapeutic chimeric antibody is a hybrid protein composed of the variable or antigen-binding domain from a rabbit antibody and the constant or effector domain from a human antibody (e.g., the anti-Tac chimeric antibody made by the cells of A.T.C.C. deposit Accession No. CRL 9688), although other mammalian species may be used.

As used herein, the term "humanized antibody" or "humanized immunoglobulin" refers to an non-human (e.g., mouse or rabbit) antibody containing one or more amino acids (in a framework region, a constant region or a CDR, for example) that have been substituted with a correspondingly positioned amino acid from a human antibody. In general, humanized antibodies produce a reduced immune response in a human host, as compared to a non-humanized version of the same antibody.

It is understood that the humanized antibodies designed and produced by the present method may have additional conservative amino acid substitutions which have substantially no effect on antigen binding or other antibody functions. By conservative substitutions is intended combinations such as those from the following groups: gly, ala; val, ile, leu; asp, glu; asn, gln; ser, thr; lys, arg; and phe, tyr. Amino acids that are not present in the same group are "substantially different" amino acids.

The term "specific binding" refers to the ability of an antibody to preferentially bind to a particular analyte that is present in a homogeneous mixture of different analytes. In certain embodiments, a specific binding interaction will discriminate between desirable and undesirable analytes in a sample, in some embodiments more than about 10 to 100-fold or more (e.g., more than about 1000- or 10,000-fold).

In certain embodiments, the affinity between a capture agent and analyte when they are specifically bound in a capture agent/analyte complex is characterized by a $K_D$ (dissociation constant) of less than $10^{-6}$ M, less than $10^{-7}$ M, less than $10^{-8}$ M, less than $10^{-9}$ M, less than $10^{-9}$ M, less than $10^{-11}$ M, or less than about $10^{-12}$ M or less.

An amino acid residue that is in "close contact", "close proximity" or "in close proximity to" another amino acid residue is an amino acid residue that is has a side chain that is close to, i.e., within 7, 6, 5 or 4 Angstroms of, a side chain of another amino acid. For example, an amino acid that are proximal to a CDR is a non-CDR amino acid that has a side chain that is close to a side chain of an amino acid in a CDR.

A "variable region" of a heavy or light antibody chain is an N-terminal mature domain of the chains. All domains, CDRs and residue numbers are assigned on the basis of sequence alignments and structural knowledge. Identification and numbering of framework and CDR residues is as described in by Chothia and others (Chothia, Structural determinants in the sequences of immunoglobulin variable domain. J Mol Biol 1998;278:457-79).

VH is the variable domain of an antibody heavy chain. VL is the variable domain of an antibody light chain, which could be of the kappa (K) or of the lambda isotype. K-1 antibodies have the kappa-1 isotype whereas K-2 antibodies have the kappa-2 isotype and VL is the variable lambda light chain.

A "buried residue" is an amino acid residue whose side chain has less than 50% relative solvent accessibility, which is calculated as the percentage of the solvent accessibility relative to that of the same residue, X, placed in an extended GGXGG peptide. Methods for calculating solvent accessibility are well known in the art (Connolly 1983 J. appl. Crystallogr, 16, 548-558).

As used herein, the terms "determining," "measuring," and "assessing," and "assaying" are used interchangeably and include both quantitative and qualitative determinations.

The terms "polypeptide" and "protein", used interchangeably herein, refer to a polymeric form of amino acids of any length, which can include coded and non-coded amino acids, chemically or biochemically modified or derivatized amino acids, and polypeptides having modified peptide backbones. The term includes fusion proteins, including, but not limited to, fusion proteins with a heterologous amino acid sequence, fusions with heterologous and homologous leader sequences, with or without N-terminal methionine residues; immunologically tagged proteins; fusion proteins with detectable fusion partners, e.g., fusion proteins including as a fusion partner a fluorescent protein, β-galactosidase, luciferase, etc.;

and the like. Polypeptides may be of any size, and the term "peptide" refers to polypeptides that are 8-50 residues (e.g., 8-20 residues) in length.

As used herein the term "isolated," when used in the context of an isolated antibody, refers to an antibody of interest that is at least 60% free, at least 75% free, at least 90% free, at least 95% free, at least 98% free, and even at least 99% free from other components with which the antibody is associated with prior to purification.

The terms "treatment" "treating" and the like are used herein to refer to any treatment of any disease or condition in a mammal, e.g. particularly a human or a mouse, and includes: a) preventing a disease, condition, or symptom of a disease or condition from occurring in a subject which may be predisposed to the disease but has not yet been diagnosed as having it; b) inhibiting a disease, condition, or symptom of a disease or condition, e.g., arresting its development and/or delaying its onset or manifestation in the patient; and/or c) relieving a disease, condition, or symptom of a disease or condition, e.g., causing regression of the condition or disease and/or its symptoms.

The terms "subject," "host," "patient," and "individual" are used interchangeably herein to refer to any mammalian subject for whom diagnosis or therapy is desired, particularly humans. Other subjects may include cattle, dogs, cats, guinea pigs, rabbits, rats, mice, horses, and so on.

"Corresponding amino acids", as will be exemplified below, are amino acid residues that are at an identical position (i.e., they lie across from each other) when two or more amino acid sequences are aligned. Methods for aligning and numbering antibody sequences are set forth in great detail in Chothia, supra, Kabat supra, and others. As is known in the art (see, e.g. Kabat 1991 Sequences of Proteins of Immunological Interest, DHHS, Washington, D.C.), sometimes one, two or three gaps and/or insertions of up to one, two, three or four residues, or up to about 15 residues (particularly in the L3 and H3 CDRs) may be made to one or both of the amino acids of an antibody in order to accomplish an alignment.

A "natural" antibody is an antibody in which the heavy and light immunoglobulins of the antibody have been naturally selected by the immune system of a multi-cellular organism, as opposed to unnaturally paired antibodies made by e.g. phage display, or humanized antibodies. As such, the subject parental antibodies do not usually contain any viral (e.g., bacteriophage M13)-derived sequences. Spleen, lymph nodes and bone marrow are examples of tissues that produce natural antibodies.

A "substitutable position", as will be described in greater detail below, is a particular position of an antibody that may be substituted by different amino acids without significantly decreasing the binding activity of the antibody. Methods for identifying substitutable positions, and how they may be substituted, are described in much greater detail below. A substitutable positions may also be referred to as "variation tolerant position".

A "parent" antibody, as will be described in greater detail below, is an antibody is the target of amino acid substitutions. In certain embodiments, amino acids may be "donated" by a "donor" antibody to the parent antibody to produce an altered antibody.

"Related antibodies", as will be described in greater detail below, are antibodies that have a similar sequence and produced by cells that have a common B cell ancestor. Such a B cell ancestor contains a genome having a rearranged light chain VJC region and a rearranged heavy chain VDJC region, and produces an antibody that has not yet undergone affinity maturation. "Naïve" or "virgin" B cells present in spleen tissue, are exemplary B cell common ancestors. Related antibodies bind to the same epitope of an antigen and are typically very similar in sequence, particularly in their L3 and H3 CDRs. Both the H3 and L3 CDRs of related antibodies have an identical length and a near identical sequence (i.e., differ by 0, 1 or 2 residues). Related antibodies are related via a common antibody ancestor, the antibody produced in the naïve B cell ancestor. The term "related antibodies" is not intended to describe a group of antibodies that do not have a common antibody ancestor produced by a B-cell.

The term "TNFα" or its non-abbreviated form "tumor necrosis factor-α", as used herein, is intended to refer to a human cytokine that exists as a 17 kD secreted form and a 26 kD membrane associated form, the biologically active form of which is composed of a trimer of noncovalently bound 17 kD molecules. The structure of TNFα is described further in, for example, Pennica et al. (Nature 1984 312:724-729), Davis et al. (Biochemistry 1987 26:1322-1326) and Jones et al. (Nature 1989 338:225-228). The term TNFα is intended to include recombinant TNFα molecules, which can be prepared by standard recombinant expression methods or purchased commercially (R & D Systems, Catalog No. 210-TA, Minneapolis, Minn.), as well as fusion proteins containing a TNFα molecule. Amino acid sequences of exemplary TNFαs that may be employed herein are found in the NCBI's Genbank database and a full description of human TNFα and its role in various diseases and conditions is found in NCBI's Online Mendelian Inheritance in Man database.

A "TNFα neutralizing antibody", "antibody that neutralizes TNFα activity" or any grammatical equivalent thereof, is intended to refer to an antibody whose binding to TNFα results in inhibition of a biological activity of TNFα. This inhibition of the biological activity of TNFα can be assessed by measuring one or more indicators of TNFα biological activity, such as TNFα-induced cytotoxicity (either in vitro or in vivo), TNFα-induced cellular activation or TNFα binding to a TNFα receptor. TNFα biological activity can be assessed by one or more of several standard in vitro or in vivo assays known in the art.

DETAILED DESCRIPTION OF PREFERRED EMBODIMENTS

The invention provides monoclonal antibodies that neutralize TNFα activity. The monoclonal antibodies may be rabbit monoclonal antibodies or monoclonal antibodies having CDR regions derived from those rabbit monoclonal antibodies. In certain embodiments, the monoclonal antibodies may be humanized. Methods of using the subject antibodies to inhibit TNFα activity, methods of treatment using those antibodies and kits containing the same are also provided. The invention finds use in a variety of research and medical applications.

Rabbit Monoclonal Antibodies that Neutralize TNFα Activity

In one embodiment, the invention provides rabbit monoclonal antibodies that neutralize TNFα activity, where a rabbit monoclonal antibody is a natural full-length monoclonal rabbit antibody (i.e., an antibody encoded by a rabbit and that that has been naturally selected by the immune system of an immunized rabbit), or any antigen-binding portion thereof (i.e., is an antibody that contains at least all of the framework and complementary determining regions of the full-length antibody).

A TNFα neutralizing rabbit monoclonal antibody of the invention inhibits at least one activity of TNFα in the range of about 20% to 100%, e.g., by at least about 10%, at least about 20%, at least about 30%, at least about 40%, at least about 50%, at least about 60%, usually up to about 70%, up to about 80%, up to about 90% or more. In any of these assays, a subject antibody inhibits TNFα activity with an $IC_{50}$ of $1\times10^{-7}$ M or less (e.g., $1\times10^{-7}$ M or less, $1\times10^{-8}$ M or less, $1\times10^{-9}$ M or less, usually to $1\times10^{-12}$ M or $1\times10^{-13}$ M). In assays in which a mouse is employed, a subject antibody typically has an $ED_{50}$ of less then 1 μg/mouse (e.g., 10 ng/mouse to 1 μg/mouse).

TNFα activity can be assayed in a variety of ways, including, but not limited to: assays for TNFα-induced cytotoxicity (either in vitro or in vivo) using suitable cells, e.g., L929 cells; assays for binding of TNFα to its receptor using suitable cells, e.g., U-937 cells; assays for inhibition of endothelial cell leukocyte adhesion molecule 1 (ELAM-1) expression on human umbilical vein endothelian (HEVEC) cells; or in vivo assays using D-galactosamine sensitized mice. Such assays are described in great detail in U.S. Pat. No. 6,090,382, which is incorporated by reference herein for that purpose.

The subject rabbit monoclonal antibodies have the following general characteristics:
 a) high affinity for TNFα (e.g., a $K_d$ of $10^{-8}$ or less);
 b) slow off rate for dissociation with TNFα (e.g., a $K_{off}$ of $10^{-3}$ $sec^{-1}$ or less); and
 c) TNFα neutralizing activity.

Methods for measuring binding affinity, off rate and other antibody binding kinetics are well known in the art, and may be employed to determine whether an antibody has a high affinity and a slow off rate for TNFα. In many methods and as is well known in the art, antibody binding kinetics may be measured by ELISA methods or by measuring surface plasmon resonance using, for example, a BIACORE™ biosensor sold by Pharmacia (now Pfizer). Methods for measuring binding of antigens to antibodies using surface plasmon resonance are well known in the art (see, e.g., Methods of Dev. Biol. 2003 112:141-51 and J. Mol. Recognit. 1999 12:310-5) and are readily adapted for use herein.

In certain embodiments a subject rabbit monoclonal antibody has a heavy chain that is substantially identical (e.g., at least about 70%, at least about 80%, at least about 90%, at least about 95% or at least about 98% identical) to that of any of the heavy chain variable domain sequences set forth in FIG. 1A, and a light chain that is substantially identical (e.g., at least about 70%, at least about 80%, at least about 90%, at least about 95% or at least about 98% identical) to that of any of the light chain variable domain sequences set forth in FIG. 1B. In particular embodiments, a subject rabbit monoclonal antibody has framework sequences or CDRs that are substantially identical (e.g., at least about 70%, at least about 80%, at least about 90%, at least about 95% or at least about 98% identical) to the framework sequences or CDRs of any of the heavy or light chain sequences shown in FIG. 1A or 1B.

In certain embodiments, rabbit monoclonal antibodies of the invention may contain a heavy or light chain that is encoded by a polynucleotide that hybridizes under high stringency conditions to a rabbit heavy or light chain-encoding nucleic acid. High stringency conditions include incubation at 50° C. or higher in 0.1×SSC (15 mM saline/0.15 mM sodium citrate).

In certain embodiments, rabbit monoclonal antibodies of the invention may contain a heavy or light chain that is encoded by a polynucleotide that is at least 80% identical to (e.g., at least 85%, at least 90%, at least 95%, at least 98%) a rabbit heavy or light chain-encoding nucleic acid. The percentage identity is based on the shorter of the sequences compared. Well known programs such as BLASTN (2.0.8) (Altschul et al. (1997) *Nucl. Acids. Res.* 25:3389-3402) using default parameters and no filter may be employed to make a sequence comparison.

The rabbit monoclonal antibody may be a full-length natural antibody or any chimera thereof, for example. Methods for producing chimeric antibodies are known in the art. See e.g., Morrison et al (Science 1985 229:1202); Oi et al (BioTechniques 1986 4:214); Gillies et al. (J. Immunol. Methods 1989 125:191-202) and U.S. Pat. Nos. 5,807,715, 4,816,567 and 4,816397, which are incorporated herein by reference in their entirety.

The amino acid sequences of the CDRs and framework regions of heavy and light chains of 44 exemplary rabbit monoclonal antibodies that neutralize TNFα activity are set forth in FIGS. 1A and 2A, respectively.

Modified Antibodies

The above-described rabbit monoclonal antibodies may be modified to provide modified antibodies that neutralize TNFα activity. The modified antibodies may be made by substituting, adding, or deleting at least one amino acid of an above-described rabbit monoclonal antibody. In one embodiment, an above-described TNFα-neutralizing antibody is modified to provide a humanized antibody for human therapeutic use, or another type of modified antibody. In general, these modified antibodies have the general characteristics of the above-described rabbit antibodies and contain at least the CDRs of an above-described rabbit antibody, or, in certain embodiments, CDRs that are very similar to the CDRs of an above-described rabbit antibody.

Humanized Antibodies

In one embodiment, therefore, the invention provides humanized versions of the above-described rabbit monoclonal antibodies. In general, humanized antibodies are made by substituting amino acids in the framework regions of a parent non-human antibody to produce a modified antibody that is less immunogenic in a human than the parent non-human antibody. Antibodies can be humanized using a variety of techniques known in the art including, for example, CDR-grafting (EP 239,400; PCT publication WO 91/09967; U.S. Pat. Nos. 5,225,539; 5,530,101; and 5,585,089), veneering or resurfacing (EP 592,106; EP 519,596; Padlan, Molecular Immunology 28(4/5):489-498 (1991); Studnicka et al., Protein Engineering 7(6):805-814 (1994); Roguska. et al., PNAS 91:969-973 (1994)), and chain shuffling (U.S. Pat. No. 5,565,332). In certain embodiments, framework substitutions are identified by modeling of the interactions of the CDR and framework residues to identify framework residues important for antigen binding and sequence comparison to identify unusual framework residues at particular positions (see, e.g., U.S. Pat. No. 5,585,089; Riechmann et al., Nature 332:323 (1988)). Additional methods for humanizing antibodies contemplated for use in the present invention are described in U.S. Pat. Nos. 5,750,078; 5,502,167; 5,705,154; 5,770,403; 5,698,417; 5,693,493; 5,558,864; 4,935,496; and 4,816,567, and PCT publications WO 98/45331 and WO 98/45332. In particular embodiments, a subject rabbit antibody may be humanized according to the methods set forth in published U.S. patent applications 20040086979 and 20050033031. Accordingly, the rabbit antibodies described above may be humanized using methods that are well known in the art.

In one embodiment of particular interest, a subject rabbit monoclonal antibody may be humanized in accordance with the methods set forth in great detail in U.S. patent application Ser. No. 10/984,473, filed on Nov. 8, 2004 and entitled "Methods for antibody engineering", which application is incorporated by reference in its entirety. In general, this humanization method involves identifying a substitutable position of an antibody by comparing sequences of antibodies that bind to the same antigen, and replacing the amino acid at that position with a different amino acid that is present at the same position of a similar human antibody. In these methods, the amino acid sequence of a parental rabbit antibody is compared to (i.e., aligned with) the amino acid sequences of other related rabbit antibodies to identify variation tolerant positions. The amino acid sequence of the variable domain of the parental rabbit antibody is usually compared to a database of human antibody sequences, and a human antibody that has an amino acid sequence that is similar to that of the parental antibody is selected. The amino acid sequences of the parental antibody and the human antibody are compared (e.g., aligned), and amino acids at one or more of the variation tolerant positions of the parental antibody are substituted by correspondingly positioned amino acids in the human antibody.

The above-discussed variation tolerant position substitution methods are readily incorporated into any known humanization method and are also readily employed to produce humanized antibodies containing CDR regions that are altered with respect to the CDR regions of the parent antibody. Accordingly humanized TNFα-neutralizing antibodies containing altered versions of the CDRs of the above-described rabbit monoclonal antibodies are provided.

The humanized TNFα-neutralizing antibodies of the invention therefore may contain the unaltered CDRs of an above-described rabbit TNFα-neutralizing antibody, or, in certain embodiments, altered CDRs of an above-described rabbit TNFα-neutralizing antibody. A humanized antibody containing altered CDRs of an above-described rabbit TNFα-neutralizing antibody generally contains CDRs having 1, up to 2, up to 3, up to 4, up to 5, up to 6, up to 7 and in certain cases up to about 10 amino acid substitutions, as compared to the CDRs of an above-described rabbit TNFα-neutralizing antibody. The particular substitutable positions of a CDR, as well as the donor amino acid that can be substituted into those positions, are readily apparent from U.S. Ser. No. 10/984,473, filed on Nov. 8, 2004, and the sequence alignments shown in FIGS. 1A and 1B.

Substitutable positions of a rabbit TNFα-neutralizing antibody, as well the choice of amino acids that may be substituted into those positions, are revealed by aligning the heavy and light chain amino acid sequences of the rabbit antibodies discussed above, and determining which amino acids occur at which positions of those antibodies. In one exemplary embodiment, the rabbit heavy and light chain amino acid sequences of FIGS. 1A and 1B are aligned (as shown in FIGS. 1A and 1B), and the identity of amino acids at each position of 44 exemplary rabbit TNFα-neutralizing antibodies is determined. As illustrated in FIGS. 2A (illustrating the amino acids present at each position of the heavy chains of 44 exemplary rabbit TNFα-neutralizing antibodies) and 2B (illustrating the amino acids present at each position of the light chains of 44 exemplary rabbit TNFα-neutralizing antibodies), several substitutable positions, as well as the amino acids that can be substituted into those positions, are readily identified. For example, according to this analysis, for heavy chains, Q, E or V may be employed at position 2, S or Q may be employed at position 3, and L or V may be employed at position 4, and so on. In particular embodiments, an amino acid at a substitutable position of a subject rabbit antibody may be substituted by an amino acid at a corresponding position of a similar human antibody to humanize the rabbit antibody. In one embodiment, the amino acid of the human antibody is only substituted into the rabbit antibody if the amino acid is one of the amino acids known to be present at that position in a different rabbit antibody that binds to the same antigen.

In a refinement of this method and as described in greater detail in U.S. Ser. No. 10/984,473, a group of related rabbit antibodies, i.e., antibodies that have a similar sequence and also produced by cells that have a common B cell ancestor, are identified. The antibodies within each group of related antibodies generally share a common ancestor antibody, and have evolved from that ancestor antibody via somatic hypermutation, gene conversion and other cellular mutation-producing mechanisms that occur during affinity maturation and the final stages of B-cell development. The amino acid sequences of the antibodies within a group can be compared to identify substitutable positions. A substitutable position of an individual antibody is identified by virtue of the fact that the identity of the amino acid at that position varies between the individual antibodies of a group of related antibodies. Once identified, the amino acid at the substitutable position of an individual antibody can be substituted for a different amino acid without significantly decreasing the affinity of the antibody. Since antibodies containing amino acid substitutions at these substitutable positions were originally produced and effectively tested by the immune system of the initial immunized animal, substitution at those positions should be well tolerated by the antibody. Substitutable positions in CDRs and framework regions may be identified in these methods.

For example, the 44 exemplary rabbit antibodies discussed above are readily classified by sequence to produce 7 groups of related antibodies, termed herein as Groups A-G. Sequence alignments of the heavy and light chains of the antibodies within each of the seven groups, as well as an indication (*) of which positions of those heavy and light chains are substitutable, are illustrated in FIGS. 3A and 3B, respectively. If such a substitution is desirable, a humanizing amino acid substitution may be made at any one or more (e.g., 1, up to 2, up to 3 or up to 4 or more) of those positions.

As noted above, the subject rabbit antibodies may be modified to provide modified antibodies. In particular embodiments, these methods include making one or more amino acid substitutions (e.g., one, up to two, up to three, up to four or up to five of more, usually up to 10 or more). An amino acid substitution may be at any position, and the amino acid at that position may be substituted by an amino acid of any identity. In certain embodiments, a modified antibody may have the same general characteristics of the above-described rabbit antibodies. In one embodiment, after a substitutable position has been identified using the methods of U.S. Ser. No. 10/984,473, the amino acids at that position may be substituted. In particular embodiments, an amino acid substitution may be a humanizing substitution (i.e., a substitution that make the amino acid sequence more similar to that of a human antibody), a directed substitution (e.g., a substitution that make the amino acid sequence of an antibody more similar to that of a related antibody in the same group), a random substitution (e.g., a substitution with any of the 20 naturally-occurring amino acids) or a conservative substitution (e.g., a substitution with an amino acid having biochemical properties similar to that being substituted).

Exemplary substitutable positions of the representative rabbit antibodies of FIGS. 1A and 1B are listed above. These positions may be substituted without significant loss of antibody activity.

In certain embodiments, modified antibodies of the invention may contain a heavy or light chain that is encoded by a polynucleotide that hybridizes under high stringency conditions to a rabbit heavy or light chain-encoding nucleic acid.

High stringency conditions include incubation at 50° C. or higher in 0.1×SSC (15 mM saline/0.15 mM sodium citrate).

In certain embodiments, modified antibodies of the invention may contain a heavy or light chain that is encoded by a polynucleotide that is at least 80% identical to (e.g., at least 85%, at least 90%, at least 95%, at least 98%) a rabbit heavy or light chain-encoding nucleic acid. The percentage identity is based on the shorter of the sequences compared. Well known programs such as BLASTN (2.0.8) (Altschul et al. (1997) *Nucl. Acids. Res.* 25:3389-3402) using default parameters and no filter may be employed to make a sequence comparison.

Methods of Using Antibodies to Inhibit TNFα Activity

Any of the antibodies described above, including the subject rabbit monoclonal antibodies and humanized versions of the same, may be employed in a method of inhibiting TNFα activity. The antibodies may be employed in a variety of protocols described below.

In one embodiment, a modified antibody may be produced and tested for TNFα-neutralizing activity. In other words, in one embodiment the method includes altering at least 1 amino acid of a subject rabbit monoclonal antibody to produce a modified antibody, and testing the modified antibody for a TNFα neutralizing activity.

The protocols that may be employed in these methods are numerous, and include but are not limited to cell-free assays, e.g., binding assays to a TNFα receptor; cellular assays in which a cellular phenotype is measured, e.g., gene expression or cytotoxicity; and in vivo assays that involve a particular animal (which, in certain embodiments may be an animal model for a TNFα-related condition).

Such assays, including those described above, are well known in the art and are described in a variety of publications, including 20040151722, 20050037008, 20040185047, 20040138427, 20030187231, 20040002589, 20030199679, U.S. Pat. No. 6,090,382 and Balazovich (Blood 1996 88: 690-696).

Methods for Producing Antibodies

In many embodiments, the nucleic acids encoding a subject monoclonal antibody are introduced directly into a host cell, and the cell incubated under conditions sufficient to induce expression of the encoded antibody.

Any cell suitable for expression of expression cassettes may be used as a host cell. For example, yeast, insect, plant, etc., cells. In many embodiments, a mammalian host cell line that does not ordinarily produce antibodies is used, examples of which are as follows: monkey kidney cells (COS cells), monkey kidney CV1 cells transformed by SV40 (COS-7, ATCC CRL 165 1); human embryonic kidney cells (HEK-293, Graham et al. J. Gen Virol. 36:59 (1977)); baby hamster kidney cells (BHK, ATCC CCL 10); chinese hamster ovary-cells (CHO, Urlaub and Chasin, Proc. Natl. Acad. Sci. (USA) 77:4216, (1980); mouse sertoli cells (TM4, Mather, Biol. Reprod. 23:243-251 (1980)); monkey kidney cells (CV1 ATCC CCL 70); african green monkey kidney cells (VERO-76, ATCC CRL-1587); human cervical carcinoma cells (HELA, ATCC CCL 2); canine kidney cells (MDCK, ATCC CCL 34); buffalo rat liver cells (BRL 3A, ATCC CRL 1442); human lung cells (W138, ATCC CCL 75); human liver cells (hep G2, HB 8065); mouse mammary tumor (MMT 060562, ATCC CCL 51); TR1 cells (Mather et al., Annals N.Y. Acad. Sci 383:44-68 (1982)); NIH/3T3 cells (ATCC CRL-1658); and mouse L cells (ATCC CCL-1). Additional cell lines will become apparent to those of ordinary skill in the art. A wide variety of cell lines are available from the American Type Culture Collection, 10801 University Boulevard, Manassas, Va. 20110-2209.

Methods of introducing nucleic acids into cells are well known in the art. Suitable methods include electroporation, particle gun technology, calcium phosphate precipitation, direct microinjection, and the like. The choice of method is generally dependent on the type of cell being transformed and the circumstances under which the transformation is taking place (i.e. in vitro, ex vivo, or in vivo). A general discussion of these methods can be found in Ausubel, et al, Short Protocols in Molecular Biology, 3rd ed., Wiley & Sons, 1995. In some embodiments lipofectamine and calcium mediated gene transfer technologies are used.

After the subject nucleic acids have been introduced into a cell, the cell is typically incubated, normally at 37° C., sometimes under selection, for a period of about 1-24 hours in order to allow for the expression of the antibody. In most embodiment, the antibody is typically secreted into the supernatant of the media in which the cell is growing in.

In mammalian host cells, a number of viral-based expression systems may be utilized to express a subject antibody. In cases where an adenovirus is used as an expression vector, the antibody coding sequence of interest may be ligated to an adenovirus transcription/translation control complex, e.g., the late promoter and tripartite leader sequence. This chimeric gene may then be inserted in the adenovirus genome by in vitro or in vivo recombination. Insertion in a non-essential region of the viral genome (e.g., region E1 or E3) will result in a recombinant virus that is viable and capable of expressing the antibody molecule in infected hosts. (e.g., see Logan & Shenk, Proc. Natl. Acad. Sci. USA 81:355-359 (1984)). The efficiency of expression may be enhanced by the inclusion of appropriate transcription enhancer elements, transcription terminators, etc. (see Bittner et al., Methods in Enzymol. 153:51-544 (1987)).

For long-term, high-yield production of recombinant antibodies, stable expression may be used. For example, cell lines, which stably express the antibody molecule may be engineered. Rather than using expression vectors which contain viral origins of replication, host cells can be transformed with immunoglobulin expression cassettes and a selectable marker. Following the introduction of the foreign DNA, engineered cells may be allowed to grow for 1-2 days in an enriched media, and then are switched to a selective media. The selectable marker in the recombinant plasmid confers resistance to the selection and allows cells to stably integrate the plasmid into a chromosome and grow to form foci which in turn can be cloned and expanded into cell lines. Such engineered cell lines may be particularly useful in screening and evaluation of compounds that interact directly or indirectly with the antibody molecule.

Once an antibody molecule of the invention has been produced, it may be purified by any method known in the art for purification of an immunoglobulin molecule, for example, by chromatography (e.g., ion exchange, affinity, particularly by affinity for the specific antigen after Protein A, and sizing column chromatography), centrifugation, differential solubility, or by any other standard technique for the purification of proteins. In many embodiments, antibodies are secreted from the cell into culture medium and harvested from the culture medium.

Formulations and Administration

The antibodies of the invention may be administered in any manner which is medically acceptable. This may include injections, by parenteral routes such as intravenous, intravascular, intraarterial, subcutaneous, intramuscular, intratumor, intraperitoneal, intraventricular, intraepidural, or others as well as oral, nasal, ophthalmic, rectal, or topical. Sustained release administration is also specifically included in the invention, by such means as depot injections or erodible implants. Localized delivery is particularly contemplated, by such means as delivery via a catheter to one or more arteries, such as the renal artery or a vessel supplying a localized tumor.

The subject antibodies may be an a pharmaceutically acceptable carrier. The term "pharmaceutically acceptable carrier" means one or more organic or inorganic ingredients, natural or synthetic, with which the mutant proto-oncogene or mutant oncoprotein is combined to facilitate its application. A suitable carrier includes sterile saline although other aqueous and non-aqueous isotonic sterile solutions and sterile suspensions known to be pharmaceutically acceptable are known to those of ordinary skill in the art. An "effective amount" refers to that amount which is capable of ameliorating or delaying progression of the diseased, degenerative or damaged condition. An effective amount can be determined on an individual basis and will be based, in part, on consideration of the symptoms to be treated and results sought. An effective amount can be determined by one of ordinary skill in the art employing such factors and using no more than routine experimentation.

In one embodiment a subject antibody is administered to a patient by intravenous, intramuscular or subcutaneous injection. An antibody may be administered within a dose range between about 0.1 mg/kg to about 100 mg/kg; between about 1 mg/kg to 75 mg/kg; or about 10 mg/kg to 50 mg/kg. The antibody may be administered, for example, by bolus injunction or by slow infusion. Slow infusion over a period of 30 minutes to 2 hours may be used.

Utility

The subject antibodies are useful for treating a TNF-α-mediated disorder. In one embodiment, the invention provides a method of treating a subject for a TNFα-related condition. The method generally involves administering a subject antibody a subject having a TNFα-related disorder in an amount effective to treat at least one symptom of the TNFα-related disorder.

The term "TNF-α-mediated disorder" refers to any disorder or disease state in which TNF-α plays a direct role, e.g., by excessive production or release of TNF-α itself or by TNF-α-induced production or release of another agent that produces a pathological effect. As such, the subject methods are useful for treating any fibrotic disorder, including obliterative bronchiolitis, interstitial lung disease, fibrotic lung disease (e.g., idiopathic pulmonary fibrosis (IPF), pulmonary fibrosis of a known etiology, e.g. cystic fibrosis, adult respiratory distress, syndrome (ARDS), tumor stroma in lung disease, systemic sclerosis, Hermansky-Pudlak syndrome (HPS), coal worker's pneumoconiosis (CWP), asbestosis, sarcoidosis, silicosis, black lung disease, chronic pulmonary hypertension, AIDS associated pulmonary hypertension, and the like), human kidney disease (e.g., nephrotic syndrome, Alport's syndrome, HIV-associated nephropathy, polycystic kidney disease, Fabry's disease, diabetic nephropathy, and the like), glomerular nephritis, nephritis associated with systemic lupus erythematosus, fibrotic vascular disease, arterial sclerosis, atherosclerosis, varicose veins, coronary infarcts, cerebral infarcts, musculoskeletal fibrosis, post-surgical adhesions, cutis keloid formation, progressive systemic sclerosis, primary sclerosing cholangitis (PSC), renal fibrosis, scleroderma (local and systemic), diabetic retinopathy, glaucoma, Peyronie's disease, penis fibrosis, arethrostenosis after test using cystoscope, inner accretion after surgery, myelofibrosis, idiopathic retroperitoneal fibrosis, fibrosis incident to microbial infection (e.g. viral, bacterial, fungal, parasitic, etc.), fibrosis incident to inflammatory bowel disease (including stricture formation in Crohn's disease and microscopic colitis), fibrosis induced by chemical or environmental insult (e.g., cancer chemotherapy, pesticides, radiation (e.g. cancer radiotherapy), and the like), peritoneal fibrosis, liver fibrosis, myocardial fibrosis, pulmonary fibrosis, Grave's opthalmopathy, drug induced ergotism, cardiovascular disease, fibrosis incident to benign or malignant cancer (including desmoid tumor), Alzheimer's disease, scarring, scleroderma, glioblastoma in Li-Fraumeni syndrome, sporadic glioblastoma, myeloid leukemia, acute myelogenous leukemia, myelodysplastic syndrome, myeloproliferative syndrome, fibrosis incident to benign or malignant gynecological cancer (e.g., ovarian cancer, Lynch syndrome, and the like), Kaposi's sarcoma, Hansen's disease, inflammatory bowel disease (including stricture formation in Crohn's disease and microscopic colitis), Crohn's disease, ulcerative colitis, multiple sclerosis, Type II diabetes, rheumatoid arthritis, asthma, chronic bronchitis, atopic dermatitis, urticaria, allergic rhinitis, allergic conjunctivitis, chronic obstructive pulmonary disease, graft rejection, graft-versus-host disease, sepsis, and the like.

Some of these disorders are described in greater detail below.

CNS disorders Evidence exists in the literature that TNF-α has effects on cells of the central nervous systems (CNS). Evidence for CNS production of TNF-α, involvement of TNF-α in brain injury, the role of polymorphonuclear leukocytes (PMNs) in brain injury, the role of adhesion molecules in brain injury, and potential TNF-α directed therapeutic strategies for prevention of brain injury have been reviewed in the literature. See, e.g., Babak Arvin et al. (1995) Ann. N.Y. Acad. Sciences 765: 62-71.

The prevention of brain edema by anti-TNF-α antibodies in experimental meningitis provides firm evidence for the involvement of TNF-α in the breakdown of the Blood Brain Barrier. TNF-α can also trigger the infiltration of neutrophils into the tissue with consequent induction of secondary mediators in local areas. See, e.g., "Cytokines and CNS," Edit: R. M. Ransohoff and E. N. Beneviste, CRC Press, Page 193, 1996).

Closed head injury (CHI) in rats triggers the production of TNF-α in the contused brain hemisphere, and it was shown that a decrease in TNF-α levels or inhibition of its activity is accompanied by significantly reduced brain damage. Shohami et al. (1996) J. Cerebral Blood Flow Metab., 16:378-384.

Multiple Sclerosis Multiple sclerosis (MS) plaques within the CNS are infiltrated by peripheral blood mononuclear cells. In patients, TNF-α, but not lymphotoxin, is overproduced by peripheral blood mononuclear cells during MS relapse. Glabinski et al. (1995) Neurol Scand. 91:276-279. TNF-α has an ability to cause cell death of oligodendrocytes in vitro. Robbins et al. (1987) J. Immunol., 139:2593. This aspect of TNF-α activity may contribute directly to myelin damage and/or the demyelination process observed in diseases such as multiple sclerosis (MS). TNF-α has been shown to play a central role in the demyelination of the CNS in MS. Serum levels of TNF-α are elevated in patients with active MS, and TNF-α producing macrophages, microglia and astrocytes are present at active lesion sites. In in vitro experiments, TNF-α directly mediates oligodendrocyte damage and suppresses myelin formation, and it stimulates astrocytes, which are then responsible for the CNS scarring plaques in MS (Owens and Sriram, Neurological Clinics, 13:51, 1995).

Serum levels of TNFα are elevated in patients with active MS (M. Chofflon et al., Eur. Cytokine Net., 3:523, 1991; Sharief, M. K. and Hentgen, N. E. Jour. Med., 325:467, 1991). TNF-α producing macrophages/microglia and astrocytes are present at active lesion sites (K. Selmaj al., Jour. Clin. Invest., 87:949, 1991). In in vitro experiments, TNF-α directly mediates oligodendrocyte damage and suppresses myelin formation (K. Selmaj et al., J. Immunol., 147:1522, 1990); T. Tsumamoto et al., Acta Neurol. Scand., 91:71, 1995), and it stimulates astrocytes, which are responsible for the scarring plaques (K. Selmaj et al., J. Immunol., 144:129, 1990).

An increase in TNF-α expression preceding MS exacerbation attacks has been shown. ("Cytokines and the CNS," Edit: R. M. Ransohoff and E. N. Beneviste, CRC Press, 1996, p. 232). In vivo studies of murine, rat and human demyelinating diseases indicate that TNF-α participates in the inflammatory reactions that take place within the CNS. TNF-α positive astrocytes and macrophages have been identified in the brains of MS patients, particularly in the plaque region (F. M. Hofman et al., J. Exp. Med., 170:607, 1991, and Selmaj et al., J. Clin. Invest., 87:949, 1991) have determined that both TNF-α and TNF-β are present in MS plaque regions, and that TNF-α is localized within astroyctes, whereas TNF-α is associated with microglia and T-cells. Increased serum and cerebrospinal fluid levels of TNF-α have been documented in patients with MS (Sharief, M. K., M. Phil, and R. Hentges, N. Engl. J. Med., 325:467, 1991), and a strong correlation exists between cerebrospinal fluid levels of TNF-α, disruption of the blood brain barrier, and high levels of circulating ICAM-1 in patients with active MS.

Alzheimer's Disease Alzheimer's disease (AD), the most common dementing disorder of late life, is a major cause of disability and death in the elderly. The disease is manifested by the appearance of abnormalities in the brain, particularly involving the hippocampus, amygdala, thalamus and neocortex. Lesions in these regions are associated with dysfunction/death of neurons and deafferentation of targets. The principal pathological hallmarks of AD are deposits of the amyloid-β protein (Aβ) in extracellular parenchyma and cerebral vessels, and neurofibrillary tangles.

TNF-α has been generally elevated in the serum of AD patients based upon both antibody assays and bioassays. In one study almost half of the AD cases had elevated TNF-α, but none of the controls had a similar elevation. The blood-brain barrier does not normally permit passage of cytokines. However, there is evidence to suggest that the blood-brain barrier may not be intact in AD.

Respiratory disorders TNF-α has been shown to play a role in pulmonary fibrosis induced by bleomycin and silica (Piguet et al., Jour. Exper. Med., 170:655-663, 1989, and Nature, 344:245-247, 1990; Everson and Chandler, Amer. Jour. Path., 140:503-512, 1992; Phan and Kunkel, Exp. Lung Res. 18:29-43, 1992; also, Warren et al., Jour. Clin. Invest., 84:1873-1882, 1989; Denis et al., Amer. Jour. Cell Mol. Biol., 5:477-483, 1991). TNF-α has been reported to orchestrate its proinflammatory effects by regulating the compartmentalized release of secondary messenger cytokines. Investigations have shown that nude mice exposed to chronic in vivo TNF-α develop pulmonary inflammation and fibrosis (ARRD 145:A307, 1992).

Asthma It has been reported that levels of TNF-α are increased in bronchoalveolar lavage (BAL) fluid from patients with allergic asthma. Cirelli, et al. (1995) Amer. Jour. Resp. Critical Care Med., 151:345A; Redington et al., (1995) Amer. Jour. Respir. Crit. Care Med., 151: 702A. These findings indicate an increased tissue level of TNF-α in asthma and that this may contribute to the pathophysiology of the condition.

Chronic Obstructive Pulmonary Disease (COPD) Another disease state in which TNF-α plays a role in the pathophysiology is chronic obstructive pulmonary disease. In silicosis, a disease of progressive respiratory failure caused by a fibrotic reaction, antibody to TNF-α completely blocked the silica-induced lung fibrosis in mice (Piguet et al., Nature, 344:245-247, 1990). High levels of TNF-production (in the serum and in isolated macrophages) have been demonstrated in animal models of silica and asbestos induced fibrosis (Bissonnette et al., Inflammation, 13:329-339, 1989).

Adult Respiratory Distress Syndrome (ARDS) Excessive TNF-alpha. concentrations in excess of 12,000 pg/ml have been detected in pulmonary aspirates from ARDS patients (Millar et al., Lancet, 2(8665):712-714, 1989). Systemic infusion of recombinant TNF-α was shown to result in changes typically seen in ARDS (Ferrai-Baliviera et al., Arch. Surg., 124:1400-1405, 1989).

Lung Sarcoidosis Alveolar macrophages from pulmonary sarcoidosis patients have been found to spontaneously release massive quantities of TNF-α as compared with macrophages from normal donors (Baughman et al., Jour. Lab. Clin. Med., 115:36-42, 1990). TNF-α also implicated in other acute disease states such as the pathophysiologic responses which follows subsequent reperfusion. It is involved in reperfusion injury, and is a major cause of tissue damage after loss of blood flow. (Vedder et al., Proc. Nat. Acad. Sci., 87:2643-2646, 1990).

Sepsis Overproduction of TNF-α has been implicated in the pathogenesis of endotoxin induced septic shock, (see Carswell et al., Proc. Nat. Acad. Sci., 2:3666-3670, 1975). Endotoxin is the lipopolysaccharide component of the cell wall of gram-negative bacteria, and is a macrophage activator which induces the synthesis and enhanced secretion of TNF-α and other biologically active cytokine molecules. TNF-α is recognized as a central mediator of sepsis, septic shock and multiple organ failure. These host reactions are associated with increased blood levels of TNF-α, due to increased TNF-α production. (F. Stuber et al., Jour. Inflam., 46:42-50, 1996).

Liver disorders Because of its central role in metabolism and host defense mechanisms, the liver is thought to be major organ responsible for initiation of the multiple organ failure during sepsis. The depression in hepatocellular function in early, hyperdynamic stages of sepsis does not appear to be due to any reduction in hepatic perfusion, but is associated with elevated levels of circulating cytokines such as TNF-α. Furthermore, administration of recombinant TNF-α at doses that do not reduce cardiac output or hepatic perfusion, produces hepatocellular dysfunction. (P. Wang et al., Amer. Jour. Physiol., 270:5, 1996).

The role of TNF-α in induction of hepatic apoptosis under transcriptional arrest, activation of the 55 kDa receptor in the induction of hepatic apoptosis, the glycosylation step in TNF-induced hepatic apoptosis, hepatic injury induction by T cell-initiated cytokine release, and Ta cell-dependent TNF-mediated liver injury without transcriptional arrest has been reported. (A. Wendel et al., Cell. Biol. Mol. Basis Liver Transp., Int., Ringberg Conf. Hepatic Transp., 2nd, 1995, Pages 105-111.).

Diabetes TNF-α plays a central role in the state of insulin resistance associated with obesity. It has been previously shown that one important mechanism by which TNF-α interferes with insulin signaling is through serine phosphorylation of insulin receptor substrate-1 (IRS-1), which can function as an inhibitor of the tyrosine kinase activity of the insulin receptor (IR). The data strongly suggest that TNF-α inhibits signaling via a stimulation of p55 TNFR, and sphingomyelinase activity, which results in the production of an inhibitory form of IRS-1 (Peraldi et al., J. Biol. Chem. 271:13018-13022, 1996).

Crohn's disease TNF-α levels are elevated in Crohn's disease. In one study, TNF-α concentrations were measured in stool samples from normal children, infants with diarrhea, and children with inflammatory bowel disease in active and inactive phases. Compared with diarrhea controls, stool TNF-α concentrations were significantly increased in children with active Crohn's disease. In patients with inactive Crohn's disease, either as a result of surgery, or treatment with steroids, the concentration of stool TNF-α fell to the level of the controls (C. P. Braegger et al., Lancet, 339:89-91, 1992).

Pre-Eclampsia Pre-eclampsia is an endothelial disorder, and TNF-α has fundamental effects on endothelial cells by several means, including alteration of the balance between oxidant and anti-oxidant, changing the pattern of prostaglandin production, and affecting the expression of several cell surface components. In patients, results show that TNF-α mRNA expression is significantly elevated in preeclamptic patients compared to the control groups. These observations are consistent with a major role for TNF-α in the development of eclampsia (G. Chen et al., Clin. Exp. Immunol. 104:154-159, 1996).

Dermal Burns The protein catabolic rate and TNF-α content of the soleus muscle of the scalded region and remote region were dynamically determined in the first week after the rats were inflicted with 37% TBSA full thickness scalding. The TNF-α content of skeletal muscles was far greater in the scalded region than in the remote region. TNF-.alpha. increase was also significantly correlated to the protein catabolic rate of the skeletal muscles (Li et al., Jour. Med. Coll., PLA 10:262-267, 1995; C.A. 125:938, 1245:8156a, 1996).

Bone Resorption TNF-α is increased in bone resorption diseases, including arthritis, wherein it has been determined that when activated, leukocytes will produce a bone reabsorbing activity. Data indicate that TNF-α enhances this activity (Bertolini et al., Nature, 319:516-518, 1986, and Johnson et al., Endocrinology, 124:1424-1427, 1989). TNF-α stimulates bone resorption and inhibits bone formation in vitro and in vivo through stimulation of osteoclast formation and activation combined with inhibition of osteoblast function. TNF-α may be involved in many bone resorption diseases, including arthritis.

Rheumatoid Arthritis Analysis of cytokine mRNA and protein in human rheumatoid arthritis tissue revealed that many proinflammatory cytokines such as TNF-α are abundant in all patients regardless of therapy. In rheumatoid joint cell cultures that spontaneously produce IL1, TNF-α was the major dominant regulator of IL1. Subsequently, other proinflammatory cytokines were also inhibited if TNF-α was neutralized, leading to the concept that the proinflammatory cytokines were linked in a network with TNF-α at its apex. This led to the concept that TNF-α was of major importance in rheumatoid arthritis. This has been successfully tested in animal models of collagen-induced arthritis, and these studies have provided the rationale for clinical trials of anti-TNF-α therapy in patients with long-standing rheumatoid arthritis. Several clinical trials using a chimeric anti-TNF-α antibody have shown marked clinical benefit, verifying the concept that TNF-α is of major importance in rheumatoid arthritis. Re-treatment clinical studies have also shown benefit in repeated relapses, indicating that the disease remains TNF-α dependent (M. Feldmann, Annual Rev. Immunol., 14:397-440, 1996.).

Vascular disorders TNF-α alters the properties of endothelial cells and has various pro-coagulant activities, such as production of an increase in tissue factor procoagulant activity and suppression of the anticoagulant protein C pathway as well as down-regulating the expression of thrombomodulin (Sherry et al., Jour. Cell. Biol., 107:1269-1277, 1988). TNF-α has activities which, together with its early production (during the initial stages of a trauma or injury event), make it a mediator of response to tissue injury in several important disorders including, but not limited to myocardial infarction, stroke and circulatory shock. Of specific importance may be TNF-α induced expression of adhesion molecules, such as intercellular adhesion molecule (ICAM) or endothelial leukocyte adhesion molecule on endothelial cells (Munro et al., Am. Jour. Path., 135:121-132, 1989).

Cardiac disorders Evidence indicates that the current top suspects in heart failure are noradrenaline, angiotensin, vasopressin, endothelin, and tumor-necrosis factor (TNF-.alpha.), (N.E. J. Med., 323:236-241, 1990). It has been reported that concentrations of TNF-α, which cause cachexia in chronic inflammatory disorders, infections, cancer and other diseases, are elevated in patients with severe heart failure, especially those with the more severe manifestations of the disease, such as cardiac cachexia.

Graft vs. host disease In graft versus host reactions, increased serum TNF-α levels have been associated with major complications following acute allogenic bone marrow transplants (Holler et al., Blood, 75:1011-1016, 1990).

An subject antibody modulates, i.e., reduces or increases a symptom of the animal model disease or condition by at least about 10%, at least about 20%, at least about 25%, at least about 30%, at least about 35%, at least about 40%, at least about 45%, at least about 50%, at least about 55%, at least about 60%, at least about 65%, at least about 70%, at least about 80%, at least about 90%, or more, when compared to a control in the absence of the antibody. In general, a subject antibody will cause a subject animal to be more similar to an equivalent animal that is not suffering from the disease or condition. Monoclonal antibodies that have therapeutic value that have been identified using the methods and compositions of the invention are termed "therapeutic" antibodies.

Kits

Also provided by the subject invention are kits for practicing the subject methods, as described above. The subject kits at least include one or more of: a subject antibody, a nucleic acid encoding the same, or a cell containing the same. The subject antibody may be humanized. Other optional components of the kit include: buffers, etc., for administering the antibody or for performing a TNFα activity assay. The nucleic acids of the kit may also have restrictions sites, multiple cloning sites, primer sites, etc to facilitate their ligation to non-rabbit antibody nucleic acids. The various components of the kit may be present in separate containers or certain compatible components may be precombined into a single container, as desired.

In addition to above-mentioned components, the subject kits typically further include instructions for using the components of the kit to practice the subject methods. The instructions for practicing the subject methods are generally recorded on a suitable recording medium. For example, the instructions may be printed on a substrate, such as paper or plastic, etc. As such, the instructions may be present in the kits as a package insert, in the labeling of the container of the kit or components thereof (i.e., associated with the packaging or subpackaging) etc. In other embodiments, the instructions are present as an electronic storage data file present on a suitable computer readable storage medium, e.g. CD-ROM, diskette, etc. In yet other embodiments, the actual instructions are not present in the kit, but means for obtaining the instructions from a remote source, e.g. via the internet, are provided. An example of this embodiment is a kit that includes a web address where the instructions can be viewed and/or from which the instructions can be downloaded. As with the instructions, this means for obtaining the instructions is recorded on a suitable substrate.

Also provided by the subject invention is are kits including at least a computer readable medium including programming as discussed above and instructions. The instructions may include installation or setup directions. The instructions may include directions for use of the invention with options or combinations of options as described above. In certain embodiments, the instructions include both types of information.

Providing the software and instructions as a kit may serve a number of purposes. The combination may be packaged and purchased as a means for producing rabbit antibodies that are less immunogenic in a non-rabbit host than a parent antibody, or nucleotide sequences them.

The instructions are generally recorded on a suitable recording medium. For example, the instructions may be printed on a substrate, such as paper or plastic, etc. As such, the instructions may be present in the kits as a package insert, in the labeling of the container of the kit or components thereof (i.e., associated with the packaging or subpackaging), etc. In other embodiments, the instructions are present as an electronic storage data file present on a suitable computer readable storage medium, e.g., CD-ROM, diskette, etc, including the same medium on which the program is presented.

It is evident from the above discussion that the subject invention provides important new TNFα-neutralizing antibodies. Accordingly, the present invention represents a significant contribution to the art.

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto.

That which is claimed is:

1. A method of reducing binding of TNF-α to a TNF-α receptor, comprising:
   contacting TNF-α in the presence of a TNF-α receptor with a monoclonal antibody comprising:
   a) a variable domain comprising:
      i. a heavy chain comprising a CDR1 region identical to amino acid residues 30-34 of SEQ ID NO: 31, a CDR2 region identical to amino acid residues 49-64 of SEQ ID NO: 31 and a CDR3 region identical to amino acid residues 97-109 of SEQ ID NO: 31; and
      ii. a light chain comprising a CDR1 region identical to amino acid residues 23-33 of SEQ ID NO: 75, a CDR2 region identical to amino acid residues 49-55 of SEQ ID NO: 75 and a CDR3 region identical to amino acid residues 88-99 of SEQ ID NO: 75; or
   b) a variant of said variable domain of part a) that is otherwise identical to said variable domain of part a) except for up to 10 amino acid substitutions in said CDR regions,
   thereby reducing binding of TNF-α to said TNF-α receptor.

2. The method of claim 1, wherein said monoclonal antibody comprises a variable domain comprising:
   a heavy chain comprising: a CDR1 region identical to amino acid residues 30-34 of SEQ ID NO: 31, a CDR2 region identical to amino acid residues 49-64 of SEQ ID NO: 31 and a CDR3 region identical to amino acid residues 97-109 of SEQ ID NO: 31; and
   a light chain comprising: a CDR1 region identical to amino acid residues 23-33 of SEQ ID NO: 75, a CDR2 region identical to amino acid residues 49-55 of SEQ ID NO: 75 and a CDR3 region identical to amino acid residues 88-99 of SEQ ID NO: 75.

3. The method of claim 1, wherein said monoclonal antibody comprises:
   a variant of said variable domain of part a) that is otherwise identical to said variable domain of part a) except for 1 to 4 amino acid substitutions in said CDR regions.

4. The method of claim 1, wherein the amino acid sequences of the framework regions of the heavy chain and the light chain of said monoclonal antibody are different from the framework regions of SEQ ID NO: 31 and SEQ ID NO: 75, respectively.

5. The method of claim 4, wherein the amino acid sequences of the framework regions of the heavy chain and the light chain of said monoclonal antibody are different from the framework regions of SEQ ID NO: 31 and SEQ ID NO: 75, respectively, due to humanization of said monoclonal antibody.

6. The method of claim 1, wherein said monoclonal antibody is a single chain antibody.

7. The method of claim 1, wherein said monoclonal antibody comprises a human constant domain.

8. The method of claim 1, wherein said TNF-α receptor is present on a cell that is cultured in vitro.

9. The method of claim 1, wherein said contacting is by combining said monoclonal antibody with an isolated TNF-α receptor.

10. The method of claim 1, wherein said TNF-α receptor is present on a cell that is present in vivo.

11. The method of claim 10, wherein said contacting is done by administering said monoclonal antibody to a mammalian subject.

12. The method of claim 11, wherein said monoclonal antibody is administered to said mammalian subject in a pharmaceutically-acceptable carrier.

13. The method of claim 11, wherein said monoclonal antibody inhibits an activity of TNF-α in said mammalian subject.

14. The method of claim 11, wherein said mammalian subject has a TNF-α-related condition.

* * * * *

SEQUENCE LISTING

```
<160> NUMBER OF SEQ ID NOS: 88

<210> SEQ ID NO 1
<211> LENGTH: 113
<212> TYPE: PRT
<213> ORGANISM: rabbit

<400> SEQUENCE: 1

Gln Ser Val Glu Glu Ser Gly Gly Arg Leu Val Thr Pro Gly Thr Pro
1               5                   10                  15

Leu Thr Leu Ile Cys Thr Val Ser Gly Ile Asp Leu Ser Ser Asn Ser
            20                  25                  30

Met Gly Trp Phe Arg Gln Ala Pro Gly Lys Gly Leu Glu Trp Ile Gly
        35                  40                  45

Leu Ile Ser Ser Ser Gly Ser Ile Asn Tyr Ala Ser Trp Ala Lys Gly
    50                  55                  60

Arg Phe Thr Ile Ser Lys Thr Ser Ser Thr Thr Val Asp Leu Lys Met
65                  70                  75                  80

Thr Ser Leu Thr Thr Glu Asp Thr Ala Ala Tyr Phe Cys Ala Arg Gly
                85                  90                  95

Trp Tyr Glu Phe Asn Val Trp Gly Pro Gly Thr Leu Val Thr Val Ser
            100                 105                 110

Ser

<210> SEQ ID NO 2
<211> LENGTH: 116
<212> TYPE: PRT
<213> ORGANISM: rabbit

<400> SEQUENCE: 2

Gln Ser Leu Glu Glu Ser Gly Gly Gly Leu Val Lys Pro Glu Gly Ser
1               5                   10                  15

Leu Thr Leu Thr Cys Thr Ala Ser Gly Phe Ser Phe Ser Ser Ser Tyr
            20                  25                  30

Tyr Met Cys Trp Val Arg Gln Ala Pro Gly Lys Gly Leu Glu Leu Ile
```

```
                     35                  40                  45
Gly Cys Ile Ser Ser Ser Asp Gly Arg Thr Trp Ser Thr Thr Trp Ala
    50                  55                  60

Arg Gly Arg Phe Thr Ile Ser Lys Thr Ser Thr Val Asp Leu Lys
65                  70                  75                  80

Val Thr Ser Leu Thr Ala Ala Asp Thr Ala Thr Tyr Phe Cys Ala Arg
                    85                  90                  95

Tyr Ile Asp Ile Ser His Ser Asn Leu Trp Gly Pro Gly Thr Leu Val
                100                 105                 110

Thr Val Ser Ser
        115

<210> SEQ ID NO 3
<211> LENGTH: 116
<212> TYPE: PRT
<213> ORGANISM: rabbit

<400> SEQUENCE: 3

Gln Ser Val Lys Glu Ser Glu Gly Gly Leu Phe Lys Pro Asp Glu Thr
1               5                   10                  15

Leu Thr Leu Thr Cys Thr Val Ser Glu Ile Asp Leu Ser Gly Asn Gln
                20                  25                  30

Ile Ser Trp Val Arg Gln Ala Pro Gly Lys Gly Leu Glu Trp Ile Gly
            35                  40                  45

Phe Ile Asp Val Tyr Asn His Ala Tyr Tyr Ala Ser Trp Ala Arg Ser
    50                  55                  60

Arg Ser Thr Ile Thr Arg Asn Thr Asn Leu Asn Thr Val Thr Leu Lys
65                  70                  75                  80

Met Thr Ser Leu Ser Ala Ala Asp Thr Ala Thr Tyr Phe Cys Ala Arg
                85                  90                  95

Asp Gly Gly Ser Ala Gly Phe Asn Ile Trp Gly Pro Gly Thr Leu Val
                100                 105                 110

Thr Val Ser Ser
        115

<210> SEQ ID NO 4
<211> LENGTH: 116
<212> TYPE: PRT
<213> ORGANISM: rabbit

<400> SEQUENCE: 4

Gln Ser Val Lys Glu Ser Glu Gly Gly Leu Phe Lys Pro Ala Glu Thr
1               5                   10                  15

Leu Ala Leu Thr Cys Thr Val Ser Gly Ile Asp Leu Ser Arg Asn Ser
                20                  25                  30

Ile Ser Trp Val Arg Gln Ala Pro Gly Lys Glu Leu Glu Trp Ile Gly
            35                  40                  45

Phe Ile Asp Leu Tyr Gly Ser Ala Tyr Tyr Ala Thr Trp Ala Lys Gly
    50                  55                  60

Arg Ser Thr Ile Thr Arg Asn Thr Asn Leu Asn Thr Val Thr Leu Gln
65                  70                  75                  80

Met Thr Ser Leu Thr Ala Ala Asp Thr Ala Thr Tyr Phe Cys Ala Thr
                85                  90                  95

Asp Gly Gly Ser Ser Gly Phe Asn Ile Trp Gly Pro Gly Thr Leu Val
                100                 105                 110

Thr Val Ser Ser
        115
```

<210> SEQ ID NO 5
<211> LENGTH: 117
<212> TYPE: PRT
<213> ORGANISM: rabbit

<400> SEQUENCE: 5

Gln Ser Val Lys Glu Ser Glu Gly Gly Leu Phe Lys Pro Thr Asp Thr
1               5                   10                  15

Leu Thr Leu Thr Cys Thr Val Ser Gly Phe Ser Leu Ile Ile Asp Gly
            20                  25                  30

Val Ser Trp Val Arg Gln Ala Pro Gly Lys Gly Leu Glu Trp Ile Gly
        35                  40                  45

Ser Ile Gly Asn Ser Gly Arg Ser Tyr Tyr Met Thr Trp Ala Lys Ser
    50                  55                  60

Arg Ala Thr Ile Thr Arg Asn Thr Asn Leu Asn Thr Val Thr Leu Arg
65                  70                  75                  80

Met Thr Ser Leu Thr Ala Ala Asp Thr Ala Thr Tyr Phe Cys Ala Arg
                85                  90                  95

Trp Ala Ile Ser Asp Asp Ala Phe Asn Ile Trp Gly Pro Gly Thr Leu
            100                 105                 110

Val Thr Val Ser Ser
        115

<210> SEQ ID NO 6
<211> LENGTH: 115
<212> TYPE: PRT
<213> ORGANISM: rabbit

<400> SEQUENCE: 6

Gln Ser Leu Glu Glu Ser Gly Gly Gly Leu Val Lys Pro Gly Gly Thr
1               5                   10                  15

Leu Thr Leu Thr Cys Thr Val Ser Gly Ile Asp Leu Ser Asn Asp Ala
            20                  25                  30

Ile Ser Trp Val Arg Gln Ala Pro Gly Lys Gly Leu Glu Tyr Ile Ser
        35                  40                  45

Tyr Ile Ser Asp Tyr Gly Val Arg Tyr Tyr Ala Ser Trp Val Lys Gly
    50                  55                  60

Arg Phe Thr Ile Ser Lys Thr Ser Thr Thr Val Asp Leu Lys Met Thr
65                  70                  75                  80

Ser Leu Thr Thr Glu Asp Thr Ala Thr Tyr Phe Cys Ala Arg Gly Ala
                85                  90                  95

Pro Gly Ala Gly Asp Asn Asp Ile Trp Gly Arg Gly Thr Leu Val Thr
            100                 105                 110

Val Ser Ser
    115

<210> SEQ ID NO 7
<211> LENGTH: 115
<212> TYPE: PRT
<213> ORGANISM: rabbit

<400> SEQUENCE: 7

Gln Ser Leu Glu Glu Ser Gly Gly Gly Leu Val Lys Pro Gly Gly Thr
1               5                   10                  15

Leu Thr Leu Thr Cys Thr Val Ser Gly Ile Asp Leu Ser Asn Asp Ala
            20                  25                  30

Ile Ser Trp Val Arg Gln Ala Pro Gly Lys Gly Leu Glu Tyr Ile Ala

-continued

```
                35                  40                  45
Tyr Ile Ser Asp Tyr Ala Val Lys Tyr Ala Ser Trp Ala Lys Gly
         50                  55                  60

Arg Phe Thr Ile Ser Lys Thr Ser Thr Thr Val Asp Leu Lys Ile Thr
 65                  70                  75                  80

Ser Leu Thr Thr Glu Asp Thr Ala Thr Tyr Phe Cys Ala Arg Gly Ala
                 85                  90                  95

Pro Gly Ala Gly Asp Asn Asp Ile Trp Gly Arg Gly Thr Leu Val Thr
            100                 105                 110

Val Ser Ser
        115

<210> SEQ ID NO 8
<211> LENGTH: 115
<212> TYPE: PRT
<213> ORGANISM: rabbit

<400> SEQUENCE: 8

Gln Ser Leu Glu Glu Ser Gly Gly Gly Leu Val Thr Pro Gly Gly Thr
  1               5                  10                  15

Leu Thr Leu Thr Cys Thr Val Ser Gly Ile Asp Leu Arg Asn Asp Ala
                 20                  25                  30

Ile Ser Trp Val Arg Gln Ala Pro Gly Lys Gly Leu Glu Tyr Ile Ser
             35                  40                  45

Tyr Ile Ser Asp Trp Gly Ile Lys Tyr Ala Ser Trp Val Lys Gly
         50                  55                  60

Arg Phe Thr Ile Ser Lys Thr Ser Thr Thr Val Asp Leu Lys Ile Thr
 65                  70                  75                  80

Ser Leu Thr Thr Ile Glu Asp Thr Ala Thr Tyr Phe Cys Ala Arg Gly Ala
                 85                  90                  95

Pro Gly Ala Gly Asp Asn Gly Ile Trp Gly Arg Gly Thr Leu Val Thr
            100                 105                 110

Val Ser Ser
        115

<210> SEQ ID NO 9
<211> LENGTH: 115
<212> TYPE: PRT
<213> ORGANISM: rabbit

<400> SEQUENCE: 9

Gln Ser Leu Glu Glu Ser Gly Gly Gly Leu Val Lys Pro Gly Gly Thr
  1               5                  10                  15

Leu Thr Leu Thr Cys Thr Val Ser Gly Ile Asp Leu Ser Asn Asp Ala
                 20                  25                  30

Ile Ser Trp Val Arg Gln Ala Pro Gly Lys Gly Leu Glu Tyr Ile Ala
             35                  40                  45

Tyr Ile Ser Asp Trp Ser Ile Arg Tyr Tyr Ala Asn Trp Ala Gln Gly
         50                  55                  60

Arg Phe Thr Ile Ser Lys Thr Ser Thr Thr Val Asp Leu Lys Ile Thr
 65                  70                  75                  80

Ser Leu Thr Thr Glu Asp Thr Ala Thr Tyr Phe Cys Ala Arg Gly Ala
                 85                  90                  95

Pro Gly Ala Gly Asp Asn Gly Ile Trp Gly Arg Gly Thr Leu Val Thr
            100                 105                 110

Val Ser Ser
        115
```

<210> SEQ ID NO 10
<211> LENGTH: 115
<212> TYPE: PRT
<213> ORGANISM: rabbit

<400> SEQUENCE: 10

Gln Ser Leu Glu Glu Ser Gly Gly Leu Val Lys Pro Gly Gly Thr
1               5                   10                  15

Leu Thr Leu Thr Cys Thr Val Ser Gly Ile Asp Leu Ser Asn Asp Ala
                20                  25                  30

Ile Ser Trp Val Arg Gln Ala Pro Gly Lys Gly Leu Glu Tyr Ile Ala
            35                  40                  45

Tyr Ile Ser Asp Tyr Gly Val Arg Tyr Ala Ser Trp Ala Lys Gly
50                  55                  60

Arg Phe Thr Ile Ser Lys Thr Ser Thr Met Val Asp Leu Lys Ile Thr
65                  70                  75                  80

Ser Leu Thr Thr Glu Asp Thr Ala Thr Tyr Phe Cys Ala Arg Gly Ala
                85                  90                  95

Pro Gly Ala Gly Asp Asn Gly Ile Trp Gly Arg Gly Thr Leu Val Thr
            100                 105                 110

Val Ser Ser
        115

<210> SEQ ID NO 11
<211> LENGTH: 115
<212> TYPE: PRT
<213> ORGANISM: rabbit

<400> SEQUENCE: 11

Gln Glu Gln Leu Lys Glu Ser Gly Gly Gly Leu Val Thr Pro Gly Gly
1               5                   10                  15

Thr Leu Thr Leu Thr Cys Thr Ala Ser Gly Phe Thr Ile Ser Ser Tyr
                20                  25                  30

Val Met Thr Trp Val Arg Gln Ala Pro Gly Lys Gly Leu Glu Gly Ile
            35                  40                  45

Gly Tyr Ile Lys Ser Gly Asn Ile Trp Tyr Ala Ser Trp Ala Lys Gly
50                  55                  60

Arg Phe Thr Ile Ser Arg Thr Ser Thr Thr Val Asp Leu Lys Ile Ile
65                  70                  75                  80

Ser Pro Thr Ile Glu Asp Thr Ala Thr Tyr Phe Cys Ala Arg Gly Gly
                85                  90                  95

Val Tyr Asn Ile Gly Leu Asn Ile Trp Gly Pro Gly Thr Leu Val Thr
            100                 105                 110

Val Ser Ser
        115

<210> SEQ ID NO 12
<211> LENGTH: 114
<212> TYPE: PRT
<213> ORGANISM: rabbit

<400> SEQUENCE: 12

Gln Ser Val Glu Glu Ser Gly Gly Arg Leu Val Thr Pro Gly Gly Ser
1               5                   10                  15

Leu Thr Leu Thr Cys Thr Val Ser Gly Phe Ser Leu Ser Ser Phe Val
                20                  25                  30

Met Ser Trp Val Arg Gln Ala Pro Gly Lys Gly Leu Glu Ala Ile Gly

```
                    35                  40                  45
Tyr Ile Lys Ser Gly Asn Ile Trp Tyr Ala Asn Trp Ala Lys Gly Arg
         50                  55                  60

Phe Thr Ile Ser Arg Thr Ser Thr Val Asp Leu Lys Met Thr Ser
65                   70                  75                  80

Leu Thr Thr Glu Asp Thr Ala Thr Tyr Phe Cys Ala Arg Gly Gly Leu
                 85                  90                  95

Tyr Asn Ser Gly Leu Asn Ile Trp Gly Pro Gly Thr Leu Val Thr Val
             100                 105                 110

Ser Ser

<210> SEQ ID NO 13
<211> LENGTH: 114
<212> TYPE: PRT
<213> ORGANISM: rabbit

<400> SEQUENCE: 13

Gln Ser Val Glu Glu Ser Gly Gly Arg Leu Val Thr Pro Gly Gly Ser
 1               5                  10                  15

Leu Thr Leu Thr Cys Thr Val Ser Gly Phe Ser Leu Ser Ser Phe Val
             20                  25                  30

Met Ser Trp Val Arg Gln Ala Pro Gly Lys Gly Leu Glu Ala Ile Gly
         35                  40                  45

Tyr Ile Lys Ser Gly Asn Ile Trp Tyr Ala Ser Trp Ala Lys Gly Arg
     50                  55                  60

Phe Thr Ile Ser Arg Thr Ser Thr Val Asp Leu Lys Met Thr Ser
65                   70                  75                  80

Leu Thr Thr Glu Asp Thr Ala Thr Tyr Phe Cys Ala Arg Gly Gly Val
                 85                  90                  95

Tyr Asn Ser Gly Leu Asn Ile Trp Gly Pro Gly Thr Leu Val Thr Val
             100                 105                 110

Ser Ser

<210> SEQ ID NO 14
<211> LENGTH: 119
<212> TYPE: PRT
<213> ORGANISM: rabbit

<400> SEQUENCE: 14

Gln Ser Leu Glu Glu Ser Gly Gly Asp Leu Val Lys Pro Gly Ala Ser
 1               5                  10                  15

Leu Thr Leu Ala Cys Thr Ala Ser Gly Phe Thr Ile Ser Arg Ser Tyr
             20                  25                  30

Trp Ile Cys Trp Val Arg Arg Ala Pro Gly Lys Gly Leu Glu Trp Ile
         35                  40                  45

Ala Cys Ile Tyr Gly Asp Asn Asp Ile Thr Pro Leu Tyr Ala Asn Trp
     50                  55                  60

Ala Lys Gly Arg Phe Pro Val Ser Thr Thr Ser Ser Thr Thr Val Thr
65                   70                  75                  80

Leu Gln Met Thr Ser Leu Thr Ala Ala Asp Thr Ala Thr Tyr Phe Cys
                 85                  90                  95

Ala Arg Leu Gly Tyr Ala Asp Tyr Ala Tyr Asp Leu Trp Gly Pro Gly
             100                 105                 110

Thr Leu Val Thr Val Ser Ser
         115
```

-continued

```
<210> SEQ ID NO 15
<211> LENGTH: 117
<212> TYPE: PRT
<213> ORGANISM: rabbit

<400> SEQUENCE: 15

Gln Ser Val Lys Glu Ser Glu Gly Gly Leu Phe Lys Pro Thr Asp Thr
  1               5                  10                  15

Leu Thr Leu Thr Cys Thr Val Ser Gly Phe Ser Leu Arg Asp Asp Ala
             20                  25                  30

Ile Ser Trp Val Arg Gln Ala Pro Gly Asn Gly Leu Glu Trp Leu Gly
         35                  40                  45

Tyr Ile Ser Asp Tyr Gly Asn Thr Tyr Tyr Ala Thr Trp Ala Arg Ser
     50                  55                  60

Arg Ser Thr Ile Thr Arg Asn Thr Asn Glu Asn Thr Val Thr Leu Gln
 65                  70                  75                  80

Met Thr Ser Leu Thr Asp Ala Asp Thr Ala Thr Tyr Phe Cys Ala Arg
                 85                  90                  95

Gly Ser Pro Gly Asn Gly Asp Asn Asp Ile Trp Gly Pro Gly Thr Leu
            100                 105                 110

Val Thr Val Ser Ser
            115

<210> SEQ ID NO 16
<211> LENGTH: 119
<212> TYPE: PRT
<213> ORGANISM: rabbit

<400> SEQUENCE: 16

Gln Leu Val Glu Ser Gly Gly Gly Leu Val Gln Pro Glu Gly Ser Leu
  1               5                  10                  15

Thr Leu Thr Cys Thr Ala Ser Gly Phe Ser Phe Ser Arg Tyr Tyr Tyr
             20                  25                  30

Ile Cys Trp Val Arg Gln Ala Gln Gly Lys Gly Leu Glu Trp Ile Ala
         35                  40                  45

Cys Ile Tyr Ser Gly Val Ser Gly Asp Thr His Tyr Ala Asn Trp Ala
     50                  55                  60

Lys Gly Arg Ile Thr Ile Ser Lys Thr Ser Thr Thr Val Thr Leu
 65                  70                  75                  80

Gln Met Thr Ser Leu Thr Ala Ala Asp Thr Ala Thr Tyr Phe Cys Ala
                 85                  90                  95

Arg Ile Arg Ala Gly Ala Ser Met Tyr Phe Ser Leu Trp Gly Pro Gly
            100                 105                 110

Thr Leu Val Thr Val Ser Ser
            115

<210> SEQ ID NO 17
<211> LENGTH: 121
<212> TYPE: PRT
<213> ORGANISM: rabbit

<400> SEQUENCE: 17

Gln Glu Gln Leu Glu Glu Ser Gly Gly Asp Leu Val Lys Pro Gly Ala
  1               5                  10                  15

Ser Leu Thr Leu Thr Cys Thr Ala Ser Gly Phe Ser Phe Ser Val Gly
             20                  25                  30

Tyr Trp Ile Cys Trp Val Arg Gln Ala Pro Gly Lys Gly Leu Glu Trp
         35                  40                  45
```

```
Ile Ala Cys Ile Asp Ala Gly Thr Ser Gly Gly Thr Tyr Tyr Ala Thr
         50                  55                  60

Trp Ala Lys Gly Arg Phe Thr Ile Ser Lys Thr Ser Thr Thr Val
 65                  70                  75                  80

Thr Leu Gln Met Thr Ser Leu Thr Ala Ala Asp Thr Ala Thr Tyr Phe
                     85                  90                  95

Cys Ala Arg Gly Val Ser Ser Asn Gly Tyr Tyr Phe Lys Leu Trp Gly
                100                 105                 110

Pro Gly Thr Leu Val Thr Val Ser Ser
            115                 120

<210> SEQ ID NO 18
<211> LENGTH: 116
<212> TYPE: PRT
<213> ORGANISM: rabbit

<400> SEQUENCE: 18

Gln Ser Val Glu Glu Ser Gly Gly Arg Leu Val Thr Pro Gly Thr Pro
 1               5                  10                  15

Leu Thr Leu Thr Cys Thr Ala Ser Gly Phe Ser Leu Ser Ser Tyr Tyr
                20                  25                  30

Met Gly Trp Phe Arg Gln Ala Pro Gly Lys Gly Leu Glu Tyr Ile Gly
             35                  40                  45

Phe Ile Asn Thr Asp Gly Arg Ala Tyr Tyr Ala Asn Trp Ala Lys Gly
         50                  55                  60

Arg Phe Thr Ile Ser Lys Thr Ser Thr Thr Val Gly Leu Lys Ile Thr
 65                  70                  75                  80

Ser Pro Thr Thr Glu Asp Thr Ala Thr Tyr Phe Cys Ala Arg Ala Phe
                 85                  90                  95

Gly Ala Asp Ile Gly Leu Tyr Asn Ile Trp Gly Pro Gly Thr Leu Val
                100                 105                 110

Thr Val Ser Ser
            115

<210> SEQ ID NO 19
<211> LENGTH: 116
<212> TYPE: PRT
<213> ORGANISM: rabbit

<400> SEQUENCE: 19

Gln Ser Leu Glu Glu Ser Gly Gly Arg Leu Val Thr Pro Gly Thr Pro
 1               5                  10                  15

Leu Thr Leu Thr Cys Thr Val Ser Gly Phe Ser Leu Ser Arg Tyr Tyr
                20                  25                  30

Met Ser Trp Val Arg Gln Ala Pro Gly Lys Gly Leu Glu Tyr Ile Gly
             35                  40                  45

Ile Ile Thr Thr Ser Gly Arg Lys Tyr Tyr Ala Ser Trp Ala Lys Gly
         50                  55                  60

Arg Phe Thr Ile Ser Lys Thr Ser Thr Thr Val Asp Leu Lys Ile Thr
 65                  70                  75                  80

Ser Leu Thr Ala Ala Asp Thr Ala Thr Tyr Phe Cys Ala Arg Asp Arg
                 85                  90                  95

Ala Gly Asp Ser Leu Asp Phe Asp Pro Trp Gly Pro Gly Thr Leu Val
                100                 105                 110

Thr Val Ser Ser
            115
```

```
<210> SEQ ID NO 20
<211> LENGTH: 118
<212> TYPE: PRT
<213> ORGANISM: rabbit

<400> SEQUENCE: 20

Gln Ser Leu Glu Glu Ser Gly Gly Asp Leu Val Lys Pro Gly Gly Thr
1               5                   10                  15

Leu Thr Leu Thr Cys Lys Ser Ser Gly Phe Asp Phe Ser Thr Asp Ala
            20                  25                  30

Met Cys Trp Val Arg Gln Ala Pro Gly Lys Gly Leu Glu Trp Ile Ala
        35                  40                  45

Cys Ile Tyr Asn Gly Asp Gly Ser Arg Tyr Tyr Ala Ser Trp Ala Lys
    50                  55                  60

Gly Arg Phe Thr Ile Ser Lys Thr Ser Ser Thr Thr Met Thr Leu Gln
65                  70                  75                  80

Met Thr Ser Leu Thr Ala Ala Asp Thr Ala Thr Tyr Phe Cys Ala Arg
                85                  90                  95

Gly Thr Gly Tyr Gly Asp Tyr Gly Phe Val Phe Trp Gly Pro Gly Thr
            100                 105                 110

Leu Val Thr Val Ser Ser
        115

<210> SEQ ID NO 21
<211> LENGTH: 121
<212> TYPE: PRT
<213> ORGANISM: rabbit

<400> SEQUENCE: 21

Gln Glu Gln Leu Glu Glu Ser Gly Gly Asp Leu Val Lys Pro Glu Gly
1               5                   10                  15

Ser Leu Thr Leu Thr Cys Thr Ala Ser Gly Phe Ser Phe Ser Ser Asn
            20                  25                  30

Tyr Trp Met Cys Trp Val Arg Gln Ala Pro Gly Lys Gly Leu Glu Trp
        35                  40                  45

Ile Ala Cys Leu Tyr Thr Gly Ser Ser Gly Thr Thr Tyr Tyr Ala Thr
    50                  55                  60

Trp Ala Lys Gly Arg Phe Thr Ile Ser Lys Pro Ser Ser Thr Thr Val
65                  70                  75                  80

Thr Leu Gln Met Thr Ser Leu Thr Ala Ala Asp Thr Ala Thr Tyr Phe
                85                  90                  95

Cys Ala Arg Asp Pro Tyr Gly Phe Val Tyr Asp Phe Thr Leu Trp Gly
            100                 105                 110

Pro Gly Thr Leu Val Thr Val Ser Ser
        115                 120

<210> SEQ ID NO 22
<211> LENGTH: 120
<212> TYPE: PRT
<213> ORGANISM: rabbit

<400> SEQUENCE: 22

Glu Ser Leu Glu Glu Ser Gly Gly Asp Leu Val Lys Pro Gly Ala Ser
1               5                   10                  15

Leu Thr Leu Thr Cys Lys Ala Ser Gly Val Asp Phe Ser Tyr Tyr Tyr
            20                  25                  30

Tyr Met Cys Trp Val Arg Gln Ala Pro Gly Lys Gly Leu Glu Trp Ile
        35                  40                  45
```

```
Gly Cys Ile Tyr Thr Gly Ser Ser Gly Ser Thr Tyr Tyr Ala Ser Trp
        50                  55                  60

Ala Lys Gly Arg Phe Thr Ile Ser Lys Thr Ser Thr Thr Val Thr
 65                  70                  75                  80

Leu Gln Met Thr Gly Leu Thr Ala Ala Asp Thr Ala Thr Tyr Phe Cys
                    85                  90                  95

Thr Arg Ser Ile Tyr Ile Tyr Gly Tyr Ala Gly Tyr Leu Trp Gly Pro
                100                 105                 110

Gly Thr Leu Val Thr Val Ser Ser
            115                 120

<210> SEQ ID NO 23
<211> LENGTH: 119
<212> TYPE: PRT
<213> ORGANISM: rabbit

<400> SEQUENCE: 23

Gln Leu Glu Glu Ser Gly Gly Gly Leu Val Lys Pro Gly Gly Thr Leu
  1               5                  10                  15

Thr Leu Thr Cys Lys Ala Ser Gly Ile Asp Phe Ser Ser Gly Tyr Tyr
                20                  25                  30

Met Cys Trp Val Arg Gln Ala Pro Gly Lys Gly Leu Glu Leu Ile Ala
            35                  40                  45

Cys Ile Trp Thr Ser Ser Gly Asn Ser Arg Tyr Ala Thr Trp Val Asn
        50                  55                  60

Gly Arg Phe Thr Ile Ser Arg Ser Thr Ser Leu Ser Thr Val Asp Leu
 65                  70                  75                  80

Lys Met Thr Ser Leu Thr Ala Ala Asp Thr Ala Thr Tyr Phe Cys Ala
                85                  90                  95

Ser Ala Gly Thr Tyr Tyr Asn Ile Asp Phe Arg Leu Trp Gly Pro Gly
                100                 105                 110

Thr Leu Val Thr Val Ser Ser
            115

<210> SEQ ID NO 24
<211> LENGTH: 119
<212> TYPE: PRT
<213> ORGANISM: rabbit

<400> SEQUENCE: 24

Gln Ser Val Lys Glu Ser Glu Gly Gly Leu Phe Lys Pro Thr Asp Thr
  1               5                  10                  15

Leu Thr Leu Thr Cys Thr Val Ser Gly Ile Ser Leu Ser Ser Asn Glu
                20                  25                  30

Ile Ser Trp Val Arg Gln Ala Pro Gly Asn Gly Leu Glu Trp Ile Gly
            35                  40                  45

Tyr Val Gly Asn Gly Gly Met Thr His Tyr Ala Ser Trp Ala Lys Ser
        50                  55                  60

Arg Ser Thr Ile Thr Arg Asn Thr Ser Leu Lys Thr Val Thr Leu Lys
 65                  70                  75                  80

Met Thr Ser Leu Thr Ala Ala Asp Thr Gly Thr Tyr Phe Cys Ala Ser
                85                  90                  95

Ser Val Ala Tyr Thr Gly Ile Tyr Tyr Phe Asn Ile Trp Gly Pro Gly
                100                 105                 110

Thr Leu Val Thr Val Ser Ser
            115
```

```
<210> SEQ ID NO 25
<211> LENGTH: 119
<212> TYPE: PRT
<213> ORGANISM: rabbit

<400> SEQUENCE: 25

Gln Ser Val Lys Glu Ser Glu Gly Gly Leu Phe Lys Pro Thr Asp Thr
1               5                   10                  15

Leu Thr Leu Thr Cys Thr Val Ser Gly Phe Ser Leu Asn Ser Asn Glu
            20                  25                  30

Ile Ser Trp Val Arg Gln Ala Pro Gly Asn Gly Leu Glu Trp Ile Gly
        35                  40                  45

Tyr Ile Gly Asn Gly Gly Met Thr His Tyr Ala Ser Trp Ala Lys Gly
    50                  55                  60

Arg Ser Thr Ile Thr Arg Asp Thr Asn Leu Asn Thr Val Thr Leu Lys
65                  70                  75                  80

Met Thr Ser Leu Thr Ala Ala Asp Thr Ala Thr Tyr Phe Cys Ala Ser
                85                  90                  95

Ser Val Glu Tyr Thr Asp Leu Tyr Tyr Leu Asn Ile Trp Gly Pro Gly
            100                 105                 110

Thr Leu Val Thr Val Ser Ser
        115

<210> SEQ ID NO 26
<211> LENGTH: 120
<212> TYPE: PRT
<213> ORGANISM: rabbit

<400> SEQUENCE: 26

Gln Ser Leu Glu Glu Ser Gly Gly Asp Leu Val Lys Pro Gly Ala Ser
1               5                   10                  15

Leu Thr Leu Thr Cys Thr Ala Ser Gly Phe Thr Leu Ser Ser Tyr Tyr
            20                  25                  30

Met Cys Trp Val Arg Gln Ala Pro Gly Lys Gly Leu Glu Trp Ile Ala
        35                  40                  45

Cys Ile Tyr Ala Ala Val Asn Gly Gly Thr Asn Tyr Ala Ser Trp Ala
    50                  55                  60

Lys Gly Arg Phe Thr Ile Ser Lys Thr Ser Thr Thr Val Thr Leu
65                  70                  75                  80

Gln Met Thr Ser Leu Thr Ala Ala Asp Thr Ala Thr Tyr Phe Cys Ala
                85                  90                  95

Arg Phe Tyr Ala Gly Val Ser Tyr Thr Thr Leu Asp Leu Trp Gly Gln
            100                 105                 110

Gly Thr Leu Val Thr Val Ser Ser
        115                 120

<210> SEQ ID NO 27
<211> LENGTH: 120
<212> TYPE: PRT
<213> ORGANISM: rabbit

<400> SEQUENCE: 27

Gln Ser Leu Glu Glu Ser Gly Gly Asp Leu Val Lys Pro Gly Ala Ser
1               5                   10                  15

Leu Thr Leu Thr Cys Thr Ala Ser Gly Leu Ser Phe Ser Ser Tyr Tyr
            20                  25                  30

Met Cys Trp Val Arg Gln Ala Pro Gly Lys Gly Leu Glu Trp Ile Gly
        35                  40                  45
```

Cys Ile Tyr Ala Ala Thr Asn Gly Asn Thr Glu Tyr Ala Ser Trp Ala
        50                  55                  60

Lys Gly Arg Phe Thr Ile Ser Lys Thr Ser Thr Thr Val Thr Leu
65                  70                  75                  80

Gln Met Thr Gly Leu Thr Ala Ala Asp Thr Ala Thr Tyr Phe Cys Ala
                85                  90                  95

Arg Phe Ala Ala Gly Tyr Ser Tyr Thr Thr Leu Asp Leu Trp Gly Gln
            100                 105                 110

Gly Thr Leu Val Thr Val Ser Ser
            115                 120

<210> SEQ ID NO 28
<211> LENGTH: 121
<212> TYPE: PRT
<213> ORGANISM: rabbit

<400> SEQUENCE: 28

Gln Ser Leu Glu Glu Ser Gly Gly Asp Leu Val Lys Pro Gly Ala Ser
1               5                   10                  15

Leu Thr Leu Thr Cys Thr Ala Ser Gly Phe Ser Phe Ser Ser Ser Ile
                20                  25                  30

Tyr Met Cys Trp Val Arg Gln Ala Pro Gly Lys Gly Pro Glu Trp Ile
            35                  40                  45

Ala Cys Ile Ala Ala Gly Gly Ser Thr Ser Thr Tyr Tyr Ala Ser Trp
        50                  55                  60

Ala Lys Gly Arg Phe Thr Val Ser Lys Ala Ser Ser Thr Thr Val Thr
65                  70                  75                  80

Leu Gln Met Thr Ser Leu Thr Val Ala Asp Thr Ala Thr Tyr Phe Cys
                85                  90                  95

Ala Arg Asp Ala Asp Gly Asp Gly Gly Trp Val Phe Asn Leu Trp Gly
            100                 105                 110

Pro Gly Thr Leu Val Thr Val Ser Ser
            115                 120

<210> SEQ ID NO 29
<211> LENGTH: 120
<212> TYPE: PRT
<213> ORGANISM: rabbit

<400> SEQUENCE: 29

Gln Ser Val Lys Glu Ser Glu Gly Gly Leu Phe Lys Pro Thr Asp Thr
1               5                   10                  15

Leu Thr Leu Thr Cys Thr Val Ser Gly Phe Ser Leu Ser Arg Tyr Gly
                20                  25                  30

Val Ser Trp Val Arg Gln Ala Pro Gly Ser Gly Leu Gln Trp Ile Gly
            35                  40                  45

Ala Ile Gly Glu Thr Gly Arg Ala Tyr Tyr Ala Asn Trp Ala Lys Ser
        50                  55                  60

Arg Ser Thr Ile Thr Arg Asn Thr Asn Val Asn Thr Val Thr Leu Lys
65                  70                  75                  80

Met Thr Ser Leu Thr Ala Ala Asp Thr Ala Thr Tyr Phe Cys Ala Arg
                85                  90                  95

Gly Glu Glu Phe Asn Asn Gly Trp Gly Ala Phe Asn Ile Trp Gly Pro
            100                 105                 110

Gly Thr Leu Val Thr Val Ser Ser
            115                 120

```
<210> SEQ ID NO 30
<211> LENGTH: 120
<212> TYPE: PRT
<213> ORGANISM: rabbit

<400> SEQUENCE: 30

Gln Ser Val Lys Glu Ser Glu Gly Gly Leu Phe Lys Pro Ala Asp Thr
 1               5                  10                  15

Leu Thr Leu Thr Cys Thr Val Ser Gly Phe Ser Leu Ser Arg Tyr Gly
            20                  25                  30

Val Ser Trp Val Arg Gln Ala Pro Gly Asn Gly Leu Glu Trp Ile Gly
        35                  40                  45

Thr Ile Gly Glu Ala Gly Arg Ala Tyr Tyr Ala Asn Trp Ala Arg Ser
    50                  55                  60

Arg Ser Thr Ile Thr Arg Thr Thr Asn Leu Asn Thr Val Thr Leu Thr
65                  70                  75                  80

Met Thr Ser Leu Thr Ala Ala Asp Thr Ala Thr Tyr Phe Cys Ala Arg
                85                  90                  95

Gly Glu Val Phe Asn Asn Gly Trp Gly Ala Phe Asn Ile Trp Gly Pro
            100                 105                 110

Gly Thr Leu Val Thr Val Ser Ser
        115                 120

<210> SEQ ID NO 31
<211> LENGTH: 120
<212> TYPE: PRT
<213> ORGANISM: rabbit

<400> SEQUENCE: 31

Gln Ser Val Lys Glu Ser Glu Gly Gly Leu Phe Lys Pro Thr Asp Thr
 1               5                  10                  15

Leu Thr Leu Thr Cys Thr Val Ser Gly Phe Ser Leu Ser Arg Tyr Gly
            20                  25                  30

Ile Asn Trp Val Arg Gln Ala Pro Gly Ser Gly Leu Gln Trp Ile Gly
        35                  40                  45

Ala Ile Gly Glu Thr Gly Arg Ala Tyr Phe Ala Ser Trp Ala Lys Ser
    50                  55                  60

Arg Ser Thr Ile Thr Arg Asn Thr Asn Leu Asn Thr Val Thr Leu Arg
65                  70                  75                  80

Met Thr Ser Leu Thr Ala Ala Asp Thr Ala Thr Tyr Phe Cys Ala Arg
                85                  90                  95

Gly Glu Leu Phe Asn Asn Gly Trp Gly Ala Phe Asn Ile Trp Gly Pro
            100                 105                 110

Gly Thr Leu Val Thr Val Ser Ser
        115                 120

<210> SEQ ID NO 32
<211> LENGTH: 120
<212> TYPE: PRT
<213> ORGANISM: rabbit

<400> SEQUENCE: 32

Gln Ser Val Lys Glu Ser Glu Gly Gly Leu Phe Lys Pro Thr Asp Thr
 1               5                  10                  15

Leu Thr Leu Thr Cys Thr Val Ser Gly Phe Ser Leu Ser Arg Tyr Gly
            20                  25                  30

Val Thr Trp Val Arg Gln Ala Pro Gly Asn Gly Leu Gln Trp Ile Gly
        35                  40                  45
```

```
Thr Ile Gly Glu Thr Gly Arg Ser Tyr Tyr Ala Ser Trp Ala Lys Ser
         50                  55                  60

Arg Ser Thr Val Thr Arg Asn Thr Asn Glu Asn Thr Val Thr Leu Lys
 65                  70                  75                  80

Met Thr Ser Leu Thr Ala Ala Asp Thr Ala Thr Tyr Phe Cys Ala Arg
                 85                  90                  95

Gly Glu Leu Phe Asn Asn Gly Trp Gly Ala Phe Asn Ile Trp Gly Pro
                100                 105                 110

Gly Thr Leu Val Thr Val Ser Ser
            115                 120

<210> SEQ ID NO 33
<211> LENGTH: 118
<212> TYPE: PRT
<213> ORGANISM: rabbit

<400> SEQUENCE: 33

Gln Ser Leu Glu Glu Ser Gly Gly Arg Leu Val Thr Pro Gly Thr Pro
 1               5                  10                  15

Leu Thr Leu Thr Cys Thr Val Ser Gly Ile Asp Leu Ser Ser Tyr His
                 20                  25                  30

Met Cys Trp Val Arg Gln Ala Pro Gly Lys Gly Leu Glu Tyr Ile Gly
             35                  40                  45

Ile Ile Asn Arg Asn Arg Lys Thr Gly Tyr Ala Asn Trp Ala Lys Gly
         50                  55                  60

Arg Phe Thr Ile Ser Arg Thr Ser Thr Thr Val Asp Leu Glu Ile Thr
 65                  70                  75                  80

Ser Pro Thr Thr Glu Asp Thr Ala Thr Tyr Phe Cys Ala Arg Asp Asn
                 85                  90                  95

Tyr Asp Glu Tyr Asp Asn Asn Val Phe Asp Leu Trp Ser Pro Gly Thr
                100                 105                 110

Leu Val Thr Val Ser Ser
            115

<210> SEQ ID NO 34
<211> LENGTH: 118
<212> TYPE: PRT
<213> ORGANISM: rabbit

<400> SEQUENCE: 34

Gln Ser Val Glu Glu Ser Gly Gly Arg Leu Val Thr Pro Gly Thr Pro
 1               5                  10                  15

Leu Thr Leu Thr Cys Thr Val Ser Gly Phe Ser Leu Ser Thr Tyr Asn
                 20                  25                  30

Met Ile Trp Val Arg Gln Ala Pro Gly Lys Gly Leu Glu Trp Ile Gly
             35                  40                  45

Tyr Ile Asp Val Val Gly Ala Thr Tyr Tyr Ala Ser Trp Val Lys Gly
         50                  55                  60

Arg Phe Thr Ile Ser Lys Thr Ser Thr Thr Val Asp Leu Lys Val Thr
 65                  70                  75                  80

Ser Pro Thr Thr Glu Asp Thr Ala Thr Tyr Phe Cys Val Arg Glu Ala
                 85                  90                  95

Gly Gly Gln Thr Ala Tyr Tyr Gly Leu Ala Pro Trp Gly Pro Gly Thr
                100                 105                 110

Leu Val Thr Val Ser Ser
            115
```

```
<210> SEQ ID NO 35
<211> LENGTH: 120
<212> TYPE: PRT
<213> ORGANISM: rabbit

<400> SEQUENCE: 35

Gln Leu Val Glu Ser Gly Gly Gly Leu Val Gln Ala Gly Glu Ser Leu
  1               5                  10                  15

Lys Leu Ser Cys Lys Ala Ser Gly Ile Asp Phe Ser Asn Tyr Gly Ile
             20                  25                  30

Thr Trp Val Arg Gln Ala Pro Gly Lys Gly Leu Glu Trp Ile Ala Tyr
         35                  40                  45

Ile Tyr Leu Gly Phe Gly Ile Thr Asp Tyr Ala Asn Ser Val Lys Gly
 50                  55                  60

Gln Phe Thr Ile Ser Ser Asp Asn Ala Gln Asn Thr Val Phe Leu Gln
 65                  70                  75                  80

Met Thr Gly Leu Thr Ala Ser Asp Thr Ala Thr Tyr Phe Cys Ala Ser
                 85                  90                  95

Asp Pro Val Tyr Ser Ser Ser Gly Tyr Leu Asn Leu Trp Gly Pro
            100                 105                 110

Gly Thr Leu Val Thr Val Ser Ser
            115                 120

<210> SEQ ID NO 36
<211> LENGTH: 119
<212> TYPE: PRT
<213> ORGANISM: rabbit

<400> SEQUENCE: 36

Gln Ser Val Glu Glu Ser Gly Gly Arg Leu Val Ala Pro Gly Thr Pro
  1               5                  10                  15

Leu Thr Leu Thr Cys Thr Val Ser Gly Phe Ser Leu Ser Ser Gly Ala
             20                  25                  30

Met Ser Trp Val Arg Gln Ala Pro Gly Lys Gly Leu Glu Trp Ile Gly
         35                  40                  45

Val Ile Ile Ser Ser Gly Ala Thr Tyr Tyr Ala Ser Trp Ala Lys Gly
 50                  55                  60

Arg Phe Thr Ile Ser Lys Thr Ser Thr Thr Val Asp Leu Lys Ile Thr
 65                  70                  75                  80

Ser Pro Thr Thr Glu Asp Thr Ala Ile Tyr Phe Cys Ala Arg Gly Gly
                 85                  90                  95

Pro Asp Asp Ser Asn Ser Met Gly Thr Phe Asp Pro Trp Gly Pro Gly
            100                 105                 110

Thr Leu Val Thr Val Ser Ser
        115

<210> SEQ ID NO 37
<211> LENGTH: 123
<212> TYPE: PRT
<213> ORGANISM: rabbit

<400> SEQUENCE: 37

Gln Ser Leu Val Glu Ser Gly Gly Gly Leu Val Lys Pro Gly Ala Ser
  1               5                  10                  15

Leu Thr Leu Thr Cys Lys Ala Ser Gly Phe Ser Phe Ser Ser Gly Asp
             20                  25                  30

Asp Met Cys Trp Val Arg Gln Ala Pro Gly Lys Gly Leu Glu Trp Ile
         35                  40                  45
```

```
Ala Cys Met Ser Pro Gly Val Ser Gly Ser Thr Tyr Tyr Pro Ser Trp
        50                  55                  60

Ala Lys Gly Arg Phe Thr Ile Ala Lys Thr Ser Ser Thr Thr Val Thr
 65                  70                  75                  80

Leu Gln Met Thr Ser Leu Thr Ala Ala Asp Thr Ala Thr Tyr Phe Cys
                 85                  90                  95

Ala Thr Ala Asp Gly Gly Gly Ser Asp Tyr Tyr Trp Gly Phe Asn Leu
            100                 105                 110

Trp Gly Pro Gly Thr Leu Val Thr Val Ser Ser
            115                 120
```

<210> SEQ ID NO 38
<211> LENGTH: 123
<212> TYPE: PRT
<213> ORGANISM: rabbit

<400> SEQUENCE: 38

```
Val Gln Leu Glu Glu Ser Gly Gly Asp Leu Val Lys Pro Gly Ala Ser
  1               5                  10                  15

Gln Thr Leu Thr Cys Thr Ala Ser Gly Ile Asp Phe Ser Ala Gly His
                 20                  25                  30

Tyr Met Cys Trp Val Arg Gln Ala Pro Gly Lys Gly Leu Glu Trp Ile
             35                  40                  45

Ala Cys Arg Tyr Val Gly Asn Ser Asp Asn Thr Tyr Tyr Ala Ser Trp
        50                  55                  60

Ala Lys Gly Arg Phe Ile Ile Ser Lys Thr Ser Ser Thr Thr Val Asp
 65                  70                  75                  80

Leu Gln Met Thr Ser Leu Thr Val Ala Asp Thr Ala Thr Tyr Phe Cys
                 85                  90                  95

Ala Arg Ala Gly Tyr Asp Ile Arg Ser Ser Ala Tyr Val Pro Lys Leu
            100                 105                 110

Trp Gly Pro Gly Thr Leu Val Thr Val Ser Ser
            115                 120
```

<210> SEQ ID NO 39
<211> LENGTH: 124
<212> TYPE: PRT
<213> ORGANISM: rabbit

<400> SEQUENCE: 39

```
Val Gln Leu Glu Glu Ser Gly Gly Asp Leu Val Lys Pro Gly Ala Ser
  1               5                  10                  15

Leu Thr Leu Thr Cys Thr Ala Ser Gly Ile Asp Leu Ser Arg Tyr Tyr
                 20                  25                  30

Tyr Ile Cys Trp Val Arg Gln Ala Pro Gly Lys Gly Leu Glu Trp Ile
             35                  40                  45

Gly Cys Ile Asn Thr Gly Val Gly Asn Gly Tyr Tyr Ala Ser Trp Ala
        50                  55                  60

Lys Gly Arg Ile Ile Thr Ser Lys Thr Ser Ser Thr Thr Val Thr Leu
 65                  70                  75                  80

Gln Met Thr Ser Leu Thr Ala Ala Asp Thr Ala Thr Tyr Phe Cys Ala
                 85                  90                  95

Arg Gly Val Gly Ser Gly Ser Ala Ile Tyr Met Gly Ala Tyr Phe Asp
            100                 105                 110

Leu Trp Gly Pro Gly Thr Leu Val Thr Val Ser Ser
            115                 120
```

```
<210> SEQ ID NO 40
<211> LENGTH: 123
<212> TYPE: PRT
<213> ORGANISM: rabbit

<400> SEQUENCE: 40

Gln Leu Glu Glu Ser Gly Gly Asp Leu Val Lys Pro Gly Ala Ser Leu
 1               5                  10                  15

Thr Leu Thr Cys Thr Ala Ser Gly Ile Asp Leu Ser Arg Tyr Tyr Tyr
            20                  25                  30

Met Cys Trp Val Arg Gln Ala Pro Gly Lys Gly Leu Glu Trp Ile Gly
        35                  40                  45

Cys Leu Asn Ser Gly Ser Gly Asp Thr Phe Ser Ala Arg Trp Ala Lys
    50                  55                  60

Gly Arg Phe Val Ile Phe Lys Thr Ser Ser Thr Thr Val Asp Leu Lys
65                  70                  75                  80

Met Thr Ser Leu Thr Ala Ala Asp Ala Ala Thr Tyr Phe Cys Ala Arg
                85                  90                  95

Gly Tyr Gly Ser Ala Ser Ala Ile Tyr Met Gly Ala Tyr Phe Asp Ser
            100                 105                 110

Trp Gly Pro Gly Thr Leu Val Thr Val Ser Ser
        115                 120

<210> SEQ ID NO 41
<211> LENGTH: 120
<212> TYPE: PRT
<213> ORGANISM: rabbit

<400> SEQUENCE: 41

Glu Ser Gly Gly Gly Leu Val Lys Pro Gly Ala Ser Leu Thr Leu Thr
 1               5                  10                  15

Cys Lys Ala Ser Gly Ile Asp Leu Ser Arg Tyr Tyr Trp Ile Cys Trp
            20                  25                  30

Val Arg Gln Ala Pro Gly Lys Gly Leu Glu Trp Ile Gly Cys Ile Asn
        35                  40                  45

Ser Gly Ser Gly Tyr Thr Tyr Tyr Ala Asn Trp Ala Lys Gly Arg Phe
    50                  55                  60

Ile Ile Ser Lys Thr Ser Ser Thr Thr Val Thr Leu Gln Met Thr Ser
65                  70                  75                  80

Leu Thr Ala Ala Asp Thr Ala Thr Tyr Phe Cys Ala Arg Gly Tyr Gly
                85                  90                  95

Ser Gly Ser Asn Ile Tyr Met Gly Ala Tyr Phe Asp Leu Trp Gly Pro
            100                 105                 110

Gly Thr Leu Val Thr Val Ser Ser
        115                 120

<210> SEQ ID NO 42
<211> LENGTH: 124
<212> TYPE: PRT
<213> ORGANISM: rabbit

<400> SEQUENCE: 42

Gln Glu Gln Leu Lys Glu Thr Gly Gly Gly Leu Val Gln Pro Gly Gly
 1               5                  10                  15

Ser Leu Thr Leu Thr Cys Lys Ala Ser Gly Phe Asp Phe Ser Arg Tyr
            20                  25                  30

Trp Met Ser Trp Val Arg Gln Ala Pro Gly Lys Gly Leu Glu Trp Ile
        35                  40                  45
```

```
Gly Ile Ile Asn Thr Gly Gly Asn Thr Tyr Tyr Ala Thr Trp Val Asn
            50                  55                  60

Gly Arg Phe Thr Ile Ser Ser Asp Asn Ala Gln Asn Thr Val Asp Leu
 65                  70                  75                  80

Gln Met Asn Ser Leu Thr Ala Ala Asp Thr Ala Thr Tyr Phe Cys Ala
                 85                  90                  95

Arg Gly Tyr Ala Gly Tyr Gly Gly Tyr Gly Arg Pro Val Asn Phe Asn
            100                 105                 110

Leu Trp Gly Pro Gly Thr Leu Val Thr Val Ser Ser
            115                 120

<210> SEQ ID NO 43
<211> LENGTH: 124
<212> TYPE: PRT
<213> ORGANISM: rabbit

<400> SEQUENCE: 43

Gln Ser Leu Glu Glu Ser Gly Gly Asp Leu Val Lys Pro Gly Ala Ser
 1               5                  10                  15

Leu Thr Leu Thr Cys Thr Ala Ser Glu Ile Asp Phe Ser Arg Tyr Tyr
                 20                  25                  30

Trp Ile Cys Trp Val Arg Gln Ala Pro Gly Lys Gly Leu Glu Trp Ile
             35                  40                  45

Gly Cys Ile Asn Ser Gly Ser Gly Ser Ser Tyr Tyr Ala Thr Trp Ala
            50                  55                  60

Lys Gly Arg Phe Thr Val Ser Lys Thr Ser Thr Thr Val Thr Leu
 65                  70                  75                  80

Gln Met Thr Ser Leu Thr Ala Ala Asp Thr Ala Thr Tyr Phe Cys Ala
                 85                  90                  95

Arg Gly Phe Gly Ser Ser Ser Asn Tyr Tyr Ile Gly Ile Tyr Phe Asn
            100                 105                 110

Leu Trp Gly Pro Gly Thr Leu Val Thr Val Ser Ser
            115                 120

<210> SEQ ID NO 44
<211> LENGTH: 123
<212> TYPE: PRT
<213> ORGANISM: rabbit

<400> SEQUENCE: 44

Gln Ser Val Glu Glu Ser Gly Gly Arg Leu Val Thr Pro Gly Thr Pro
 1               5                  10                  15

Leu Thr Leu Thr Cys Thr Ala Ser Gly Phe Ser Leu Ser His Tyr Tyr
                 20                  25                  30

Ile Gly Trp Val Arg Gln Thr Pro Gly Lys Gly Leu Glu Trp Ile Gly
             35                  40                  45

Leu Ile Asp Val Tyr Ser Gly Asn Ile Tyr Tyr Ala Ser Trp Ala Lys
            50                  55                  60

Gly Arg Phe Thr Ile Ser Lys Ala Ser Thr Thr Val Asp Leu Lys Val
 65                  70                  75                  80

Ala Ser Pro Thr Thr Glu Asp Thr Ala Thr Tyr Phe Cys Ala Arg Tyr
                 85                  90                  95

Gly Tyr Asp Thr Tyr Gly Asp Tyr Ser Phe Ser Arg Leu Asp Leu
            100                 105                 110

Trp Gly Gln Gly Thr Leu Val Thr Val Ser Ser
            115                 120
```

```
<210> SEQ ID NO 45
<211> LENGTH: 112
<212> TYPE: PRT
<213> ORGANISM: rabbit

<400> SEQUENCE: 45

Gln Val Leu Thr Gln Thr Pro Ser Pro Val Ser Ala Ala Val Gly Gly
 1               5                  10                  15

Thr Val Thr Ile Asn Cys Gln Ser Ser Gln Ser Val Asp Ser Asp Val
            20                  25                  30

Cys Leu Ala Trp Tyr Gln Gln Lys Pro Gly Gln Pro Pro Lys Leu Leu
        35                  40                  45

Ile Tyr Arg Ala Ser Lys Leu Ala Ser Gly Val Ser Ala Arg Phe Ser
    50                  55                  60

Gly Ser Gly Ser Gly Thr Gln Phe Thr Leu Thr Ile Ser Asp Val Gln
65                  70                  75                  80

Cys Asp Asp Ala Ala Thr Tyr Tyr Cys Gln Gly Ile Tyr Thr Gly Ser
                85                  90                  95

Thr Trp Tyr Arg Asn Ala Phe Gly Gly Gly Thr Glu Val Val Val Lys
            100                 105                 110

<210> SEQ ID NO 46
<211> LENGTH: 109
<212> TYPE: PRT
<213> ORGANISM: rabbit

<400> SEQUENCE: 46

Leu Val Met Thr Gln Thr Pro Ala Ser Val Glu Ala Ala Val Gly Gly
 1               5                  10                  15

Thr Val Thr Ile Lys Cys Gln Ala Ser Gln Asn Ile Tyr Tyr Lys Leu
            20                  25                  30

Ala Trp Tyr Gln Gln Lys Pro Gly Gln Pro Pro Lys Leu Leu Ile Tyr
        35                  40                  45

Asp Ala Ser Asp Leu Ala Ser Gly Val Pro Ser Arg Phe Lys Gly Ser
    50                  55                  60

Gly Ser Gly Thr Glu Phe Thr Leu Thr Ile Ser Gly Val Gln Cys Asp
65                  70                  75                  80

Asp Ala Ala Thr Tyr Tyr Cys Gln Gln Gly Phe Ser Thr Asn Glu Ile
                85                  90                  95

Asp Asn Thr Phe Gly Gly Gly Thr Glu Val Val Val Lys
            100                 105

<210> SEQ ID NO 47
<211> LENGTH: 112
<212> TYPE: PRT
<213> ORGANISM: rabbit

<400> SEQUENCE: 47

Glu Val Val Met Thr Gln Thr Pro Ala Ser Val Ser Ala Ala Val Gly
 1               5                  10                  15

Asp Thr Val Thr Ile Lys Cys Gln Ala Ser Gln Ser Ile Tyr Asn Tyr
            20                  25                  30

Leu Ser Trp Tyr Gln Gln Lys Pro Gly Gln Pro Pro Lys Leu Leu Met
        35                  40                  45

Tyr Ile Ser Ser Asn Leu Ala Ser Gly Val Pro Ser Arg Phe Lys Gly
    50                  55                  60

Ser Gly Ser Gly Thr Glu Tyr Thr Leu Thr Ile Ser Asp Leu Glu Cys
65                  70                  75                  80
```

Asp Asp Ala Ala Thr Tyr Tyr Cys Gln Thr Asn Tyr Phe Ile Ser Ala
            85                  90                  95

Thr Ser Pro Gly Arg Ala Phe Gly Gly Gly Thr Glu Val Val Val Lys
        100                 105                 110

<210> SEQ ID NO 48
<211> LENGTH: 112
<212> TYPE: PRT
<213> ORGANISM: rabbit

<400> SEQUENCE: 48

Glu Val Val Met Thr Gln Thr Pro Ala Ser Val Glu Ala Ala Val Gly
 1               5                  10                  15

Gly Thr Val Thr Ile Lys Cys Gln Ala Ser Gln Ser Ile Tyr Ser Tyr
            20                  25                  30

Leu Ser Trp Tyr Gln Gln Lys Pro Gly Gln Pro Pro Lys Leu Leu Phe
        35                  40                  45

Tyr Lys Thr Ser Thr Leu Ala Ser Gly Val Pro Ser Arg Phe Lys Gly
    50                  55                  60

Ser Gly Ser Gly Thr Glu Tyr Thr Leu Thr Ile Ser Asp Leu Glu Cys
65                  70                  75                  80

Ala Asp Ala Ala Thr Tyr Tyr Cys Gln Thr Asn Tyr Phe Arg Thr Ser
                85                  90                  95

Ser Asp Pro Gly Arg Ala Phe Gly Gly Gly Thr Glu Val Val Val Lys
        100                 105                 110

<210> SEQ ID NO 49
<211> LENGTH: 110
<212> TYPE: PRT
<213> ORGANISM: rabbit

<400> SEQUENCE: 49

Val Val Leu Thr Gln Thr Ala Ser Pro Met Ser Glu Pro Val Gly Gly
 1               5                  10                  15

Thr Val Thr Ile Lys Cys Gln Ala Ser Gln Ser Ile Gly Ser Asn Leu
            20                  25                  30

Ala Trp Tyr Gln Gln Lys Pro Gly Gln Pro Pro Lys Leu Leu Ile Tyr
        35                  40                  45

Lys Ala Ser Thr Leu Ala Ser Gly Val Pro Ser Arg Phe Ser Gly Ser
    50                  55                  60

Arg Ser Gly Thr Glu Phe Thr Leu Thr Ile Ser Asp Leu Glu Cys Ala
65                  70                  75                  80

Asp Ala Ala Thr Tyr Tyr Cys Gln Gly Tyr Tyr Tyr Ser Asp Ser Thr
                85                  90                  95

Asp Ser Phe Val Phe Gly Gly Gly Thr Glu Val Val Val Lys
        100                 105                 110

<210> SEQ ID NO 50
<211> LENGTH: 114
<212> TYPE: PRT
<213> ORGANISM: rabbit

<400> SEQUENCE: 50

Asp Pro Val Met Thr Gln Thr Pro Ser Ser Thr Ser Ala Ser Val Gly
 1               5                  10                  15

Gly Thr Val Thr Ile Asn Cys Gln Ser Thr Glu Ser Val Tyr Lys Asn
            20                  25                  30

Asn Tyr Leu Ala Trp Tyr Gln Gln Lys Pro Gly Gln Pro Pro Lys Gln
        35                  40                  45

Leu Ile Tyr Asp Ala Ser Thr Leu Ala Ser Gly Val Pro Ser Arg Phe
                50                  55                  60

Lys Gly Ser Gly Ser Gly Thr Gln Phe Thr Leu Thr Ile Ser Gly Met
 65                  70                  75                  80

Gln Cys Asp Asp Ala Ala Thr Tyr Tyr Cys Ala Gly Tyr Trp Arg Ser
                    85                  90                  95

Gly Tyr Gly Thr Ala Asn Gly Ser Phe Gly Gly Gly Thr Glu Val Val
                100                 105                 110

Val Glu

<210> SEQ ID NO 51
<211> LENGTH: 114
<212> TYPE: PRT
<213> ORGANISM: rabbit

<400> SEQUENCE: 51

Asp Pro Val Met Thr Gln Thr Pro Ser Ser Thr Ser Ala Ala Val Gly
 1               5                  10                  15

Gly Thr Val Thr Ile Asn Cys Gln Ser Thr Glu Ser Val Tyr Lys Asn
                20                  25                  30

Asn Tyr Leu Ala Trp Tyr Gln Gln Lys Ala Gly Gln Pro Pro Lys Gln
                35                  40                  45

Leu Ile Tyr Asp Ala Ser Ser Leu Ala Ser Gly Val Pro Ser Arg Phe
                50                  55                  60

Lys Gly Ser Gly Ser Gly Thr Gln Phe Thr Leu Thr Ile Ser Gly Val
 65                  70                  75                  80

Gln Cys Ala Asp Ala Ala Thr Tyr Tyr Cys Ala Gly Tyr Phe Arg Ser
                    85                  90                  95

Gly Ser Gly Thr Ala Asn Gly Ser Phe Gly Gly Gly Thr Glu Val Val
                100                 105                 110

Val Lys

<210> SEQ ID NO 52
<211> LENGTH: 114
<212> TYPE: PRT
<213> ORGANISM: rabbit

<400> SEQUENCE: 52

Asp Pro Val Met Thr Gln Thr Pro Ser Ser Thr Ser Ala Ala Val Gly
 1               5                  10                  15

Gly Thr Val Thr Ile Asn Cys Gln Ser Thr Glu Ser Val Tyr Lys Asn
                20                  25                  30

Asn Tyr Leu Ala Trp Tyr Gln Gln Lys Pro Gly Gln Pro Pro Lys Gln
                35                  40                  45

Leu Ile Tyr Asp Ala Ser Thr Leu Ala Ser Gly Val Pro Ser Arg Phe
                50                  55                  60

Lys Gly Ser Gly Ser Gly Thr Asn Phe Thr Leu Thr Ile Ser Gly Val
 65                  70                  75                  80

Gln Cys Asp Asp Ala Ala Thr Tyr Tyr Cys Ala Gly Tyr Tyr Arg Ser
                    85                  90                  95

Gly Phe Gly Thr Ala Asn Gly Ser Phe Gly Glu Gly Thr Glu Val Val
                100                 105                 110

Val Lys

<210> SEQ ID NO 53
<211> LENGTH: 114

```
<212> TYPE: PRT
<213> ORGANISM: rabbit

<400> SEQUENCE: 53

Asp Pro Val Met Thr Gln Thr Pro Ser Ser Thr Ser Ala Ala Val Gly
 1               5                  10                  15

Gly Thr Val Thr Ile Asn Cys Gln Ser Thr Glu Ser Val Tyr Lys Asn
                20                  25                  30

Asn Tyr Leu Ala Trp Tyr Gln Gln Lys Pro Gly Gln Pro Pro Lys Leu
            35                  40                  45

Leu Ile Tyr Asp Ala Ser Thr Leu Ala Ser Gly Val Pro Ser Arg Phe
        50                  55                  60

Lys Ala Ser Gly Ser Gly Thr Gln Phe Thr Leu Thr Ile Ser Gly Val
 65                  70                  75                  80

Gln Cys Asp Asp Ala Ala Thr Tyr Tyr Cys Ala Gly Tyr Tyr Arg Ser
                85                  90                  95

Gly Ser Gly Thr Ala Asn Gly Ser Phe Gly Gly Gly Thr Glu Val Val
               100                 105                 110

Val Lys

<210> SEQ ID NO 54
<211> LENGTH: 114
<212> TYPE: PRT
<213> ORGANISM: rabbit

<400> SEQUENCE: 54

Asp Pro Val Met Thr Gln Thr Pro Ser Ser Thr Ser Ala Ser Val Gly
 1               5                  10                  15

Gly Thr Val Thr Ile Asn Cys Gln Ser Thr Glu Ser Val Tyr Lys Asn
                20                  25                  30

Asn Tyr Leu Ala Trp Tyr Gln Gln Lys Pro Gly Gln Pro Pro Lys Gln
            35                  40                  45

Leu Ile Tyr Asp Ala Ser Thr Leu Asn Ser Gly Val Pro Ser Arg Phe
        50                  55                  60

Lys Gly Ser Gly Ser Gly Thr Gln Phe Thr Leu Thr Ile Ser Gly Val
 65                  70                  75                  80

Gln Cys Asp Asp Ala Ala Thr Tyr Tyr Cys Ala Gly Tyr Trp Tyr Ser
                85                  90                  95

Gly Ser Gly Thr Ala Asn Gly Ser Phe Gly Gly Gly Thr Glu Val Val
               100                 105                 110

Val Lys

<210> SEQ ID NO 55
<211> LENGTH: 112
<212> TYPE: PRT
<213> ORGANISM: rabbit

<400> SEQUENCE: 55

Asp Ile Val Met Thr Gln Thr Pro Ala Ser Ala Ser Glu Pro Val Gly
 1               5                  10                  15

Gly Thr Val Thr Ile Asn Cys Gln Ala Ser Gln Asn Ile Tyr Asn Thr
                20                  25                  30

Leu Ala Trp Tyr Gln Gln Lys Pro Gly Gln Pro Pro Lys Leu Leu Met
            35                  40                  45

Ser Leu Ala Ser Thr Leu Glu Ser Gly Val Pro Ser Arg Phe Lys Gly
        50                  55                  60

Ser Gly Ser Gly Thr Glu Phe Thr Leu Thr Ile Ser Asp Leu Glu Cys
```

```
                65                  70                  75                  80
Ala Asp Ala Ala Thr Tyr Tyr Cys Gln Ser Asn His Gly Ser Asn Ser
                    85                  90                  95

Asp Ser Tyr Gly Asn Thr Phe Gly Gly Gly Thr Glu Val Val Val Lys
            100                 105                 110

<210> SEQ ID NO 56
<211> LENGTH: 112
<212> TYPE: PRT
<213> ORGANISM: rabbit

<400> SEQUENCE: 56

Asp Ile Val Met Thr Gln Thr Pro Ala Ser Ala Ser Glu Pro Val Gly
1               5                   10                  15

Gly Thr Val Thr Ile Asn Cys Gln Ala Ser Gln Asn Ile Tyr Asn Thr
            20                  25                  30

Leu Ala Trp Tyr Gln Gln Lys Pro Gly Gln Pro Pro Lys Leu Leu Ile
        35                  40                  45

Tyr Val Ala Ser Thr Leu Glu Ser Gly Val Pro Ser Arg Phe Lys Gly
    50                  55                  60

Ser Gly Ser Gly Thr Gln Phe Ser Leu Thr Ile Ser Asp Leu Glu Cys
65                  70                  75                  80

Ala Asp Ala Ala Thr Tyr Tyr Cys Gln Ser Asn His Gly Ser Asn Ser
                    85                  90                  95

Asn Ser Tyr Gly Asn Thr Phe Gly Gly Gly Thr Glu Val Val Val Lys
            100                 105                 110

<210> SEQ ID NO 57
<211> LENGTH: 112
<212> TYPE: PRT
<213> ORGANISM: rabbit

<400> SEQUENCE: 57

Asp Ile Val Met Thr Gln Thr Pro Ala Ser Ala Ser Glu Pro Val Gly
1               5                   10                  15

Gly Thr Val Thr Ile Asn Cys Gln Ala Ser Gln Asn Ile Tyr Ser Thr
            20                  25                  30

Leu Ala Trp Tyr Gln Gln Lys Pro Gly Gln Pro Pro Lys Leu Leu Ile
        35                  40                  45

Tyr Leu Ala Ser Thr Leu Glu Ser Gly Val Pro Ser Arg Phe Lys Gly
    50                  55                  60

Ser Gly Ser Gly Thr Glu Phe Thr Leu Thr Ile Ser Asp Leu Glu Cys
65                  70                  75                  80

Ala Asp Ala Ala Thr Tyr Tyr Cys Gln Ser Asn His Gly Ser Asn Ser
                    85                  90                  95

Asn Ser Tyr Gly Asn Thr Phe Gly Gly Gly Thr Glu Val Val Val Lys
            100                 105                 110

<210> SEQ ID NO 58
<211> LENGTH: 110
<212> TYPE: PRT
<213> ORGANISM: rabbit

<400> SEQUENCE: 58

Gln Val Leu Thr Gln Thr Pro Ser Pro Val Ser Ala Thr Leu Gly Gly
1               5                   10                  15

Thr Val Thr Ile Asn Cys Gln Ser Ser Gln Ser Val Tyr Gly Asn Ile
            20                  25                  30
```

Trp Met Ala Trp Tyr Gln Gln Lys Ser Gly Gln Ala Pro Lys Leu Leu
            35                  40                  45

Ile Tyr Gln Ala Ser Lys Leu Ala Ser Gly Val Pro Ser Arg Phe Ser
 50                  55                  60

Gly Ser Gly Ser Gly Thr Gln Phe Ser Leu Thr Ile Ser Gly Val Gln
 65                  70                  75                  80

Cys Asp Asp Ala Ala Thr Tyr Tyr Cys Gln Gly Asn Phe Asn Thr Gly
                 85                  90                  95

Asp Arg Tyr Ala Phe Gly Gly Thr Glu Val Val Val Lys
                100                 105                 110

<210> SEQ ID NO 59
<211> LENGTH: 111
<212> TYPE: PRT
<213> ORGANISM: rabbit

<400> SEQUENCE: 59

Ile Val Met Thr Gln Thr Pro Ser Ser Lys Ser Val Ala Val Gly Asp
 1               5                  10                  15

Thr Val Thr Ile Asn Cys Gln Ala Ser Glu Ser Val Tyr Ser Asn Asn
            20                  25                  30

Arg Leu Ala Trp Tyr Gln Gln Lys Pro Gly Gln Pro Pro Lys Gln Leu
            35                  40                  45

Ile Tyr Ser Ile Ser Thr Leu Ala Ser Gly Val Pro Pro Arg Phe Ser
 50                  55                  60

Gly Ser Gly Ser Gly Thr Glu Phe Thr Leu Thr Ile Ser Asp Val Val
 65                  70                  75                  80

Cys Asp Asp Ala Ala Thr Tyr Tyr Cys Ala Gly Tyr Thr Arg Gly Lys
                 85                  90                  95

Gly Asp Asn Ser Ala Phe Gly Gly Gly Thr Glu Val Val Val Lys
                100                 105                 110

<210> SEQ ID NO 60
<211> LENGTH: 112
<212> TYPE: PRT
<213> ORGANISM: rabbit

<400> SEQUENCE: 60

Gln Val Leu Thr Gln Thr Pro Ser Ser Val Ser Ala Ala Val Gly Gly
 1               5                  10                  15

Thr Val Thr Ile Asn Cys Gln Ala Ser Gln Ser Val Tyr Ser Asn Asn
            20                  25                  30

Leu Leu Ser Trp Tyr Gln Gln Lys Pro Gly Gln Pro Pro Lys Leu Leu
            35                  40                  45

Ile Tyr Glu Ala Ser Lys Leu Ala Ser Gly Val Pro Pro Arg Phe Lys
 50                  55                  60

Gly Ser Gly Ala Gly Thr Gln Phe Thr Leu Thr Ile Ser Gly Val Gln
 65                  70                  75                  80

Cys Asp Asp Ala Ala Thr Tyr Tyr Cys Gln Gly Glu Phe Ser Cys Ser
                 85                  90                  95

Ser Ala Asp Cys Ile Gly Phe Gly Gly Gly Thr Glu Val Val Val Lys
                100                 105                 110

<210> SEQ ID NO 61
<211> LENGTH: 109
<212> TYPE: PRT
<213> ORGANISM: rabbit

<400> SEQUENCE: 61

Tyr Asp Met Thr Gln Thr Pro Ala Ser Val Ser Ala Val Gly Gly
1               5                   10                  15

Thr Val Thr Ile Lys Cys Gln Ala Ser Gln Ser Ile Ser Asn Leu Leu
            20                  25                  30

Ala Trp Tyr Gln Gln Lys Pro Gly Gln Pro Lys Leu Leu Ile Val
        35                  40                  45

Ala Ala Ser Lys Leu Ala Ser Gly Val Ser Ser Arg Phe Lys Gly Ser
50                  55                  60

Gly Ser Gly Thr Glu Phe Thr Leu Thr Ile Ser Gly Val Glu Cys Ala
65                  70                  75                  80

Asp Ala Ala Thr Tyr Tyr Cys Gln Gln Gly Trp Ser His Thr Asn Val
                85                  90                  95

Asp Asn Thr Phe Gly Gly Gly Thr Glu Val Val Val Lys
            100                 105

<210> SEQ ID NO 62
<211> LENGTH: 109
<212> TYPE: PRT
<213> ORGANISM: rabbit

<400> SEQUENCE: 62

Tyr Asp Met Thr Gln Thr Pro Ala Ser Val Glu Val Ala Val Gly Gly
1               5                   10                  15

Thr Val Thr Ile Lys Cys Gln Ala Ser Glu Lys Ile Tyr Ser Leu Leu
            20                  25                  30

Ala Trp Tyr Gln Gln Lys Ser Gly Gln Pro Pro Lys Pro Leu Ile Tyr
        35                  40                  45

Glu Ala Ser Thr Leu Ala Ser Gly Val Pro Ser Arg Phe Lys Gly Ser
50                  55                  60

Gly Tyr Gly Thr Glu Phe Thr Leu Thr Ile Ser Asp Leu Glu Cys Ala
65                  70                  75                  80

Asp Ala Ala Thr Tyr Tyr Cys Gln Gln Gly Phe Ser Ser Ser Asn Val
                85                  90                  95

Asp Asn Phe Phe Gly Gly Gly Thr Glu Val Val Val Lys
            100                 105

<210> SEQ ID NO 63
<211> LENGTH: 109
<212> TYPE: PRT
<213> ORGANISM: rabbit

<400> SEQUENCE: 63

Tyr Asp Met Thr Gln Thr Pro Ala Ser Val Glu Ala Ala Val Gly Gly
1               5                   10                  15

Thr Val Thr Ile Lys Cys Gln Ala Ser Gln Asn Ile Tyr Ser Ala Leu
            20                  25                  30

Ala Trp Tyr Gln Gln Lys Pro Gly Gln Arg Pro Lys Leu Leu Ile Tyr
        35                  40                  45

Gly Ala Ser Thr Leu Ala Ser Gly Val Ser Ser Arg Phe Lys Gly Ser
50                  55                  60

Gly Ser Gly Thr Glu Phe Thr Leu Thr Ile Ser Gly Val Glu Cys Ala
65                  70                  75                  80

Asp Ala Ala Thr Tyr Tyr Cys Gln Gln Ser His Ser Thr Ser Asn Ile
                85                  90                  95

Asp Asn Ala Phe Gly Gly Gly Thr Glu Val Val Val Lys
            100                 105

<210> SEQ ID NO 64
<211> LENGTH: 111
<212> TYPE: PRT
<213> ORGANISM: rabbit

<400> SEQUENCE: 64

Val Val Leu Thr Gln Thr Ala Ser Pro Val Ser Gly Ala Val Gly Gly
1               5                   10                  15

Thr Val Thr Ile Lys Cys Gln Ala Ser Gln Ser Ile Gly Asn Glu Leu
            20                  25                  30

Ala Trp Tyr Gln Gln Lys Pro Gly Gln Pro Lys Leu Leu Ile Tyr
        35                  40                  45

Arg Ala Ser Thr Leu Ala Ser Gly Val Pro Ser Arg Phe Lys Gly Ser
50                  55                  60

Gly Ser Gly Thr Glu Phe Thr Leu Thr Ile Ser Asp Leu Glu Cys Ala
65                  70                  75                  80

Ala Ala Thr Tyr Tyr Cys Gln Ala Tyr Tyr Ser Ser Ser
                85                  90                  95

Asn Tyr Gly Asn Val Phe Gly Gly Gly Thr Glu Val Val Val Asn
            100                 105                 110

<210> SEQ ID NO 65
<211> LENGTH: 111
<212> TYPE: PRT
<213> ORGANISM: rabbit

<400> SEQUENCE: 65

Leu Val Met Thr Gln Thr Pro Ser Pro Val Ser Ala Ala Val Gly Gly
1               5                   10                  15

Thr Val Thr Ile His Cys Gln Ala Ser Gln Ser Val Phe Ser Asn Asp
            20                  25                  30

His Leu Ser Trp Phe Gln Gln Lys Leu Gly Gln Pro Pro Lys Leu Leu
            35                  40                  45

Ile Tyr Arg Ala Ser Thr Leu Ala Ser Gly Val Pro Ser Arg Phe Lys
50                  55                  60

Gly Ser Gly Ser Gly Thr Gln Phe Thr Leu Thr Ile Ser Gly Val Glu
65                  70                  75                  80

Cys Asp Asp Ala Ala Thr Tyr Phe Cys Ala Gly Tyr Lys Asn Trp Leu
                85                  90                  95

Ser Asp Asp His Gly Phe Gly Gly Gly Thr Glu Val Val Val Arg
            100                 105                 110

<210> SEQ ID NO 66
<211> LENGTH: 112
<212> TYPE: PRT
<213> ORGANISM: rabbit

<400> SEQUENCE: 66

Asp Val Val Met Thr Gln Thr Pro Ser Ser Val Glu Ala Ala Val Gly
1               5                   10                  15

Gly Thr Val Thr Ile Lys Cys Gln Ala Thr Glu Ser Ile Asn Ser Arg
            20                  25                  30

Leu Ala Trp Tyr Gln Gln Lys Pro Gly Gln Pro Pro Lys Leu Leu Ile
            35                  40                  45

Tyr Leu Ala Ser Thr Leu Ala Ser Gly Val Pro Pro Arg Phe Lys Gly
50                  55                  60

Ser Gly Ser Gly Thr Glu Phe Thr Leu Thr Ile Ser Asp Leu Glu Cys
65                  70                  75                  80

```
Asp Asp Ala Ala Thr Tyr Tyr Cys Gln Lys Asn Tyr Asp Ser Gly Ser
                85                  90                  95

Gly Asn Phe Phe Asn Ala Phe Gly Gly Gly Thr Glu Val Val Val Lys
            100                 105                 110

<210> SEQ ID NO 67
<211> LENGTH: 110
<212> TYPE: PRT
<213> ORGANISM: rabbit

<400> SEQUENCE: 67

Ala Phe Glu Leu Thr Gln Thr Pro Ala Ser Val Glu Ala Ala Val Gly
1               5                   10                  15

Gly Thr Val Thr Ile Lys Cys Gln Ala Ser Glu Ser Ile Ser Ser Arg
            20                  25                  30

Leu Ala Trp Tyr Gln Gln Lys Pro Gly Gln Pro Pro Lys Leu Leu Ile
        35                  40                  45

Tyr Asp Ala Ser Thr Leu Glu Ser Gly Val Pro Ser Arg Phe Ser Gly
    50                  55                  60

Ser Gly Ser Gly Thr Glu Phe Thr Leu Thr Ile Arg Gly Val Gln Cys
65                  70                  75                  80

Ala Asp Ala Ala Thr Tyr Tyr Cys Gln Ser Tyr His Asp Gly Ser Gly
                85                  90                  95

Thr Thr Phe Ser Phe Gly Gly Gly Thr Glu Val Val Val Glu
            100                 105                 110

<210> SEQ ID NO 68
<211> LENGTH: 110
<212> TYPE: PRT
<213> ORGANISM: rabbit

<400> SEQUENCE: 68

Leu Val Met Thr Gln Thr Pro Ser Ser Thr Ser Glu Pro Val Gly Gly
1               5                   10                  15

Thr Val Thr Ile Asn Cys Gln Ala Ser Asp Asn Ile Tyr Ser Gly Leu
            20                  25                  30

Ala Trp Tyr Gln Gln Lys Pro Gly Gln Pro Pro Lys Leu Leu Ile Tyr
        35                  40                  45

Asp Ala Ser Asn Leu Glu Thr Gly Val Pro Ser Arg Phe Lys Gly Ser
    50                  55                  60

Gly Ser Gly Thr Gln Phe Thr Leu Thr Ile Ser Gly Val Gln Cys Ala
65                  70                  75                  80

Asp Ala Ala Thr Tyr Tyr Cys Leu Gly Val Tyr Ala Tyr Ser Ser Asp
                85                  90                  95

Asp Gly Ala Ala Phe Gly Gly Gly Thr Glu Val Val Val Lys
            100                 105                 110

<210> SEQ ID NO 69
<211> LENGTH: 110
<212> TYPE: PRT
<213> ORGANISM: rabbit

<400> SEQUENCE: 69

Leu Val Met Thr Gln Thr Pro Ser Ser Thr Ser Glu Pro Val Gly Gly
1               5                   10                  15

Thr Val Thr Ile Asn Cys Gln Ala Ser Asp Asn Ile Tyr Arg Gly Leu
            20                  25                  30

Ala Trp Tyr Gln Gln Lys Pro Gly Gln Pro Pro Lys Gln Leu Ile Tyr
```

35                  40                  45

Asp Ala Ser Thr Leu Gln Ser Gly Val Pro Ser Arg Phe Lys Gly Ser
 50                  55                  60

Gly Ser Gly Thr Gln Phe Thr Leu Thr Ile Ser Gly Val Gln Cys Asp
 65                  70                  75                  80

Asp Ala Ala Thr Tyr Tyr Cys Leu Gly Val Tyr Gly Tyr Ser Ser Asp
                 85                  90                  95

Asp Gly Ala Ala Phe Gly Gly Gly Thr Glu Val Val Val Lys
                100                 105                 110

<210> SEQ ID NO 70
<211> LENGTH: 112
<212> TYPE: PRT
<213> ORGANISM: rabbit

<400> SEQUENCE: 70

Gln Val Leu Thr Gln Thr Pro Ser Pro Val Ser Ala Ala Val Gly Gly
  1               5                  10                  15

Thr Val Thr Ile Asn Cys Gln Ala Ser Gln Ser Val Tyr Asn Asn Lys
                 20                  25                  30

Asn Leu Ala Trp Tyr Gln Gln Lys Pro Gly Gln Pro Pro Lys Leu Leu
             35                  40                  45

Ile Tyr Glu Thr Ser Thr Leu Ala Ser Gly Val Ser Ser Arg Phe Arg
 50                  55                  60

Gly Ser Gly Ser Gly Thr Gln Phe Thr Leu Thr Ile Ser Gly Val Gln
 65                  70                  75                  80

Cys Asp Asp Ala Ala Thr Tyr Tyr Cys Gln Gly Glu Phe Ser Cys Ser
                 85                  90                  95

Ser Gly Asp Cys Ser Ala Phe Gly Gly Gly Thr Glu Val Val Val Lys
                100                 105                 110

<210> SEQ ID NO 71
<211> LENGTH: 112
<212> TYPE: PRT
<213> ORGANISM: rabbit

<400> SEQUENCE: 71

Gln Val Leu Thr Gln Thr Pro Ser Pro Val Ser Ala Ala Val Gly Gly
  1               5                  10                  15

Thr Val Ala Ile Asn Cys Gln Ser Ser Gln Ser Val Tyr Asn Asn Asn
                 20                  25                  30

Leu Leu Ala Trp Tyr Gln Gln Lys Pro Gly Gln Pro Pro Lys Leu Leu
             35                  40                  45

Ile Tyr Glu Thr Ser Thr Leu Ala Ser Gly Val Ser Ser Arg Phe Lys
 50                  55                  60

Gly Ser Gly Ser Gly Thr Gln Phe Thr Leu Thr Ile Ser Gly Val Gln
 65                  70                  75                  80

Cys Asp Asp Ala Ala Thr Tyr Tyr Cys Gln Gly Glu Phe Ser Cys Ser
                 85                  90                  95

Ser Gly Asp Cys Ser Ala Phe Gly Gly Gly Thr Glu Val Val Val Lys
                100                 105                 110

<210> SEQ ID NO 72
<211> LENGTH: 110
<212> TYPE: PRT
<213> ORGANISM: rabbit

<400> SEQUENCE: 72

```
Asp Val Val Met Thr Gln Thr Pro Ser Ser Val Ser Ala Ala Val Gly
1               5                   10                  15

Gly Thr Val Thr Ile Asn Cys Gln Ala Ser Gln Arg Ile Tyr Thr Asn
            20                  25                  30

Leu Ala Trp Tyr Gln Gln Lys Ser Gly Gln Pro Pro Lys Leu Leu Met
        35                  40                  45

Tyr Leu Ala Ser Thr Leu Ala Ser Gly Val Pro Ser Arg Phe Lys Gly
50                  55                  60

Ser Gly Ser Gly Thr Glu Phe Thr Leu Thr Ile Ser Gly Val Gln Cys
65                  70                  75                  80

Ala Asp Ala Ala Thr Tyr Tyr Cys Gln Tyr Thr Asp Pro Gly Ser Gly
                85                  90                  95

Asp Asp Ser Pro Phe Gly Gly Gly Thr Glu Val Val Val Lys
            100                 105                 110
```

<210> SEQ ID NO 73
<211> LENGTH: 109
<212> TYPE: PRT
<213> ORGANISM: rabbit

<400> SEQUENCE: 73

```
Tyr Asp Met Thr Gln Thr Pro Ala Ser Val Ser Glu Pro Val Gly Gly
1               5                   10                  15

Thr Val Thr Ile Lys Cys Gln Ala Ser Glu Asn Ile Tyr Thr Ser Leu
            20                  25                  30

Ala Trp Tyr Gln Gln Lys Pro Gly Gln Pro Pro Lys Leu Leu Ile Tyr
        35                  40                  45

Ser Ala Ser Thr Leu Ala Ser Gly Val Pro Ser Arg Phe Lys Gly Ser
50                  55                  60

Gly Ser Gly Thr Glu Phe Thr Leu Thr Ile Ser Asp Leu Glu Cys Ala
65                  70                  75                  80

Asp Ala Ala Ser Tyr Tyr Cys Gln Gln Gly Phe Ala Thr Ser Asn Val
                85                  90                  95

Glu Asn Pro Phe Gly Gly Gly Thr Glu Val Val Val Lys
            100                 105
```

<210> SEQ ID NO 74
<211> LENGTH: 109
<212> TYPE: PRT
<213> ORGANISM: rabbit

<400> SEQUENCE: 74

```
Tyr Asp Met Thr Gln Thr Pro Ala Ser Val Ser Glu Pro Val Gly Gly
1               5                   10                  15

Thr Val Thr Ile Lys Cys Gln Ala Ser Glu Ser Ile Tyr Ser Gly Leu
            20                  25                  30

Ala Trp Tyr Gln Gln Lys Pro Gly Gln Pro Pro Lys Leu Leu Ile Tyr
        35                  40                  45

Gln Ala Ser Thr Leu Ala Ser Gly Val Ser Ser Arg Phe Lys Gly Ser
50                  55                  60

Gly Ser Gly Thr Asp Phe Thr Leu Ala Ile Ser Asp Leu Glu Cys Ala
65                  70                  75                  80

Asp Ala Ala Thr Tyr Tyr Cys Gln Gln Gly Phe Gly Thr Ser Asn Val
                85                  90                  95

Glu Asn Pro Phe Gly Gly Gly Ser Glu Val Val Val Lys
            100                 105
```

<210> SEQ ID NO 75
<211> LENGTH: 109
<212> TYPE: PRT
<213> ORGANISM: rabbit

<400> SEQUENCE: 75

Tyr Asp Met Thr Gln Thr Pro Ala Ser Val Ser Glu Pro Val Gly Gly
 1               5                  10                  15

Thr Val Thr Ile Lys Cys Gln Ala Ser Glu Asn Ile Tyr Ser Ser Leu
            20                  25                  30

Ala Trp Tyr Gln Gln Lys Pro Gly Gln Pro Pro Lys Leu Leu Ile Tyr
        35                  40                  45

Ser Ala Ser Thr Leu Ala Ser Gly Val Ser Ser Arg Phe Lys Gly Ser
    50                  55                  60

Gly Ser Gly Thr Glu Phe Thr Leu Thr Ile Ser Asp Leu Glu Cys Ala
65                  70                  75                  80

Asp Ala Ala Thr Tyr Tyr Cys Gln Gln Gly Phe Gly Thr Ser Asn Val
                85                  90                  95

Glu Asn Pro Phe Gly Gly Gly Thr Glu Val Val Val Lys
            100                 105

<210> SEQ ID NO 76
<211> LENGTH: 109
<212> TYPE: PRT
<213> ORGANISM: rabbit

<400> SEQUENCE: 76

Tyr Asp Met Thr Gln Thr Pro Ala Ser Val Ser Glu Pro Val Gly Gly
 1               5                  10                  15

Thr Val Thr Ile Lys Cys Gln Ala Ser Glu Asn Ile Tyr Ser Ser Leu
            20                  25                  30

Ala Trp Tyr Gln Gln Lys Pro Gly Gln Pro Pro Lys Leu Leu Ile Tyr
        35                  40                  45

Ser Ala Ser Thr Leu Ala Ser Gly Val Ser Ser Arg Phe Lys Gly Ser
    50                  55                  60

Gly Ser Gly Thr Glu Phe Thr Leu Thr Ile Ser Gly Val Gln Cys Glu
65                  70                  75                  80

Asp Ala Ala Thr Tyr Tyr Cys Gln Gln Gly Phe Gly Thr Asn Asn Val
                85                  90                  95

Glu Asn Pro Phe Gly Gly Gly Thr Glu Val Val Val Lys
            100                 105

<210> SEQ ID NO 77
<211> LENGTH: 109
<212> TYPE: PRT
<213> ORGANISM: rabbit

<400> SEQUENCE: 77

Tyr Asp Met Thr Gln Thr Pro Ala Ser Val Glu Ala Ala Val Gly Gly
 1               5                  10                  15

Thr Val Thr Ile Lys Cys Gln Ala Ser Gln Asn Ile Tyr Ser Asn Leu
            20                  25                  30

Ala Trp Tyr Gln Gln Lys Pro Gly Gln Arg Pro Lys Leu Leu Ile Tyr
        35                  40                  45

Gly Ala Ser Asn Leu Glu Ser Gly Val Pro Ser Arg Phe Lys Gly Ser
    50                  55                  60

Gly Ser Gly Thr Glu Tyr Thr Leu Thr Ile Ser Gly Val Gln Cys Asp
65                  70                  75                  80

Asp Ala Ala Thr Tyr Tyr Cys Gln Gln Gly His Ser Ile Ser Asp Val
                85                  90                  95

Asp Asn Leu Phe Gly Gly Gly Thr Glu Val Val Val Lys
            100                 105

<210> SEQ ID NO 78
<211> LENGTH: 109
<212> TYPE: PRT
<213> ORGANISM: rabbit

<400> SEQUENCE: 78

Gln Val Leu Thr Gln Thr Pro Ser Pro Val Ala Ala Val Gly Gly
 1               5                  10                  15

Thr Val Thr Ile Ser Cys Gln Cys Ser Gln Ser Val Ala Asn Asn Asn
                20                  25                  30

Glu Leu Ser Trp Tyr Gln Gln Lys Pro Gly Gln Pro Pro Lys Arg Leu
            35                  40                  45

Ile Tyr Gly Ala Ser Asn Leu Ala Ser Gly Val Pro Ser Arg Phe Lys
        50                  55                  60

Gly Ser Gly Ser Gly Thr Gln Phe Thr Leu Thr Ile Ser Asp Leu Glu
65                  70                  75                  80

Cys Asp Asp Ala Ala Thr Tyr Tyr Cys Gln Gly Tyr Val Lys Glu His
                85                  90                  95

Gln Tyr Pro Phe Gly Gly Gly Thr Glu Val Val Val Lys
            100                 105

<210> SEQ ID NO 79
<211> LENGTH: 112
<212> TYPE: PRT
<213> ORGANISM: rabbit

<400> SEQUENCE: 79

Asp Val Val Met Thr Gln Thr Pro Ala Ser Val Ser Glu Pro Val Gly
 1               5                  10                  15

Gly Thr Val Thr Ile Lys Cys Gln Ala Ser Gln Thr Val Gly Asn Ser
                20                  25                  30

Leu Ala Trp Tyr Gln Gln Lys Pro Gly Gln Pro Pro Lys Leu Leu Ile
            35                  40                  45

Tyr Arg Ala Ser Thr Leu Ala Ser Gly Val Pro Ser Arg Phe Lys Gly
        50                  55                  60

Ser Gly Ser Gly Thr Gln Phe Thr Leu Thr Ile Ser Asp Leu Glu Cys
65                  70                  75                  80

Ala Asp Ala Ala Thr Tyr Tyr Cys Gln Ser Phe Tyr Tyr Ser Gly Ser
                85                  90                  95

Asn Ser Tyr Gly Tyr Ala Phe Gly Gly Gly Thr Glu Val Val Val Lys
            100                 105                 110

<210> SEQ ID NO 80
<211> LENGTH: 109
<212> TYPE: PRT
<213> ORGANISM: rabbit

<400> SEQUENCE: 80

Ile Asp Met Thr Gln Thr Pro Ala Ser Val Glu Val Val Gly Gly
 1               5                  10                  15

Thr Val Thr Ile Lys Cys Gln Ala Ser Gln Ser Ile Ser Asp Trp Leu
                20                  25                  30

Ala Trp Tyr Gln Gln Lys Pro Gly Gln Arg Pro Lys Leu Leu Ile Tyr
            35                  40                  45

-continued

Gly Ala Ser Arg Leu Ala Ser Gly Phe Pro Ser Arg Phe Ser Gly Ser
            50                  55                  60

Gly Ser Gly Thr Gln Phe Thr Leu Thr Ile Ser Gly Val Glu Cys Ala
 65                  70                  75                  80

Asp Ala Ala Thr Tyr Tyr Cys Gln Gln Gly Trp Ser Ser Tyr Val
                85                  90                  95

Asp Asn Leu Phe Gly Gly Gly Thr Glu Val Val Val Lys
                100                 105

<210> SEQ ID NO 81
<211> LENGTH: 108
<212> TYPE: PRT
<213> ORGANISM: rabbit

<400> SEQUENCE: 81

Glu Val Val Met Thr Gln Thr Pro Ser Ser Val Glu Ala Ala Val Gly
 1               5                  10                  15

Gly Thr Val Thr Ile Lys Cys Gln Ala Ser Gln Ser Ile Tyr Ser Tyr
                20                  25                  30

Leu Ser Trp Tyr Gln Gln Lys Pro Gly Gln Arg Pro Lys Leu Leu Ile
            35                  40                  45

Tyr Glu Ala Ser Ile Leu Ala Ser Gly Val Pro Ser Arg Phe Lys Gly
    50                  55                  60

Ser Gly Ser Gly Thr Gln Phe Thr Leu Thr Ile Ser Asp Leu Glu Cys
 65                  70                  75                  80

Asp Asp Ala Ala Thr Tyr Tyr Cys Gln Asn Asn Val Ala Ile Leu Gly
                85                  90                  95

Thr Ala Phe Gly Gly Gly Thr Glu Val Val Val Asn
                100                 105

<210> SEQ ID NO 82
<211> LENGTH: 112
<212> TYPE: PRT
<213> ORGANISM: rabbit

<400> SEQUENCE: 82

Asp Ile Val Met Thr Gln Thr Pro Ala Ser Val Glu Ala Ala Val Gly
 1               5                  10                  15

Gly Thr Val Thr Ile Lys Cys Gln Ala Ser Gln Ser Ile Gly Ser Asn
                20                  25                  30

Leu Ala Trp Tyr Gln Gln Lys Pro Gly Gln Pro Pro Lys Leu Leu Ile
            35                  40                  45

Tyr Asp Ala Ser Thr Leu Pro Ser Gly Val Pro Ser Arg Phe Lys Gly
    50                  55                  60

Ser Gly Ser Gly Thr Gln Phe Thr Leu Thr Ile Ser Asp Leu Glu Cys
 65                  70                  75                  80

Ala Asp Ala Ala Thr Tyr Tyr Cys Gln Ser Tyr Tyr Tyr Ser Ser His
                85                  90                  95

Ser Thr Thr Tyr Trp Ala Phe Gly Gly Gly Thr Glu Val Val Val Lys
                100                 105                 110

<210> SEQ ID NO 83
<211> LENGTH: 110
<212> TYPE: PRT
<213> ORGANISM: rabbit

<400> SEQUENCE: 83

Phe Glu Leu Thr Gln Thr Pro Ser Pro Val Ser Gly Ala Val Gly Gly

```
                1               5                   10                  15
Thr Val Thr Ile Asn Cys Gln Ala Ser Gln Ser Ile Ser Asn Glu Leu
                20                  25                  30

Ala Trp Tyr Gln Gln Lys Pro Gly Gln Pro Lys Leu Leu Ile Tyr
            35                  40                  45

Arg Ala Ser Thr Leu Ala Ser Gly Val Ser Ser Arg Phe Lys Gly Ser
            50                  55                  60

Gly Ser Gly Thr Asp Tyr Thr Leu Thr Ile Ser Asp Leu Glu Cys Ala
65                  70                  75                  80

Asp Ala Ala Thr Tyr Tyr Cys Gln Ser Tyr Tyr Tyr Asp Leu Thr Ile
                85                  90                  95

Asn Gly Asn Pro Phe Gly Gly Gly Thr Glu Val Val Val Ile
                100                 105                 110

<210> SEQ ID NO 84
<211> LENGTH: 110
<212> TYPE: PRT
<213> ORGANISM: rabbit

<400> SEQUENCE: 84

Phe Glu Leu Thr Gln Thr Pro Ser Pro Val Ser Gly Ala Val Gly Gly
1               5                   10                  15

Thr Val Thr Ile Lys Cys Gln Ala Ser Gln Asn Ile Tyr Ser Asp Leu
                20                  25                  30

Ala Trp Tyr Gln Gln Lys Pro Gly Gln Pro Pro Lys Leu Leu Ile Tyr
            35                  40                  45

Arg Ala Ser Thr Leu Thr Ser Gly Val Ser Ser Arg Phe Lys Gly Ser
            50                  55                  60

Gly Ser Gly Thr Glu Phe Thr Leu Thr Ile Ser Asp Leu Glu Cys Ala
65                  70                  75                  80

Asp Ala Ala Thr Tyr Tyr Cys Gln Ser Tyr Tyr Tyr Asp Gly Thr Thr
                85                  90                  95

Asn Gly Asn Pro Phe Gly Gly Gly Thr Glu Val Val Val Lys
                100                 105                 110

<210> SEQ ID NO 85
<211> LENGTH: 110
<212> TYPE: PRT
<213> ORGANISM: rabbit

<400> SEQUENCE: 85

Phe Glu Leu Thr Gln Thr Pro Ser Ser Val Glu Ala Ala Val Gly Gly
1               5                   10                  15

Thr Val Thr Ile Lys Cys Gln Ala Ser Gln Ser Ile Val Ser Asp Leu
                20                  25                  30

Ala Trp Tyr Gln Gln Lys Pro Gly Gln Pro Pro Lys Leu Leu Ile Tyr
            35                  40                  45

Arg Ala Ser Thr Leu Ala Ser Gly Val Ser Ser Arg Phe Lys Gly Ser
            50                  55                  60

Gly Ser Gly Thr Gln Phe Thr Leu Thr Ile Ser Asp Leu Glu Cys Ala
65                  70                  75                  80

Asp Ala Ala Thr Tyr Tyr Cys Gln Ser Tyr Tyr Tyr Asp Thr Thr Thr
                85                  90                  95

Pro Gly Asn Ala Phe Gly Gly Gly Thr Glu Val Val Val Ser
                100                 105                 110

<210> SEQ ID NO 86
```

```
<211> LENGTH: 110
<212> TYPE: PRT
<213> ORGANISM: rabbit

<400> SEQUENCE: 86

Ile Glu Met Thr Gln Thr Pro Phe Ser Val Ser Ala Ala Gly Gly
 1               5                  10                  15

Thr Val Thr Ile Asn Cys Gln Ala Ser Glu Asn Ile Val Ser Asn Leu
            20                  25                  30

Ala Trp Tyr Gln Gln Lys Pro Gly Gln Pro Thr Leu Leu Ile Tyr
            35                  40                  45

Ala Ala Ser Tyr Leu Ala Ser Gly Val Pro Ser Arg Phe Lys Gly Ser
        50                  55                  60

Gly Ser Gly Thr Glu Tyr Thr Leu Thr Ile Ser Gly Val Gln Cys Ala
 65                 70                  75                  80

Asp Ala Ala Thr Tyr Tyr Cys Gln Ser Ala Tyr Tyr Ala Ser Ser Gly
                85                  90                  95

Asp Thr Trp Ala Phe Gly Gly Gly Thr Glu Val Val Val Arg
            100                 105                 110

<210> SEQ ID NO 87
<211> LENGTH: 110
<212> TYPE: PRT
<213> ORGANISM: rabbit

<400> SEQUENCE: 87

Val Val Leu Thr Gln Thr Val Ser Pro Val Ser Gly Ala Val Gly Gly
 1               5                  10                  15

Thr Val Thr Ile Lys Cys Gln Ala Ser Gln Asn Ile Tyr Ser Asp Leu
            20                  25                  30

Ala Trp Tyr Gln Gln Lys Pro Gly Gln Pro Pro Lys Leu Leu Ile Tyr
            35                  40                  45

Ser Ala Ser Lys Leu Ala Ser Gly Val Pro Ser Arg Phe Ser Gly Ser
        50                  55                  60

Arg Ser Gly Thr Glu Phe Thr Leu Thr Ile Asn Asp Leu Glu Cys Ala
 65                 70                  75                  80

Asp Ala Ala Thr Tyr Tyr Cys Gln Asn Tyr Tyr Tyr Asp Ser Asn Gly
                85                  90                  95

Gly Asp Asn Ala Phe Gly Gly Gly Thr Glu Val Val Val Gln
            100                 105                 110

<210> SEQ ID NO 88
<211> LENGTH: 112
<212> TYPE: PRT
<213> ORGANISM: rabbit

<400> SEQUENCE: 88

Gln Val Leu Thr Gln Thr Pro Ser Ser Val Ser Ala Ala Val Gly Asp
 1               5                  10                  15

Thr Val Thr Ile Asn Cys Gln Ala Ser Glu Ser Leu Tyr Asn Lys Lys
            20                  25                  30

Asn Leu Ala Trp Tyr Gln Gln Lys Pro Gly Gln Pro Pro Lys Leu Leu
            35                  40                  45

Ile Tyr Glu Ala Ser Thr Leu Ala Ser Gly Val Ser Ser Arg Phe Lys
        50                  55                  60

Gly Ser Gly Ser Gly Thr Gln Phe Thr Leu Thr Ile Ser Gly Val Gln
 65                 70                  75                  80

Cys Asp Asp Ala Ala Thr Tyr Tyr Cys Gln Gly Glu Phe Ser Asp Ser
```

-continued

```
                85                  90                  95
Ser Gly Asp Cys Asn Ala Phe Gly Gly Gly Thr Glu Val Val Val Lys
                    100                 105                 110
```